(12) United States Patent
Bey et al.

(10) Patent No.: US 9,446,117 B2
(45) Date of Patent: Sep. 20, 2016

(54) ROTAVIRUS SUBUNIT VACCINES AND METHODS OF MAKING AND USE THEREOF

(71) Applicants: Russell F. Bey, Arden Hills, MN (US); Randy S Simonson, Worthington, MN (US); Kamesh Reddy Sirigireddy, Sioux Falls, SD (US); Benjamin Matthew Hause, Currie, MN (US)

(72) Inventors: Russell F. Bey, Arden Hills, MN (US); Randy S Simonson, Worthington, MN (US); Kamesh Reddy Sirigireddy, Sioux Falls, SD (US); Benjamin Matthew Hause, Currie, MN (US)

(73) Assignee: Merial, Inc., Duluth, GA (US)

( * ) Notice: Subject to any disclaimer, the term of this patent is extended or adjusted under 35 U.S.C. 154(b) by 320 days.

(21) Appl. No.: 13/767,569

(22) Filed: Feb. 14, 2013

(65) Prior Publication Data

US 2013/0209507 A1 Aug. 15, 2013

Related U.S. Application Data

(60) Provisional application No. 61/598,624, filed on Feb. 14, 2012.

(51) Int. Cl.
| | |
|---|---|
| *A61K 39/15* | (2006.01) |
| *A61K 39/12* | (2006.01) |
| *A61K 39/21* | (2006.01) |
| *C07K 16/10* | (2006.01) |
| *C07K 14/005* | (2006.01) |
| *A61K 39/00* | (2006.01) |
| *A61K 38/00* | (2006.01) |

(52) U.S. Cl.
CPC .............. *A61K 39/15* (2013.01); *A61K 39/12* (2013.01); *A61K 39/21* (2013.01); *A61K 38/00* (2013.01); *A61K 2039/5258* (2013.01); *A61K 2039/545* (2013.01); *A61K 2039/552* (2013.01); *A61K 2039/55505* (2013.01); *A61K 2039/55566* (2013.01); *A61K 2039/55577* (2013.01); *C07K 14/005* (2013.01); *C07K 16/10* (2013.01); *C07K 2319/00* (2013.01); *C12N 2720/12334* (2013.01)

(58) Field of Classification Search
None
See application file for complete search history.

(56) References Cited

U.S. PATENT DOCUMENTS

| 5,298,244 A | 3/1994 | Redmond et al. |
| 5,827,696 A | 10/1998 | Estes |

(Continued)

FOREIGN PATENT DOCUMENTS

| WO | WO 2006/007555 A2 * | 1/2006 | ............ C07K 14/14 |
| WO | WO 2006/113373 A2 * | 10/2006 | ............ A61K 39/12 |

(Continued)

OTHER PUBLICATIONS

Matthijnssens, et al. Full Genome-Based Classification of Rotaviruses Reveals a Common Origin between Human Wa-Like and Porcine Rotavirus Strains and Human DS-1-Like and Bovine Rotavirus Strains. J. Virol. 2008; 82(7): 3204-3219.*

(Continued)

*Primary Examiner* — Daniel E Kolker
*Assistant Examiner* — Stuart W Snyder
(74) *Attorney, Agent, or Firm* — Judy Jarecki-Black; Chad Kitchen; Merial, Inc.

(57) ABSTRACT

The present invention provides Rotavirus antigenic polypeptides or antigens that elicit an immune response in animal or human against rotavirus, compositions comprising said rotavirus polypeptides, methods of vaccination against rotavirus, and kits for use with such methods and compositions. The invention further provide novel expression vectors for producing the vaccine antigenic polypeptides.

9 Claims, 20 Drawing Sheets

(56) References Cited

U.S. PATENT DOCUMENTS

| | | | |
|---|---|---|---|
| 5,891,676 | A | 4/1999 | Estes |
| 6,180,407 | B1 | 1/2001 | Bernard et al. |
| 6,187,319 | B1 | 2/2001 | Herrmann et al. |
| 6,210,682 | B1 | 4/2001 | Estes et al. |
| 6,589,529 | B1 | 7/2003 | Choi et al. |
| 6,673,355 | B1 | 1/2004 | Estes et al. |
| 6,716,431 | B1 | 4/2004 | Tian et al. |
| 6,867,353 | B2 | 3/2005 | Kim et al. |
| 7,183,097 | B1 | 2/2007 | Gerdes et al. |
| 7,311,918 | B2 | 12/2007 | Choi et al. |
| 7,371,395 | B2 * | 5/2008 | Parisot et al. ............. 424/283.1 |
| 7,595,185 | B2 | 9/2009 | Gerdes et al. |
| 7,595,186 | B2 | 9/2009 | Gerdes et al. |
| 7,790,178 | B2 | 9/2010 | Gore et al. |
| 2003/0175303 | A1 | 9/2003 | Kim |
| 2004/0009187 | A1 | 1/2004 | Choi |
| 2007/0276130 | A1 | 11/2007 | Dormitzer |
| 2008/0182327 | A1 | 7/2008 | Gerdes et al. |
| 2008/0299661 | A1 | 12/2008 | Bernard |
| 2010/0047763 | A1 | 2/2010 | Góes |
| 2011/0171316 | A1 | 7/2011 | Jiang |
| 2011/0207173 | A1 | 8/2011 | Sodoyer et al. |

FOREIGN PATENT DOCUMENTS

| | | | |
|---|---|---|---|
| WO | WO 2007/103042 A2 * | 9/2007 | ............. A61K 39/02 |
| WO | WO2010007246 A1 | 1/2010 | |

OTHER PUBLICATIONS

Dennehy. Rotavirus Vaccines: an Overview. Clin. Microbiol. Rev. 2008; 21(1): 198-208.*

Li et al. Recombinant multi-epitope vaccine induce predefined epitope-specific antibodies against HIV-1. Immunol. Lett. 2002; 84: 153-157.*

NSP4 [Porcine rotavirus C]; NCBI GenBank: AAC83711.1; published Oct. 30, 2000.*

Lee et al. Molecular Characterization of Two Strains of Porcine Group C Rotavirus. J. Microbiol. 20111; 49(6): 1058-1062.*

Jeong et al. Detection and molecular characterization of porcine group C rotaviruses in South Korea. Vet. Microbiol. 2009; 138: 217-224.*

Jain et al. Infrastructure for the life sciences: design and implementation of the UniProt website. BMC Bioinformatics, 10:136 (2009).*

White. Vaccination for the Smaller Pig Population Part 1. 2010; pp. 1-7—downloaded Dec. 17, 2015.*

Davis, H.L. Novel vaccines and adjuvant systems. Human Vacc. 2008; 4:3, 246-250.*

Lin_WP. Determination of Human Rotavirus VP6 Genogroups I and II by Reverse Transcription-Pcrjournal of Clinical Microbiology, Oct. 2008, p. 3330-3337 vol. 46, No. 10.

Clark_HF. "The New Pentavalent Rotavirus Vaccine Composed of Bovine (Strain WC3)—Human Rotavirus Reassortants." Pediatric Infectious Disease Journal • vol. 25, No. 7, Jul. 2006.

Krattiger_A. "Rotavirus Vaccine: NIH Office of Technology Transfer." CS 30 Handbook of Best Practices: Executive Guide. © 2007.

pStaby Product Manual. © 2007.

El-Attar L et al. "Comparison of the efficacy of rotavirus VLP vaccines to a live homologous rotavirus vaccine in a pig model of rotavirus disease." Vaccine v.27, No. 24, May 21, 2009.

Qiao Xinyuan et al. "Recombinant porcine rotavirus VP4 and VP4-LTB expressed in Lactobacillus casei induced mucosal and systemic antibody responses in mice", BMC Microbiology vol. 9, No. 1, Dec. 4, 2009.

Ko Chang et al. Virus Genes, vol. 18, No. 3, 1999, pp. 229-233.

* cited by examiner

ATCTGGTTCCGCGT*GGATCC*GAATTCGAGC TCCGTCGAC*AAGCTT*GCGGCCGCAC
                    BamH I                                     Hind III

```
                  1                                                50
SEQ ID 17   (1)   ATCACCTCAAAAACTGTGATTGGTAAATTCAAGACTGAAAACAATATTAG
SEQ ID 19   (1)   ATCACCTCAAAGACTGTGATTAGTAAGTTCAAGACTGAAAATGACATTAG
SEQ ID 21   (1)   ATCACCTCAAAGACTGTGATTAGTAAGTTCAAGACTGAAAATGACATTAG
SEQ ID 23   (1)   ATCACCTCAAAGACTGTGATTAGTAAGTTCAAGACTGAAAATGACATTAG
SEQ ID 25   (1)   ATCACCTCAAAGACTGTGATTAGTAAGTTCAAGACTGAAAATGACATTAG
SEQ ID 27   (1)   ATCACCTCAAAGACTGTGATTAGTAAGTTCAAGACTGAAAATGACATTAG
SEQ ID 29   (1)   ATCACCTCGAAGACTGTGATTAGTAAGTTCAAGACTGAAAATGACATTAG
SEQ ID 31   (1)   ATCACCTCAAAGACTGTGATTAGTAAGTTCAAGACTGAAAATGACATTAG
SEQ ID 33   (1)   ATCACCTCAAAGACTGTGATTAGTAAGTTCAAGACTGAAAATGACATTAG
SEQ ID 35   (1)   ATCACCTCAAAGACTGTGATTAGTAAGTTCAAGACTGAAAATGACATTAG
SEQ ID 37   (1)   ATCACCTCAAAAACTGTGATTGGTAAATTCAAGACTGAAAACAATATTAG
SEQ ID 39   (1)   ATCACCTCAAAGACTGTGATTAGTAAGTTCAAGACTGAAAATGACATTAG
                  51                                               100
SEQ ID 17   (51)  TCATCAGAATGACGACATTCATAAAGAATATGAAGAGGTGATGAAAACAAA
SEQ ID 19   (51)  CCACCAGAACAATGATATCAATAAGGAATATGAAGAGGTGATGAAAACAAA
SEQ ID 21   (51)  CCACCAGAACAACGATATCAATAAGGAATATGAAGAGGTGATGAAAACAAA
SEQ ID 23   (51)  CCACCAGAACAACGATATCAATAAGGAATATGAAGAGGTGATGAAAACAAA
SEQ ID 25   (51)  CCACCAGAACAACGATATCAATAAGGAATATGAAGAGGTAATGAAAACAAA
SEQ ID 27   (51)  CCACCAGAACAACGATATCAATAAGGAATATGAAGAGGTGATGAAAACAAA
SEQ ID 29   (51)  CCACCAGAACAACGATATCAATAAGGAATATGAAGAGGTGATGAAAACAAA
SEQ ID 31   (51)  CCACCAGAACAACGATATCAATAAGGAATATGAAGAGGTGATGAAAACAAA
SEQ ID 33   (51)  CCACCAGAACAACGATATCAATAAGGAATATGAAGAGGTGATGAAAACAAA
SEQ ID 35   (51)  CCACCAGAACAACGATATCAATAAGGAATATGAAGAGGTGATGAAAACAAA
SEQ ID 37   (51)  TCATCAGAATGACGACATTCATAAAGAATATGAAGAGGTGATGAAAACAAA
SEQ ID 39   (51)  CCACCAGAACAACGATATCAATAAGGAATATGAAGAGGTGATGAAAACAAA
                  101                                              150
SEQ ID 17   (101) TGCGTGACATGAGAGTTCATGTAACTGCACTATTTAATAGTATACATAAG
SEQ ID 19   (101) TGCGTGAAATGAGAGTTCAT---ACTGCATTATTTAATAGTATACATAAA
SEQ ID 21   (101) TGCGTGAAATGAGAGTTCAT---ACTGCATTATTTAATAGTATACATAAA
SEQ ID 23   (101) TGCGTGAAATGAGAGTTCAT---ACTGCATTATTTAATAGTATACATAAA
SEQ ID 25   (101) TGCGTGAAATGAGAGTTCAT---ACTGCATTATTTAATAGTATACATAAA
SEQ ID 27   (101) TGCGTGAAATGAGAGTTCAT---ACTGCATTATTTAATAGTATACATAAA
SEQ ID 29   (101) TGCGTGAAATGAGAGTTCAT---ACTGCATTATTTAATAGTATACATAAA
SEQ ID 31   (101) TGCGTGAAATGAGAGTTCAT---ACTGCATTATTTAATAGTATACATAAA
SEQ ID 33   (101) TGCGTGAAATGAGAGTTCAT---ACTGCATTATTTAATAGTATACATAAA
SEQ ID 35   (101) TGCGTGAAATGAGAGTTCAT---ACTGCATTATTTAATAGTATACATAAA
SEQ ID 37   (101) TGCGTGACATGAGAGTTCATGTAACTGCACTATTTAATAGTATACATAAG
SEQ ID 39   (101) TGCGTGAAATGAGAGTTCAT---ACTGCATTATTTAATAGTATACATAAA
                  151                                              200
SEQ ID 17   (151) GATAATATGGAGTGGACAATGAGTGAATCATTCGCACAGAAAAGAAGCG
SEQ ID 19   (148) GATAATATGGAGTGGACAATGAGTGAATCAATTCGCACAGAAAAGAAGCG
SEQ ID 21   (148) GATAATATGGAATGGACAATGAGTGAATCAATTCGCACAGAAAAGAAGCG
SEQ ID 23   (148) GATAATATGGAGTGGACAATGAGTGAATCAATTCGCACAGAAAAGAAGCG
SEQ ID 25   (148) GATAATATGGAGTGGAGAATGAGTGAATCAATTCGCACAGAAAAGAAGCG
SEQ ID 27   (148) GATAATATGGAGTGGACAATGAGTGAATCAATTCGCACAGAAAAGAAGCG
SEQ ID 29   (148) GATAATATGGAGTGGACAATGAGTGAATCAATCCGCACAGAAAAGAAGCG
SEQ ID 31   (148) GATAATATGGAGTGGACAATGAGTGAATCAATTCGCACAGAAAACAAACG
SEQ ID 33   (148) GATAATATGGAGTGGACAATGAGTGAATCAATTCCGCACAGAAAAGAAACG
SEQ ID 35   (148) GATAATATGGAGTGGACAATGAGTCAATCAATTCGCACAGAAAAGAAGCG
SEQ ID 37   (151) GATAATATGGAGTGGACAATGAGTGAATCGATTCGCACAGAAAAGAAGCG
SEQ ID 39   (148) GATAATATGGAGTGGACAATGAGTGAATCAATTCGCACAGAAAAGAAGCG
```

*FIG. 9A*

```
                     201                                                250
SEQ ID 17  (201)  TGAAATGAAAACAAATACGGTCGAGAATGAAGTTAAGAATCACGTAGATG
SEQ ID 19  (198)  TGAAATGAAATCAAATACAACCGGGAATGAAGTCAAGAATCACACCAATG
SEQ ID 21  (198)  TGAAATGAAATCAAATGCAACCGGGAATGAAGTCAAGATTCACACCAATG
SEQ ID 23  (198)  TGAAATGAAATCAAATGCAACCGGGAATGAAGTCAAGATTCACACCAATG
SEQ ID 25  (198)  TGAAATGAAATCAAATGCAACCGGGAATGAAGTCAAGAATCACACCAATG
SEQ ID 27  (198)  TGAAATGAAATCAAATGCAACCGGGAATGAAGTCAAGAATCACACGAATG
SEQ ID 29  (198)  TGAAATGAAATCAAATACAACCGGGAATGAAGTCAAGAATCACACCAATG
SEQ ID 31  (198)  TGAAATGAAATCAAATGCAACCGGGAATGAAGTCAAGAATCACACCAATG
SEQ ID 33  (198)  TGAAATGAAATCAAATGCAACCGGGAATGAAGTCAAGAATCACACCAATG
SEQ ID 35  (198)  TGAAATGAAATCAAATGCAACCGGGAATGAAGTCAAGATTCACACCAATG
SEQ ID 37  (201)  TGAAATGAAAACAAATACGGTCGAGAATGAAGTTAAGAATCACGTAGATG
SEQ ID 39  (198)  TGAAATGAAATCAAATGCAACCGGGAATGAAGTCAAGATTCACACCAATG
                     251                                       297
SEQ ID 17  (251)  ATGTAAATATATGTGGTACGTCTGGATTAGAGACGGAAGTTTGTCTA
SEQ ID 19  (248)  ATGTAAATGTATGTGATACGTCTGGATTAGAGACGGAGGTTTGTCTA
SEQ ID 21  (248)  ATGTAAATGTATGTGATACGTCTGGATTAGAGACGGAGGTTTGTCTA
SEQ ID 23  (248)  ATGTAAATGTATGTGATACGTCTGGATTAGAGACGGAGGTTTGTCTA
SEQ ID 25  (248)  ATGTAAATGTATGTGATACGTCTGGATTAGAGATGGAGGTTTGTCTA
SEQ ID 27  (248)  ATGTAAATGTATGTGATACGTCTGGATTAGAGACGGAGGTTTGTCTA
SEQ ID 29  (248)  ATGTAAATGTATGTGATACGTCTGGATTAGAGACGGAGGTTTGTCTA
SEQ ID 31  (248)  ATGTAAATGTATGTGATACGTCTGGATTAGAGACGGAGGTTTGTCTA
SEQ ID 33  (248)  ATGTAAATGTATGTGATACGTCTGGATTAGAGACGGAGGTTTGTCTA
SEQ ID 35  (248)  ATGTAAATGTATGTGATACGTCTGGATTAGAGACGGAGGTTTGTCTA
SEQ ID 37  (251)  ATGTAAATATATGTGATACGTCTGGATTAGAGACGGAAGTTTGTCTA
SEQ ID 39  (248)  ATGTAAATGTATGTGATACGTCTGGATTAGAGACGGAAGTTTGTCTA
```

| NSP4 Seqs | SEQ 17 | SEQ 19 | SEQ 21 | SEQ 23 | SEQ 25 | SEQ 27 | SEQ 29 | SEQ 31 | SEQ 33 | SEQ 35 | SEQ 37 | SEQ 39 |
|---|---|---|---|---|---|---|---|---|---|---|---|---|
| SEQ 17 |  | 89 | 88 | 89 | 88 | 89 | 88 | 89 | 89 | 89 | 100 | 90 |
| SEQ 19 |  |  | 99 | 99 | 99 | 99 | 99 | 99 | 99 | 99 | 89 | 98 |
| SEQ 21 |  |  |  | 100 | 99 | 99 | 99 | 99 | 99 | 100 | 89 | 98 |
| SEQ 23 |  |  |  |  | 99 | 99 | 99 | 99 | 99 | 100 | 89 | 99 |
| SEQ 25 |  |  |  |  |  | 99 | 99 | 99 | 99 | 99 | 89 | 98 |
| SEQ 27 |  |  |  |  |  |  | 99 | 99 | 99 | 99 | 89 | 98 |
| SEQ 29 |  |  |  |  |  |  |  | 99 | 99 | 99 | 89 | 98 |
| SEQ 31 |  |  |  |  |  |  |  |  | 100 | 99 | 89 | 98 |
| SEQ 33 |  |  |  |  |  |  |  |  |  | 99 | 89 | 98 |
| SEQ 35 |  |  |  |  |  |  |  |  |  |  | 89 | 99 |
| SEQ 37 |  |  |  |  |  |  |  |  |  |  |  | 90 |
| SEQ 39 |  |  |  |  |  |  |  |  |  |  |  |  |

*FIG. 9A (Continued)*

```
                    1                                                50
SEQ ID 18   (1)  ITSKTVIGKEKTENNISEQNDDIHKEYEEVMKQMRDMRVHVTALENSIHK
SEQ ID 20   (1)  ITSKTVISKEKTENDISEQNNDINKEYEEVMKQMREMRVHMTALENSIHK
SEQ ID 22   (1)  ITSKTVISKEKTENDISEQNNDINKEYEEVMKQMREMRVHMTALENSIHK
SEQ ID 24   (1)  ITSKTVISKEKTENDISEQNNDINKEYEEVMKQMREMRVHMTALENSIHK
SEQ ID 26   (1)  ITSKTVISKEKTENDISEQNNDINKEYEEVMKQMREMRVHMTALENSIHK
SEQ ID 28   (1)  ITSKTVISKEKTENDISEQNNDINKEYEEVMKQMREMRVHMTALENSIHK
SEQ ID 30   (1)  ITSKTVISKEKTENDISEQNNDINKEYEEVMKQMREMRVHMTALENSIHK
SEQ ID 32   (1)  ITSKTVISKEKTENDISEQNNDINKEYEEVMKQMREMRVHMTALENSIHK
SEQ ID 34   (1)  ITSKTVISKEKTENDISEQNNDINKEYEEVMKQMREMRVHMTALENSIHK
SEQ ID 36   (1)  ITSKTVISKEKTENDISEQNNDINKEYEEVMKQMREMRVHMTALENSIHK
SEQ ID 38   (1)  ITSKTVIGKEKTENNISEQNDDIHKEYEEVMKQMRDMRVHVTALENSIHK
SEQ ID 40   (1)  ITSKTVISKEKTENDISEQNNDINKEYEEVMKQMREMRVHMTALENSIHK
                   51                                           99
SEQ ID 18   (51) DNMEWRMSESIRREKKREMKTNTVENEVKNEVDVNIEGTSGLETEVCL
SEQ ID 20   (51) DNMEWRMSESIRREKKREMKSNTTGNEVKNETNDVNVCDTSGLETEVCL
SEQ ID 22   (51) DNMEWRMSESIRREKKREMKSNATGNEVKIETNDVNVCDTSGLETEVCL
SEQ ID 24   (51) DNMEWRMSESIRREKKREMKSNATGNEVKIETNDVNVCDTSGLETEVCL
SEQ ID 26   (51) DNMEWRMSESIRREKKREMKSNATGNEVKNETNDVNVCDTSGLEMEVCL
SEQ ID 28   (51) DNMEWRMSESIRREKKREMKSNATGNEVKNETNDVNVCDTSGLETEVCL
SEQ ID 30   (51) DNMEWRMSESIRREKKREMKSNATGNEVKNETNDVNVCDTSGLETEVCL
SEQ ID 32   (51) DNMEWRMSESIRREKKREMKSNATGNEVKNETNDVNVCDTSGLETEVCL
SEQ ID 34   (51) DNMEWRMSESIRREKKREMKSNATGNEVKNETNDVNVCDTSGLETEVCL
SEQ ID 36   (51) DNMEWRMSESIRREKKREMKSNATGNEVKIETNDVNVCDTSGLETEVCL
SEQ ID 38   (51) DNMEWRMSESIRREKKREMKTNTVENEVKNEVDVNICDTSGLETEVCL
SEQ ID 40   (51) DNMEWRMSESIRREKKREMKSNATGNEVKIETNDVNVCDTSGLETEVCL
```

| NSP4 Seqs | SEQ 18 | SEQ 20 | SEQ 22 | SEQ 24 | SEQ 26 | SEQ 28 | SEQ 30 | SEQ 32 | SEQ 34 | SEQ 36 | SEQ 38 | SEQ 40 |
|---|---|---|---|---|---|---|---|---|---|---|---|---|
| SEQ 18 | | 87 | 85 | 85 | 85 | 86 | 86 | 86 | 86 | 85 | 99 | 86 |
| SEQ 20 | | | 98 | 98 | 98 | 99 | 99 | 99 | 99 | 98 | 88 | 97 |
| SEQ 22 | | | | 100 | 98 | 99 | 99 | 99 | 99 | 100 | 86 | 99 |
| SEQ 24 | | | | | 98 | 99 | 99 | 99 | 99 | 100 | 86 | 99 |
| SEQ 26 | | | | | | 99 | 99 | 99 | 99 | 98 | 86 | 97 |
| SEQ 28 | | | | | | | 100 | 100 | 100 | 99 | 87 | 98 |
| SEQ 30 | | | | | | | | 100 | 100 | 99 | 87 | 98 |
| SEQ 32 | | | | | | | | | 100 | 99 | 87 | 98 |
| SEQ 34 | | | | | | | | | | 99 | 87 | 98 |
| SEQ 36 | | | | | | | | | | | 86 | 99 |
| SEQ 38 | | | | | | | | | | | | 87 |
| SEQ 40 | | | | | | | | | | | | |

*FIG. 9A (Continued)*

```
             1                                                50
SEQ ID 41   (1) AGGGCGTCCTCACTTTATCATCAATTAATTTCTCAGAATTATTATTCAAC
SEQ ID 43   (1) AGGGCGTCCTCACTTTATCAGCAATTAATTTCACAGAATTATTATTCAAC
SEQ ID 45   (1) AGGGCGTCCTCACTTTATCAGCAATTAATCTCACAGAATTATTATTCAAC
SEQ ID 47   (1) AGGGGCGTCCTCACTTTATCAGCAATTAATCTCACAGAATTATTATTCAAC
SEQ ID 49   (1) AGGGCGTCCTCACTTTATCAGCAATTAATCTCACAAAATTATTATTCAAC
             51                                               100
SEQ ID 41  (51) TGGGAATTAGATCTTAAAAGATTTACAAAACGACTAAAACTACTGTTGACT
SEQ ID 43  (51) TGGAAATGATATTTTACTGGATCAGCAAACAAATAACACAACTGTTGACT
SEQ ID 45  (51) TGGAAATGATATTTTACTGGATCAGCAAACAAATAACACAACTGTTGACT
SEQ ID 47  (51) TGGAAATGATATTTTACTGGATCAGCAAACAAATAACACAACTGTTGACT
SEQ ID 49  (51) TGGGAATNTATATTATTGGATCAGCAAACGAATAAAACAACTGTTGATT
            101                                               150
SEQ ID 41 (101) ATGTAGATGCTGGGAATTATACATATGCTCAATTGCCGCCAATGAAGTGG
SEQ ID 43 (101) ATATAGATATAGGAAATTATTCGTATACACAATTACCGCCGACATCATGG
SEQ ID 45 (101) ATATAGATATAGGAAATTACTCGTATACACAATTACCGCCGACATCATGG
SEQ ID 47 (101) ATATAGATATAGGAAATTATTCGTATACACAATTACCGCCGACATCATGG
SEQ ID 49 (101) ATGTAGATGTGCGGAAATTATTCATATACACAATTACCACCAACATCATGG
            151                                               200
SEQ ID 41 (151) GGAGCTGGAGCTACCTTCGAATCAGTCTTTAGCGGAGCTGAAATAACAGG
SEQ ID 43 (151) GGAGCAGGAATGACTTTTAAGTCTGCATTTAATGCAGAGGAAATTACAGG
SEQ ID 45 (151) GGAGCAGGAATGACTTTTAAGTCTGCATTTAATGCAGAGGAAATTACAGG
SEQ ID 47 (151) GGAGCAGGAATGACTTTTACGTCTGCATTTAATGCAGAGGAAATTACAGG
SEQ ID 49 (151) GGAGCAGGAATGACTTTTAAGTCTGCATTTAATGCAGAAGAAATGACGGG
            201                                               250
SEQ ID 41 (201) ACCGCACACAAATAGAGTTATAGAGTGGAAGAATTTACTAAATTCTGACC
SEQ ID 43 (201) ACCCAATACAGGT---GATATAGATTTGAATAATTTGACAAATGCGAATG
SEQ ID 45 (201) ACCCAATACGGGT---GATATAGATTTGAATAATTTGACAAATGCGAATG
SEQ ID 47 (201) ACCCAATACAGGT---GATATAGATTTGAATAATTTGACAAATGCGAATG
SEQ ID 49 (201) ACCTAACACAGGT---GATATAGATCTTAGTAAACTCACAACTGCGAATG
            251                                               300
SEQ ID 41 (251) AGTGGTTGCTGTTCCAAAACCAGCTGACACAGTTAAATTACTTAAACAT
SEQ ID 43 (248) GGTGGATATTGTATGACAAACCAACTGATACAAAACGATTGTTAAAACTA
SEQ ID 45 (248) GATGGATATTGTATGACAAACCAACTGATACAAAACGATTGTTAAAACTA
SEQ ID 47 (248) GGTGGATATTGTATGACAAACCAACTGATACAAAACGATTGTTAAAACTA
SEQ ID 49 (248) GATGGATATATATGAGAAGCCGACAATTAGCAAACGGTTATTAAAACTA
            301                                               350
SEQ ID 41 (301) GGACCTCAAACATATGATAGCACTTTAGCGGCATGTGAATTGTGGTATGG
SEQ ID 43 (298) GGAGCAGAAAGTTATGACAGTGTGTACGGCAGCATTCGAATTATGGTATGG
SEQ ID 45 (298) GGAGCAGAAAGTTATGACAGTGTGTACGGCAGCATTCGAATTATGGTATGG
SEQ ID 47 (298) GGAGCAGAAAGTTATGACAGTGTATACGGCAGCATTCGAATTATGGTATGG
SEQ ID 49 (298) GGGCCAGATGTTTACGATAGTGTTTATGCCGCATTTGAACTGTGGTATGG
            351                                               400
SEQ ID 41 (351) GAAGGTTAATACTATATGACATCAGAACACTATTCATCATTAAG-----
SEQ ID 43 (348) TAAAGCAAATACTGTAGTCACATCAATATACTATTCATCAGTGCAAAACT
SEQ ID 45 (348) TAAAGCAAATACTGTAGTCACATCAATATACTATTCATCAGTGCAAAACT
SEQ ID 47 (348) TAAAGCAAATACTGTAGTCACATCAATATACTATTCATCAGTGCAAAACT
SEQ ID 49 (348) TAAAGCAAATACAGTAGTTACATCAATATATTATGCATCAGCACAAAATT
            401                                               450
SEQ ID 41 (396) -TGATAATCAGTTGAATGTAAATGCCCATTCATTAGTATTATTTTGGAA
SEQ ID 43 (398) CTGAAAACACTGTAACAGTACAACATGACTCATTAGTGTTATTCTTTAA
SEQ ID 45 (398) CTGAAAACACTGTAACAGTACAGCATGACTCATTAGTGTTATTCTTTAA
SEQ ID 47 (398) CTGAAAACACTGTAACAGTACAGCATGACTCATTAGTGTTATTCTTTAA
SEQ ID 49 (398) CTGAGAATACTGTAACATTACAGTATGACTCATTAGTACTATTTTTCAA
```

*FIG. 9B*

| VP4 Seqs | SEQ 41 | SEQ 43 | SEQ 45 | SEQ 47 | SEQ 49 |
|---|---|---|---|---|---|
| SEQ 41 | | 69 | 69 | 69 | 67 |
| SEQ 43 | | | 99 | 99 | 86 |
| SEQ 45 | | | | 99 | 86 |
| SEQ 47 | | | | | 86 |
| SEQ 49 | | | | | |

*FIG. 9B (Continued)*

```
                    1                                                  50
SEQ ID 42   (1)    RASSLHQLISQNYYSGNEILKDLQTKITVDYVDAGNYTYAQIPYKN
SEQ ID 44   (1)    RASSLQQLISQNYYSGNDILLDQQTNNTIVDYIDIGNYSTTQLPISN
SEQ ID 46   (1)    RASSLQQLISQNYYSGNDILLDQQTNNTIVDYIDIGNYSTTQLPISN
SEQ ID 48   (1)    RASSLQQLISQNYYSGNDILLDQQTNNTIVDYIDIGNYSTTQLPISN
SEQ ID 50   (1)    RASSLQQLISQNYYSGNXILLDQQTNKTIVDYVDVGNYSTTQLPISN
                    51                                                 100
SEQ ID 42   (51)   GAGATESVTSAAEITGPHNRVIEWKMLLNSDQWLLFPKPADTVKLLH
SEQ ID 44   (51)   GAGMTEKSAENAERITGPNTG-DIDLNMLTNANGNILYDKPTDIKRLLKL
SEQ ID 46   (51)   GAGMTEKSAENAERITGPNTG-DIDLNMLTNANGNILYDKPTDIKRLLKL
SEQ ID 48   (51)   GAGMTETSAENAERITGPNTG-DIDLNMLTNANGNILYDKPTDIKRLLKL
SEQ ID 50   (51)   GAGMTEKSAENAEBMTGPNTG-DIDLSNLTTANGNILYEKPTIKRLLKL
                    101                                                150
SEQ ID 42   (101)  GRQTYDSTLAACFLWYGKANTIVSEHHSSLS--DNQWNVNADIVLLWN
SEQ ID 44   (100)  GRESYDSVYAAFFLWYGKANTVTSIYSSVQNSENTVTVQHDSIVLLFN
SEQ ID 46   (100)  GRESYDSVYAAFFLWYGKANTVTSIYSSVQNSENTVTVQHDSIVLLFN
SEQ ID 48   (100)  GRESYDSVYAAFFLWYGKANTVTSIYSSVQNSENTVTVQHDSIVLLFN
SEQ ID 50   (100)  GRDVYDSVYAAFFLWYGKANTVTSIYSAQNSENTVTLQYDSIVLLFN
                    151                                                200
SEQ ID 42   (149)  AGGTFDKQIVNFAWDMGGIIKESSQQPRLDIYMANMNNENSDNFNWEE
SEQ ID 44   (150)  VGYGLTKQIVKENWNMGGILVRETADG-RVDICMADMNDFNSDNFNWES
SEQ ID 46   (150)  VGYGLTKQIVKENWNMGGILVRETTDG-RVDICMADMNDFSSDNFNWES
SEQ ID 48   (150)  VGYGLTKQIVKENWNMGGILVRETTDG-RVDICMADMNDFNSDNFNWES
SEQ ID 50   (150)  VGYGLTKQIVRENWDMGGILVRETADG-RVDICMADMNDFSSDNFNWEK
                    201                                     249
SEQ ID 42   (199)  NRFTIRKNATINISTDYYAGSSDYNQLKELQQSLITTFMRMKV---
SEQ ID 44   (199)  NKRSFRKS---NINMITEYYLANVDPYNQLKILNQLTAKNVEIRMMKAIK
SEQ ID 46   (199)  NKRSFRKS---NINMITEYYLANVDPYNQLKILNQLTAKNVEIRMMKAIK
SEQ ID 48   (199)  NKRSFRKS---NINMITEYYLANVDPYNQLKILNQLTAKNVEIRMMKAIK
SEQ ID 50   (199)  NTRSFRKS---NINMIAEYYLANVDPYSQLKALNXLIXXNIEIRMMKSIX
```

| VP4 Seqs | SEQ 42 | SEQ 44 | SEQ 46 | SEQ 48 | SEQ 50 |
|---|---|---|---|---|---|
| SEQ 42 |  | 64 | 64 | 64 | 62 |
| SEQ 44 |  |  | 99 | 99 | 88 |
| SEQ 46 |  |  |  | 99 | 88 |
| SEQ 48 |  |  |  |  | 87 |
| SEQ 50 |  |  |  |  |  |

```
            1001                                              1050
SEQ ID 51  (1001) GCGATTCACACTGTGTGAATTATTCAATTGTTTGCAAACGTTACAAGAGAC
SEQ ID 53  (1001) GTGATTCACATTCAGTAGATTATTCAATCGTCGCAAATGCCAGAACAGAC
SEQ ID 55  (1001) GTGATTCACATTCAGTAGATTATTCAATCGTCGCAAATGCCAGAACAGAC
SEQ ID 57  (1001) GCGATTCACACTGTGTAGACTATTCAATTGTTTGCAAACATTAGAAGAGAC
SEQ ID 59  (1001) GTGATTCACATTCAGTAGATTATTCAATCGTCGCAAATGCCAGAACAGAC
SEQ ID 61  (1001) GTGATTCACATTCAGTAGATTATTCAATCGTCGCAAATGCCAGAACAGAC
SEQ ID 63  (1001) GTGATTCACATTCAGTAGATTATTCAATCGTCGCAAATGCCAGAACAGAC
SEQ ID 65  (1001) GTGATTCACATTCAGTAGATTATTCAATCGTCGCAAATGCCAGAACAGAC
SEQ ID 67  (1001) GTGATTCACATTCAGTAGATTATTCAATCGTCGCAAATGCCAGAACAGAC
SEQ ID 69  (1001) GTGATTCACATTCAGTAGATTATTCAATCGTCGCAAATGCCAGAACAGAC
SEQ ID 71  (1001) GTGATTCACATTCAGTAGATTATTCAATCGTCGCAAATGCCAGAACAGAC
            1051                                              1100
SEQ ID 51  (1051) TCAGCAATGCCAGCTGGAACAGTATTTCAACCAGGATTCCATGGGAACA
SEQ ID 53  (1051) TCAGCAATGCCAGCTGGAACAGTATTTCAACCAGGATTCCATGGGAACA
SEQ ID 55  (1051) TCAGCAATGCCAGCTGGAACAGTATTTCAACCAGGATTCCATGGGAACA
SEQ ID 57  (1051) TCAGCAATGCCAGCTGAACAGTATTCAACCAGGATTCCATGGGAACA
SEQ ID 59  (1051) TCAGCAATGCCAGCTGGAACAGTATTTCAACCAGGCTTCCATGGGAACA
SEQ ID 61  (1051) TCAGCAATGCCAGCTGGAACAGTATTTCAACCAGGCTTCCATGGGAACA
SEQ ID 63  (1051) TCAGCAATGCCAGCTGGAACAGTATTTCAACCAGGATTCCATGGGAACA
SEQ ID 65  (1051) TCAGCAATGCCAGCTGGAACAGTATTTCAACCAGGATTCCATGGGAACA
SEQ ID 67  (1051) TCAGCAATGCCAGCTGGAACAGTATTTCAACCAGGATTCCATGGGAACA
SEQ ID 69  (1051) TCAGCAATGCCAGCTGGAACAGTATTTCAACCAGGCTTCCATGGGAACA
SEQ ID 71  (1051) TCAGCAATGCCAGCTGGAACAGTATTTCAACCAGGCTTCCATGGGAACA
            1101                                              1150
SEQ ID 51  (1101) GACATTATCCAACTACACTGTTGCTCAGGAGGATAATTTAGAAGACTTT
SEQ ID 53  (1101) GATATTATCCAACTACACTGTTGCTCAGGAGGATAATTTAGAAAGACTTT
SEQ ID 55  (1101) GATATTATCCAACTACACTGTTGCTCAGGAGGATAATTTAGAAAGACTTT
SEQ ID 57  (1101) GACATTATCCAACTACACTGTTGCTCAGGAGGATAATTTAGAAAGACTTC
SEQ ID 59  (1101) GATATTATCCAACTACACTGTTGCTCAGGAGGATAATTTAGAAGCACTTT
SEQ ID 61  (1101) GATATTATCCAACTACACTGTTGCTCAGGAGGATAATTTAGAAAGACTTT
SEQ ID 63  (1101) GATATTATCCAACTACACTGTTGCTCAGGAGGATAATTTAGAAAGACTTT
SEQ ID 65  (1101) GATATTATCCAACTACACTGTTGCTCAGGAGGATAATTTAGAAAGACTTT
SEQ ID 67  (1101) GATATTATCCAACTACACTGTTGCTCAGGAGGATAATTTAGAAAGACTTT
SEQ ID 69  (1101) GATATTATCCAACTACACTGTTGCTCAGGAGGATAATTTAGAAAGACTTT
SEQ ID 71  (1101) GATATTATCCAACTACACTGTTGCTCAGGAGGATAATTTAGAAAGACTTT
            1151                    1182
SEQ ID 51  (1151) TACTAGTTGCGTCCTGGAAGAGAATGGTGATG
SEQ ID 53  (1151) TGTTAGTTGCGTCTGTGAAGAGAATGGTGATG
SEQ ID 55  (1151) TGTTAGTTGCGTCTGTGAAGAGAATGGTGATG
SEQ ID 57  (1151) TACTAGTTGCGTCCTGGAAGAGAATGGTGATG
SEQ ID 59  (1151) TGTTAGTTGCGTCTGTGAAGAGAATGGTGATG
SEQ ID 61  (1151) TGTTAGTTGCGTCTGTGAAGAGAATGGTGATG
SEQ ID 63  (1151) TGTTAGTTGCGTCTGTGAAGAGAATGGTGATG
SEQ ID 65  (1151) TGTTAGTTGCGTCTGTGAAGAGAATGGTGATG
SEQ ID 67  (1151) TGTTAGTTGCGTCTGTGAAGAGAATGGTGATG
SEQ ID 69  (1151) TGTTAGTTGCGTCTGTGAAGAGAATGGTGATG
SEQ ID 71  (1151) TGTTAGTTGCGTCTGTGAAGAGAATGGTGATG
```

|        | SEQ 51 | SEQ 53 | SEQ 55 | SEQ 57 | SEQ 59 | SEQ 61 | SEQ 63 | SEQ 65 | SEQ 67 | SEQ 69 | SEQ 71 |
|--------|--------|--------|--------|--------|--------|--------|--------|--------|--------|--------|--------|
| SEQ 51 |        | 86     | 86     | 92     | 86     | 85     | 85     | 85     | 86     | 86     | 86     |
| SEQ 53 |        |        | 100    | 87     | 99     | 99     | 100    | 100    | 99     | 99     | 99     |
| SEQ 55 |        |        |        | 87     | 99     | 99     | 100    | 100    | 99     | 99     | 99     |
| SEQ 57 |        |        |        |        | 87     | 86     | 86     | 86     | 87     | 87     | 87     |
| SEQ 59 |        |        |        |        |        | 99     | 98     | 99     | 99     | 99     | 99     |
| SEQ 61 |        |        |        |        |        |        | 98     | 99     | 98     | 98     | 98     |
| SEQ 63 |        |        |        |        |        |        |        | 100    | 99     | 99     | 99     |
| SEQ 65 |        |        |        |        |        |        |        |        | 99     | 99     | 99     |
| SEQ 67 |        |        |        |        |        |        |        |        |        | 99     | 99     |
| SEQ 69 |        |        |        |        |        |        |        |        |        |        | 100    |
| SEQ 71 |        |        |        |        |        |        |        |        |        |        |        |

```
         251                                                   300
SEQ ID 52  (251) VQVMKGTFSIEFYKNGQLVDMIRNMGVTVRIFDSIRITISVIRPAAMTG
SEQ ID 54  (251) VQIMKGTFTIEFYKNGQLVDLIRNMGVTVRIRDTIRITISMIRPATMTG
SEQ ID 56  (251) VQIMKGTFTIEFYKNGQLVDLIRNMGVTVRIRDTIRITISMIRPAAMTG
SEQ ID 58  (251) VQVMKGTFTIEFYKNGQLVDMIRNMGVTVRIRDSIRITISMIRPAAMTG
SEQ ID 60  (251) VQIMKGTFTIEFYKNGQLVDLIRNMGVTVRIRDTIRITISMIRPAAMTG
SEQ ID 62  (251) VQIMKGTFTIEFYKNGQLVDLIRNMGVTVRIRDTIRITISMIRPAAMTG
SEQ ID 64  (251) VQIMKGTFTIEFYKNGQLVDLIRNMGVTVRIRDTIRITISMIRPATMTG
SEQ ID 66  (251) VQIMKGTFTIEFYKNGQLVDLIRNMGVTVRIRDTIRITISMIRPATMTG
SEQ ID 68  (251) VQIMKGTFTIEFYKNGQLVDLIRNMGVTVRIRDTIRITISMIRPAAMTG
SEQ ID 70  (251) VQIMKGTFTIEFYKNGQLVDLIRNMGVTVRIRDTIRITISMIRPAAMTG
SEQ ID 72  (251) VQIMKGTFTIEFYKNGQLVDLIRNMGVTVRIRDTIRITISMIRPAAMTG
         301                                                   350
SEQ ID 52  (301) YVQRIFPQGGPYQHAAYMLTLSVLDATTESVLDSHSVDYSIVANVRRI
SEQ ID 54  (301) YVQRLFPQGGPYQHAAYMITLSILDATTESVMDSHSVDYSIVANVRRI
SEQ ID 56  (301) YVQRLFPQGGPYQHAAYMITLSLLDATTESVMDSHSVDYSIVANIRRI
SEQ ID 58  (301) YVQRIFPQGGPYQAAYMLTLSVLDATTESVLDSHSVDYSIVANVRRI
SEQ ID 60  (301) YVQRLFPQGGPYQHAAYMITLSILDATTESVMDSHSVDYSIVANVRRI
SEQ ID 62  (301) YVQRLFPQGGPYQHAAYMITLSILDATTESVMDSHSVDYSIVANVRRI
SEQ ID 64  (301) YVQRLFPQGGPYQHAAYMITLSILDATTESVMDSHSVDYSIVANVRRI
SEQ ID 66  (301) YVQRLFPQGGPYQHAAYMITLSILDATTESVMDSHSVDYSIVANVRRI
SEQ ID 68  (301) YVQRLFPQGGPYQHAAYMITLSILDATTESVMDSHSVDYSIVANVRRI
SEQ ID 70  (301) YVQRLFPQGGPYQHAAYMITLSILDATTESVMDSHSVDYSIVANVRRI
SEQ ID 72  (301) YVQRLFPQGGPYQHAAYMITLSILDATTESVMDSHSVDYSIVANVRRI
         351                                          394
SEQ ID 52  (351) SAMPAGTVFQPGFPWEQTLSNYTVAQEDNLERLLVASVKRMVM
SEQ ID 54  (351) SAMPAGTVFQPGFPWEQILSNYTVAQEDNLERLLVASVKRMVM
SEQ ID 56  (351) SAMPAGTVFQPGFPWEQILSNYTVAQEDNLERLLVASVKRMVM
SEQ ID 58  (351) SAMPAGTVFQPGFPWEQTLSNYTVAQEDNLERLLVASVKRMVM
SEQ ID 60  (351) SAMPAGTVFQPGFPWEQILSNYTVAQEDNLERLLVASVKRMVM
SEQ ID 62  (351) SAMPAGTVFQPGFPWEQILSNYTVAQEDNLERLLVASVKRMVM
SEQ ID 64  (351) SAMPAGTVFQPGFPWEQILSNYTVAQEDNLERLLVASVKRMVM
SEQ ID 66  (351) SAMPAGTVFQPGFPWEQILSNYTVAQEDNLERLLVASVKRMVM
SEQ ID 68  (351) SAMPAGTVFQPGFPWEQILSNYTVAQEDNLERLLVASVKRMVM
SEQ ID 70  (351) SAMPAGTVFQPGFPWEQILSNYTVAQEDNLERLLVASVKRMVM
SEQ ID 72  (351) SAMPAGTVFQPGFPWEQILSNYTVAQEDNLERLLVASVKRMVM
```

|        | SEQ 52 | SEQ 54 | SEQ 56 | SEQ 58 | SEQ 60 | SEQ 62 | SEQ 64 | SEQ 66 | SEQ 68 | SEQ 70 | SEQ 72 |
|--------|--------|--------|--------|--------|--------|--------|--------|--------|--------|--------|--------|
| SEQ 52 |        | 91     | 91     | 96     | 91     | 91     | 91     | 91     | 91     | 91     | 91     |
| SEQ 54 |        |        | 100    | 93     | 100    | 99     | 100    | 100    | 99     | 100    | 100    |
| SEQ 56 |        |        |        | 93     | 100    | 99     | 100    | 100    | 100    | 100    | 100    |
| SEQ 58 |        |        |        |        | 93     | 93     | 93     | 93     | 93     | 93     | 93     |
| SEQ 60 |        |        |        |        |        | 99     | 100    | 100    | 100    | 100    | 100    |
| SEQ 62 |        |        |        |        |        |        | 99     | 99     | 99     | 99     | 99     |
| SEQ 64 |        |        |        |        |        |        |        | 100    | 99     | 100    | 100    |
| SEQ 66 |        |        |        |        |        |        |        |        | 99     | 100    | 100    |
| SEQ 68 |        |        |        |        |        |        |        |        |        | 100    | 100    |
| SEQ 70 |        |        |        |        |        |        |        |        |        |        | 100    |
| SEQ 72 |        |        |        |        |        |        |        |        |        |        |        |

*FIG. 9C (Continued)*

ROTAVIRUS SUBUNIT VACCINES AND METHODS OF MAKING AND USE THEREOF

This application claims priority to U.S. provisional patent application Ser. No. 61/598,624, filed on Feb. 14, 2012, and herein incorporated by reference in its entirety.

FIELD OF THE INVENTION

The present invention relates generally to subunit vaccines, particularly those comprising rotavirus peptides that have been engineered to be genetically and antigenically nearly identical to those expressed by viruses infecting a target population of animals. Plasmids expressing antigenic peptides or subunit protein(s) are maintained in the bacterial cell population by way of toxin/antidote selection system. The bacterial cells produce a toxic protein, which is counteracted by antidote protein encoded by the plasmid carrying the peptides, rendering non-transformed cells non-viable.

BACKGROUND

Rotavirus is the most common cause of severe diarrhea among infants and young children (Dennehy P H, 2000), and is one of several viruses that cause infections often called stomach flu, despite having no relation to influenza. It is a genus of double-stranded RNA virus in the family Reoviridae. There are five species of this virus, referred to as A, B, C, D, and E (ICTV Virus Taxonomy: 2009 Release). Table 1 provides a summary of known rotaviral proteins. Rotavirus A, the most common, causes more than 90% of infections in humans. The virus is transmitted by the fecal-oral route, and infects and damages the cells that line the small intestine and causes gastroenteritis. In addition to its impact on human health, rotavirus also infects animals, and is a pathogen of livestock (Dubovi E J, 2010).

For example, according to a recent study, rotavirus was commonly found (65%) in the feces or intestinal contents from pigs with diarrhea. The majority of animals were infected by single group (A, B, C) although concurrent infection by more than one rotavirus group does occur (Yoon, K J, Epidemiology of rotaviruses, ISUVDL submissions, 2010-2011, Iowa State). Nearly one-third of animals were infected by at least Group C Rotavirus. Until now, prevention of rotavirus in porcines had involved rather arcane practices, such as feeding infected piglet tissue to healthy pigs. This practice was necessitated because Group C rotavirus cannot be grown in vitro, thus preventing the production of conventional inactivated/attenuated whole-virus vaccines. Thus, there is a clear and urgent need for safer and more effective preventative measures.

TABLE 1

Rotavirus protein summary

| RNA Segment (Gene) | Size (bp, based on Human Rota C strain) | Protein | Molecular weight kDa | Location | Copies per particle | Function |
| --- | --- | --- | --- | --- | --- | --- |
| 1 | 3309 | VP1 | 125 | At the vertices of the core | <25 | RNA-dependent RNA polymerase |
| 2 | 2736 | VP2 | 102 | Forms inner shell of the core | 120 | Stimulates viral RNA replicase |
| 3 | 2283 | VP3 | 88 | At the vertices of the core | <25 | Guanylyl transferase mRNA capping enzyme |
| 4 | 2166 | VP4 | 87 | Surface spike | 120 | Cell attachment, virulence |
| 5 | 1353 | NSP1 | 59 | Nonstructural | 0 | 5'RNA binding |
| 6 | 1350 | VP6 | 45 | Inner Capsid | 780 | Structural and species-specific antigen |
| 7 | 1270 | NSP3 | 37 | Nonstructural | 0 | Enhances viral mRNA activity and shut-offs cellular protein synthesis |
| 8 | 1063 | NSP2 | 35 | Nonstructural | 0 | NTPase involved in RNA packaging |
| 9 | 1037 | VP7, VP7 | 38, 34 | Surface | 780 | Structural and neutralization antigen |
| 10 | 730 | NSP4 | 20 | Nonstructural | 0 | Enterotoxin |
| 11 | 613 | NSP5 NSP6 | 22 | Nonstructural | 0 | ssRNA and dsRNA binding modulator of NSP2 |

An alternate approach would be to produce vaccines comprising immunogenic rotavirus subunit proteins or antigens. At time of filing this disclosure, inventors are aware of no references describing methods of producing rotavirus subunit vaccines (autogenous or otherwise) to immunize porcines against rotavirus, particular the Group C variety. The following patents and applications summarize relevant rotavirus prior art, with emphasis on subunit-based vaccines.

U.S. Pat. No. 7,790,178 (to Intervet) describes trivalent vaccines, which includes inactivated canine rotavirus.

U.S. Pat. No. 7,311,918 & U.S. Pat. No. 6,589,529 (to Children's Hospital Ohio) describe a recombinant rotavirus fusion protein comprising a VP6 protein fragment, intended for vaccinating humans. Mouse data indicated the vaccine generated an immune response directed against the VP6 fusion protein.

U.S. Pat. No. 6,867,353 (to Exploregen) generally describes expression of a cDNA fragment encoding human rotavirus structural protein using transformed tomato.

U.S. Pat. No. 6,716,431 (to Wyeth, now Pfizer) describes alternate forms of NSP4 (i.e. SNPs resulting in amino acid changes), which still retain antigenicity, but exhibit reduced cytotoxicity.

U.S. Pat. No. 6,673,355 & U.S. Pat. No. 6,210,682 (to Baylor College of Medicine) relate to use of NSP4 and fragments thereof (NSP4 114-135, NSP4 120-147, NSP4 112-174, or NSP4 112-150) as a prevention and/or treatment of rotaviral disease. Compositions including an enterotoxin adjuvant are also described. U.S. Pat. No. 5,891,676 & U.S. Pat. No. 5,827,696 (also to Baylor) describe baculoviral expression of rotavirus VP2 and VP7, respectively.

U.S. Pat. No. 6,187,319 (to University of Mass.) generally relates to methods for producing immune responses in animals against a first rotavirus by administering an isolated VP6 polypeptide of a second rotavirus that infects a different species than the animal to be vaccinated.

U.S. Pat. No. 5,298,244 (to University of Saskatchewan) describes assembled viral particles having VP4, VP6, and VP7.

US20110171316 (to US Health and Human Service) describes a recombinant human rotavirus group C virus-like particles.

US20100047763 (to Goes et al.) discloses plasmid DNA encoding rotavirus proteins for use in diagnostic kits.

U.S. Pat. No. 5,186,933 (to Baylor College of Medicine) discloses expression of rotavirus genes, particularly VP3 and VP7) using a baculovirus system.

Until their present disclosure, inventors are aware of no effective porcine rotavirus subunit vaccine prepared by expressing rotavirus type C antigens in *E. coli*. Further, no methods for producing safe and effective vaccines for porcines have been disclosed, and thus it is an object of the instant disclosure to provide such vaccines.

REFERENCES

Dennehy P H (2000). "Transmission of rotavirus and other enteric pathogens in the home". Pediatr. Infect. Dis. J. 19 (10 Suppl): S103-5. doi:10.1097/00006454-200010001-00003. PMID 11052397.

Bernstein D I (March 2009). "Rotavirus overview". The Pediatric Infectious Disease Journal 28 (3 Suppl): S50-3.

Grimwood K, Lambert S B (February 2009). "Rotavirus vaccines: opportunities and challenges". Human Vaccines 5 (2): 57-69. PMID 18838873.

Bishop R (October 2009). "Discovery of rotavirus: Implications for child health". Journal of Gastroenterology and Hepatology 24 Suppl 3: S81-5.

Rheingans R D, Heylen J, Giaquinto C (2006). "Economics of rotavirus gastroenteritis and vaccination in Europe: what makes sense?". Pediatr. Infect. Dis. J. 25 (1 Suppl): S48-55.

Simpson E, Wittet S, Bonilla J, Gamazina K, Cooley L, Winkler J L (2007). "Use of formative research in developing a knowledge translation approach to rotavirus vaccine introduction in developing countries". BMC Public Health 7: 281.

Edward J Dubovi; Nigel James MacLachlan (2010). Fenner's Veterinary Virology, Fourth Edition. Boston: Academic Press. p. 288. ISBN 0-12-375158-6.

SUMMARY OF THE INVENTION

An object of this invention is to provide subunit vaccines as well as methods for treatment and prophylaxis of infection by rotavirus.

The present invention further relates to a new vector and to the use thereof for the production of a heterologous protein or of a gene of interest that can be used, for example, in the context of an immunization. In particular embodiments, the heterologous protein is a rotavirus protein. In more particular embodiments, the protein is a porcine rotavirus protein selected from NSP4, VP4, or VP6. In another embodiment, the rotavirus protein is a NSP4-VP4-VP6 triple fusion protein.

Another objective of the present invention is to provide a new vector which can be used on an industrial scale, which has the advantage of producing a high expression yield, this being the case in the absence of any use of antibiotics, and which can therefore be used for small or large scale volumes (for example, 1-10,000 liter cultures).

The present invention therefore provides a self-replicating vector devoid of any antibiotic-resistance gene, comprising: (a) a sequence encoding the ccdA protein functionally linked to a first promoter; and (b) a heterologous sequence functionally linked to a second promoter. According to one particular embodiment, the first promoter is a constitutive promoter. According to another embodiment, the second promoter is an inducible promoter, in particular the second promoter is the T7 promoter. In another embodiment the promoter is the T5 promoter.

According to one particular embodiment, the heterologous sequence encodes a vaccine antigen.

According to another aspect, the present invention relates to a prokaryotic cell expressing the ccdB protein, comprising a vector as defined above.

According to one particular aspect, said prokaryotic cell is an *E. coli* cell.

According to another aspect, the present invention relates to a method for producing a heterologous protein, comprising the steps of:

(a) inoculating an appropriate culture medium with prokaryotic cells expressing the ccdB protein and containing a vector as defined above;

(b) fermenter culturing the cell thus transformed in the absence of antibiotic; and (c) recovering the heterologous protein produced during step (b) from the supernatant or from the cell pellet.

According to one particular embodiment, the present invention relates to a method for producing recombinant rotavirus peptides.

According to another aspect, the present invention relates to a method for producing a self-replicating vector as defined above, comprising the steps of:

(a) inoculating an appropriate culture medium with prokaryotic cells expressing the ccdB protein and containing a vector as defined above;

(b) fermenter culturing the cell thus transformed in the absence of antibiotic; and (c) recovering the vector produced during step (b).

According to another aspect, the present invention relates to a method for constructing a self-replicating vector as defined above, comprising the steps of:

(a) beginning with a self-replicating vector comprising a functional antibiotic-resistance gene and a ccdA gene;

(b) performing inverse PCR to amplify the non-antibiotic resistance gene plasmid sequence;

(c) phosphorylating and ligating the PCR product to produce the antibiotic resistance gene-free version of the vector recited in (a);

(d) transforming a prokaryotic cell expressing the ccdB protein; and (e) recovering the prokaryotic cells comprising the self-replicating vector.

According to another aspect, biological samples are taken from populations of production animals, including porcines. RNA is harvested therefrom, and reverse transcription is performed, using rotavirus gene-specific primers. The PCR products are then cloned into the self-replicating plasmid defined above, and the new plasmids containing the herd and or region-specific rotavirus genes are transformed into prokaryotic cells expressing ccdB. Rotavirus peptides are harvested from the cells and formulated into the inventive autogenous and/or commercial vaccines.

In a particular embodiment, the autogenous rotavirus subunit vaccines comprise an adjuvant. The adjuvant may be an oil, emulsion, a metal salt (e.g. Al(OH)$_3$), or combinations thereof. In an embodiment, the adjuvant is TRIGEN® or ULTRAGEN® or PrimaVant® (TRIGEN+Quil A), TS6 (described in U.S. Pat. No. 7,371,395 US to Merial), LR4 (described in U.S. Pat. No. 7,691,368, to Merial), or any formulation described in US 2011-0129494 A1 (to Merial).

In an embodiment, the vaccine may comprise a mixture of rotavirus VP4, VP6, and NSP4, and a preserving amount of formaldehyde and/or antimicrobial agents.

The invention further provides methods for inducing an immunological (or immunogenic) or protective response against rotavirus, as well as methods for preventing or treating rotavirus or disease state(s) caused by rotavirus, comprising administering the subunits, or a composition comprising the subunits.

The invention also relates to expression products from the plasmid as well as antibodies generated from the expression products or the expression thereof uses for such products and antibodies, e.g., in diagnostic applications.

Kits comprising at least one rotavirus polypeptide or fragment or variant thereof and instructions for use are also provided.

These and other embodiments are disclosed or are obvious from and encompassed by, the following Detailed Description.

BRIEF DESCRIPTION OF DRAWINGS

A full and enabling disclosure of the present invention, including the best mode thereof, to one of ordinary skill in the art, is set forth more particularly in the remainder of the specification, including reference to the accompanying figures, wherein:

Figure 9B:
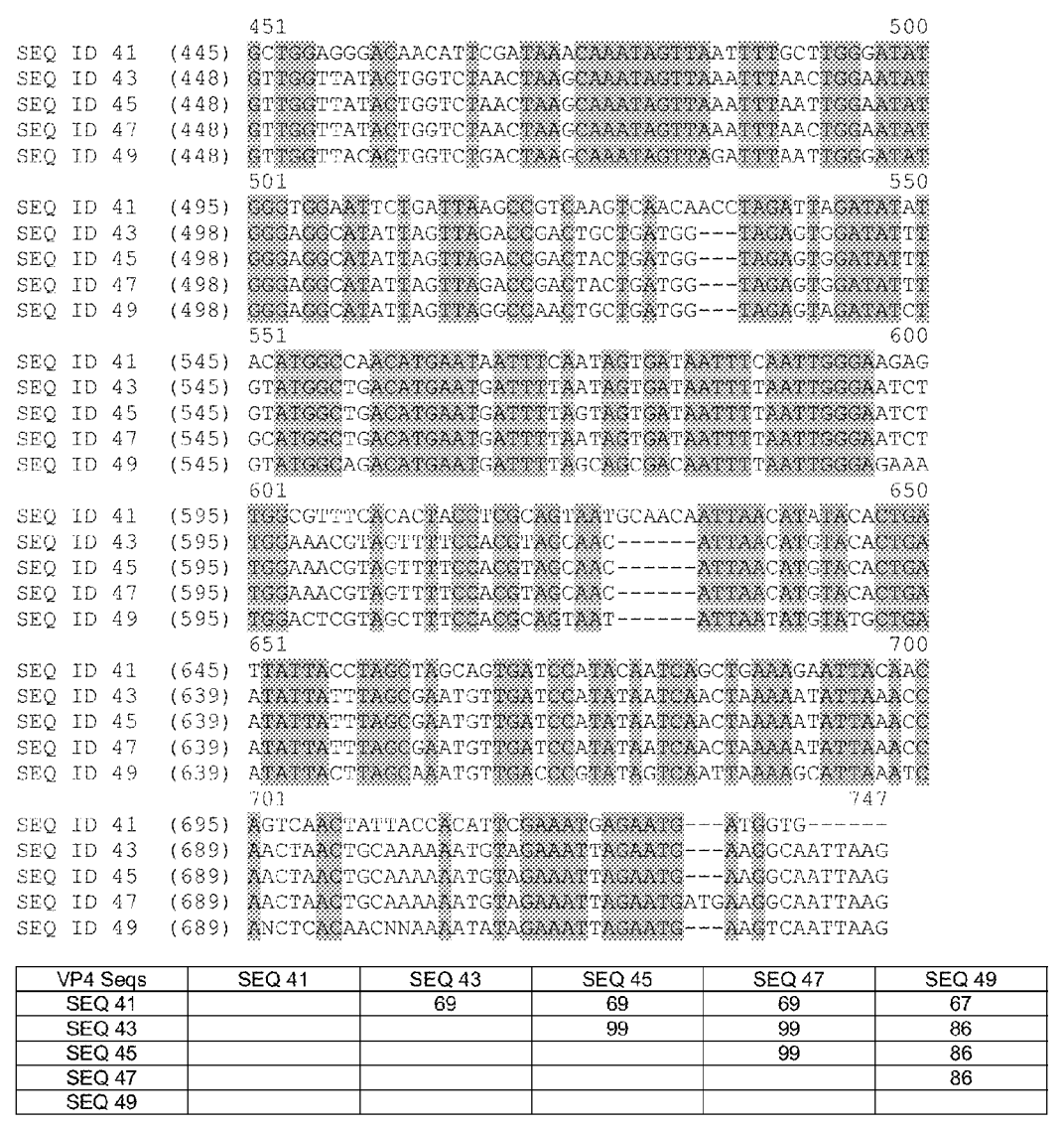
Figure 9C:
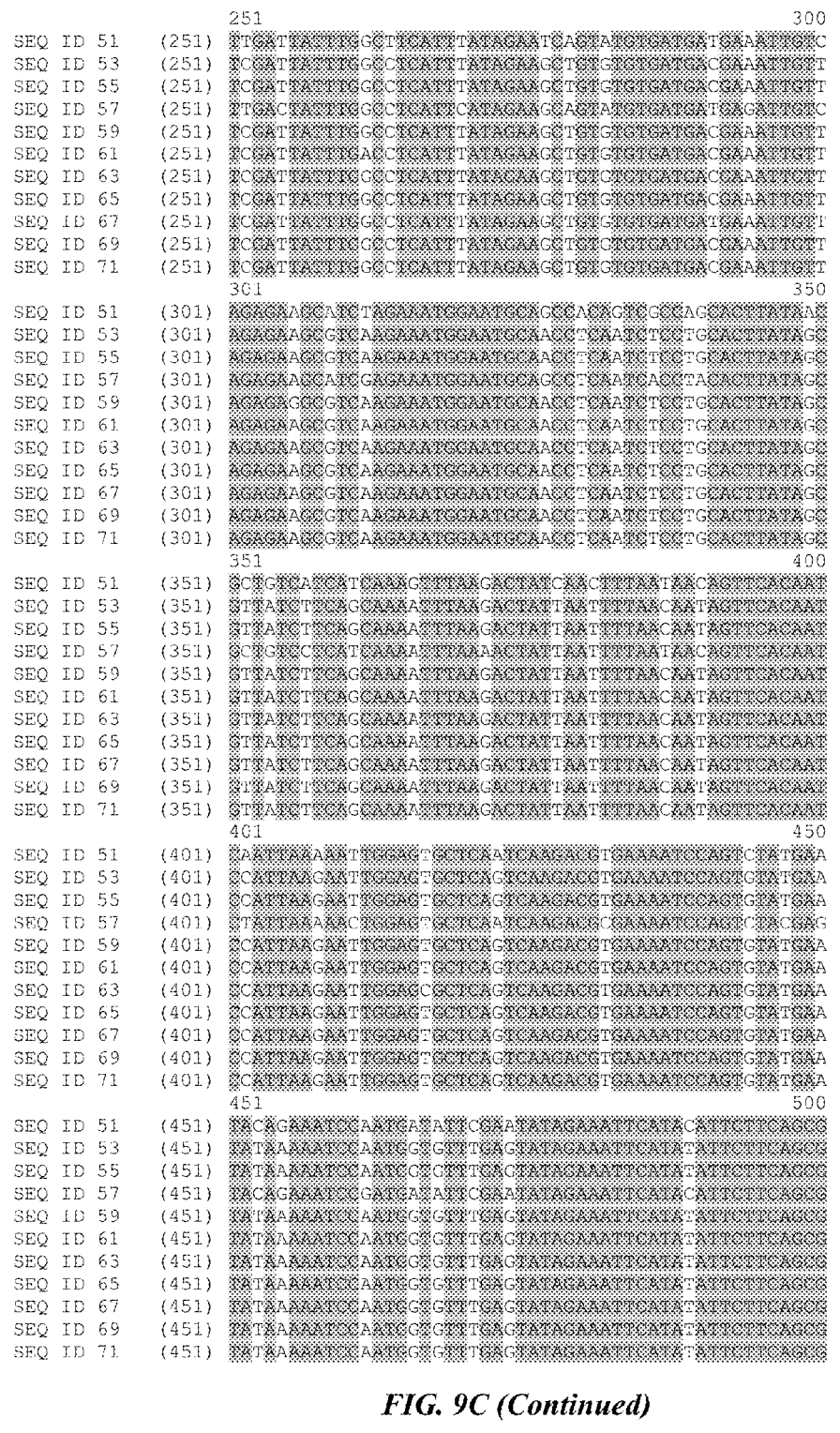
Figure 9C:
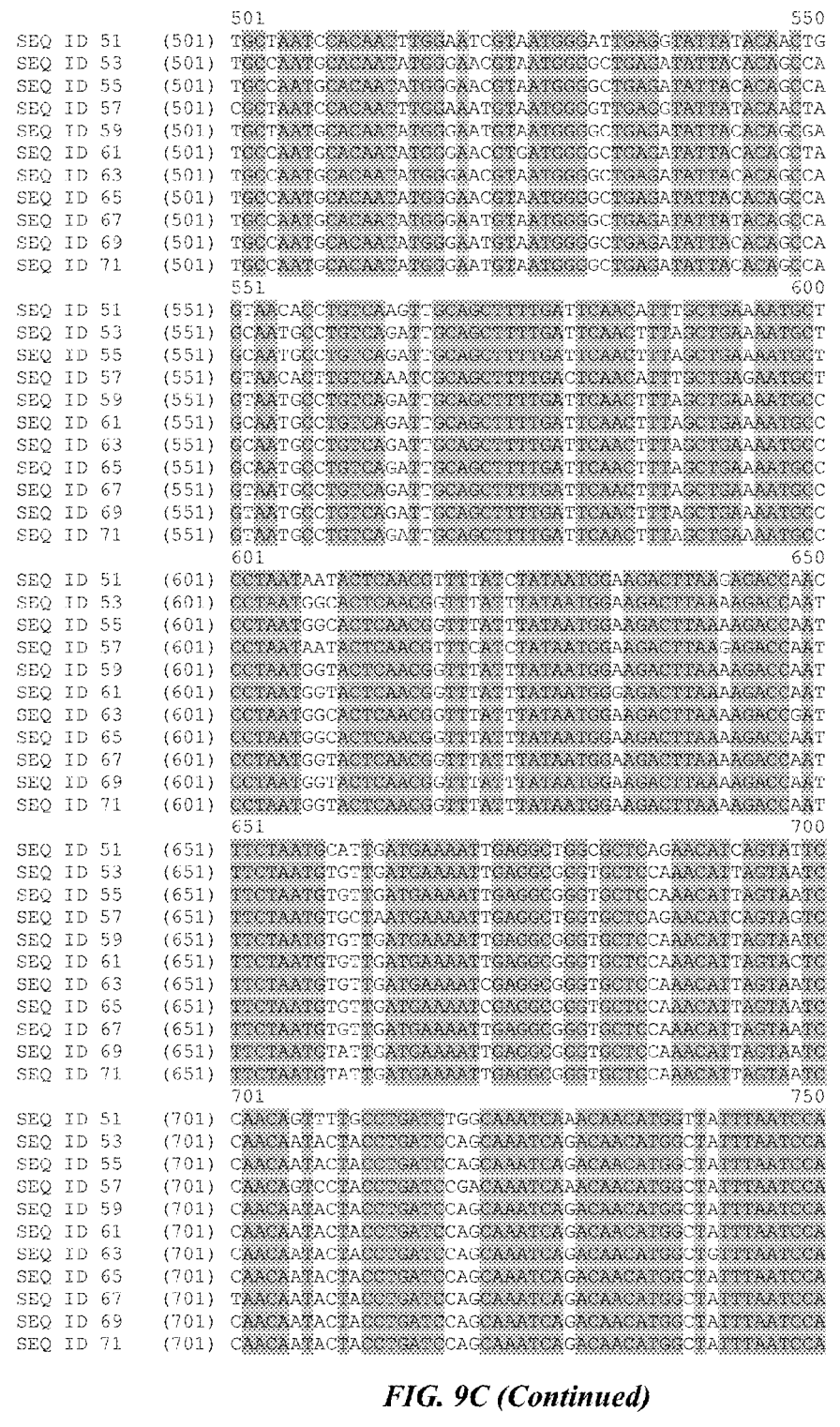
Figure 9C:
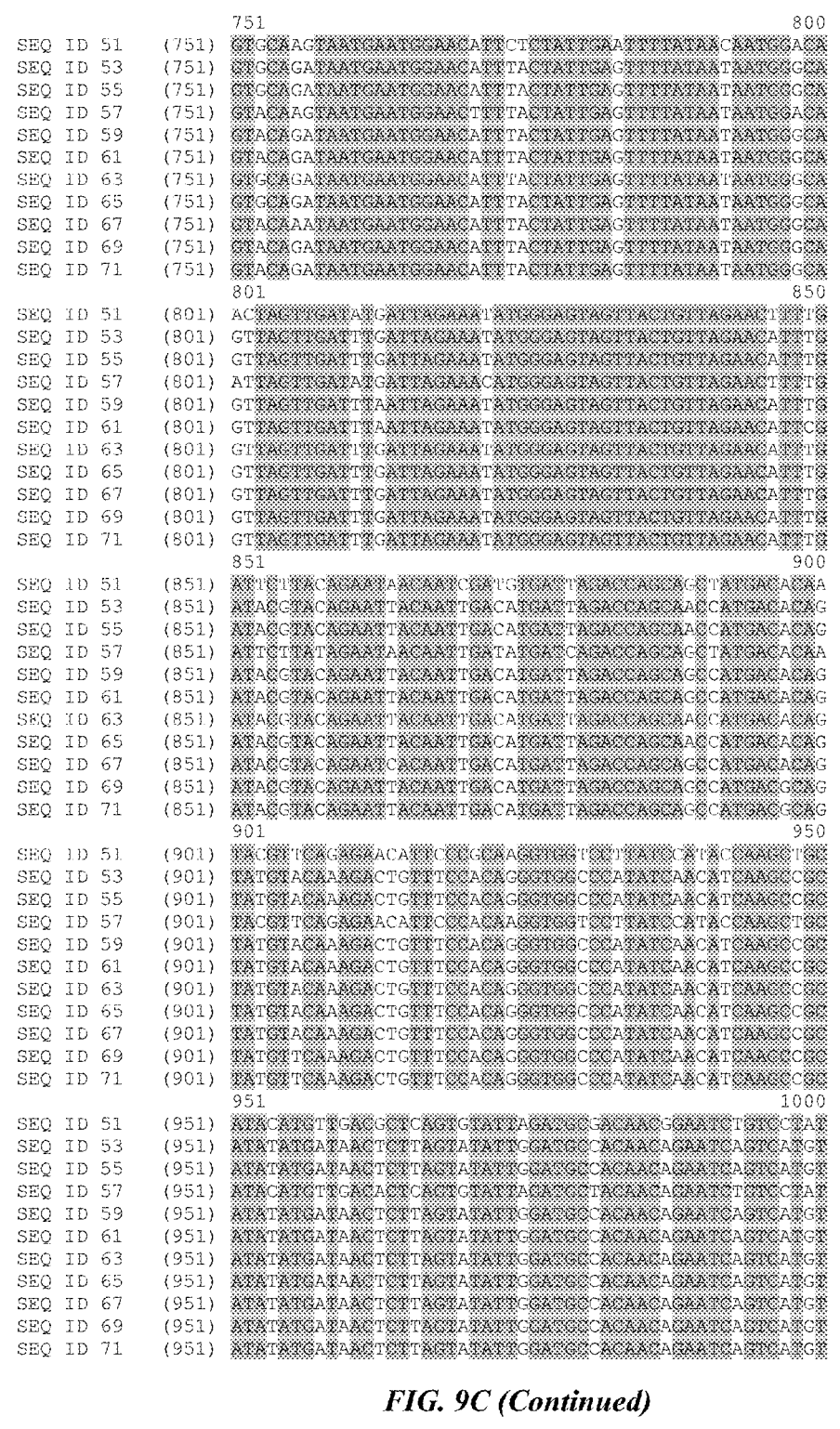
Figure 9C:
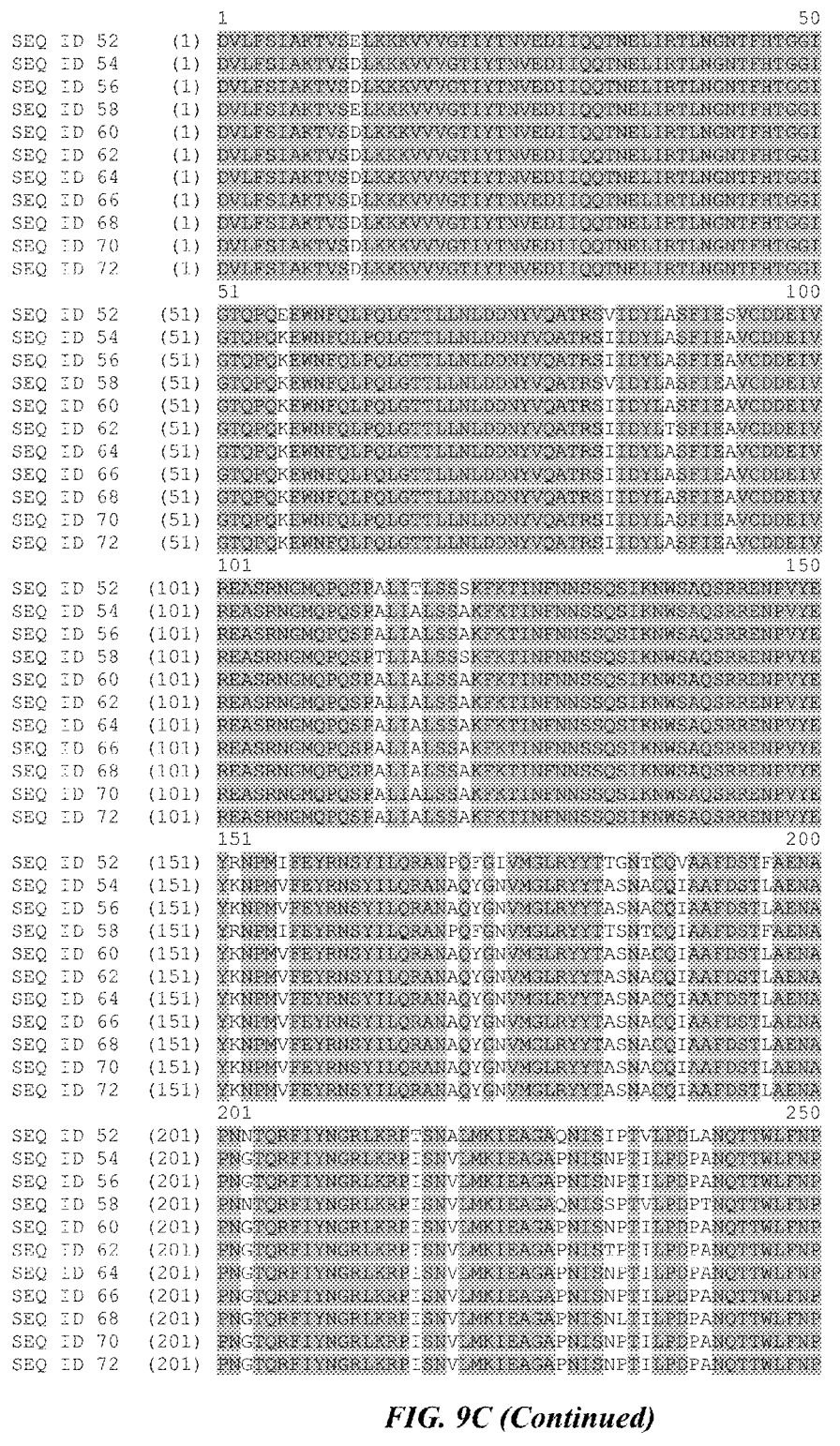

FIG. 9A presents nucleotide and peptide sequence alignments (with percent identity table) for NSP4 isolates;

FIG. 9B presents nucleotide and peptide sequence alignments (with percent identity table) for VP4 isolates;

DETAILED DESCRIPTION OF THE INVENTION

Figure 1:
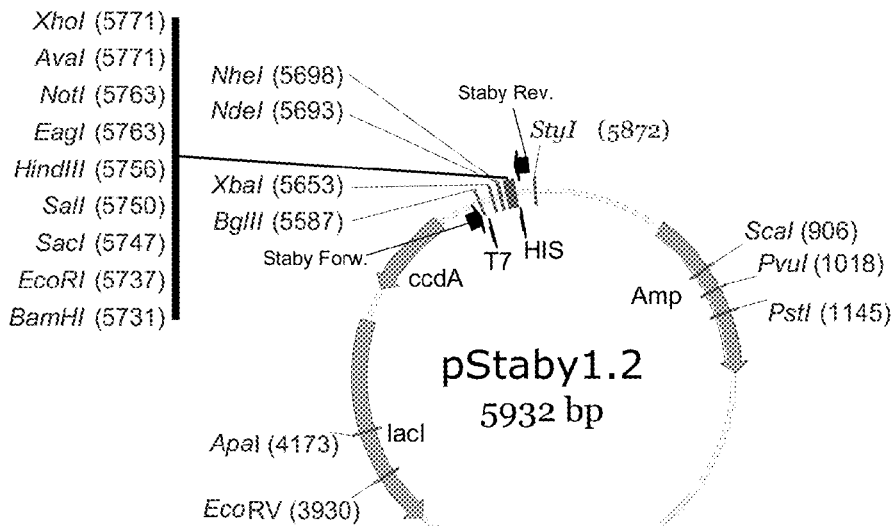
FIG. 1 provides a restriction endonuclease map of pStaby1.2 (as provided by the supplier)

The present invention encompasses rotavirus subunits (defined herein, for example, as rotavirus polypeptides, proteins, antigens, epitopes or immunogens) that elicit an immunogenic response in an animal, particularly the rotavirus subunits that elicit, induce or stimulate a response in a porcine.

Particular rotavirus subunits of interest are VP4, VP6, and NSP4, particularly those encoded by nucleic acid sequences from Group C rotavirus-infected porcines. It is recognized that precursors of any of these antigens can be used in the practice of this invention.

In an embodiment, the invention provides for a method for amplifying rotaviral sequences from infected porcines, and using well-known molecular techniques to place said amplified sequences into expression vectors. In a particular embodiment, the amplifying is accomplished by PCR using primers complementary to highly conserved regions of rotavirus genes, such that genes from a wide variety of rotavirus strains may be amplified using the same primers. In an embodiment, the primers are complementary to rotavirus nucleic acid sequence encoding VP4, VP6, and/or NSP4, and have the sequence as set forth in SEQ ID NOs:8-13).

In another aspect, the invention provides for methods for producing expression vectors, which contain and express in a prokaryotic host an antidote gene, which confers viability to bacterial cells expressing proteic toxins. In an embodiment, the antidote is ccdA and the toxin is ccdB.

In another aspect, the novel rotaviral sequences are placed into the expression vectors to produce rotavirus subunits to be used in formulation of subunit vaccines.

In an embodiment, the subunit vaccines further comprise an adjuvant. In a particular embodiment, the adjuvant is an oil-in-water adjuvant. In some embodiments, the adjuvant is TRIGEN, ULTRAGEN, PrimaVant, TS6, LR4, or combinations thereof. In an embodiment, the vaccines further comprise an adjuvanting amount of an aluminum salt. Other adjuvanting compounds may also be added to the subunit vaccines, including, but not limited to saponin and aluminum hydroxide. These additional adjuvanting compounds may improve the vaccine storage stability, the efficacy, or both.

In another aspect, the invention provides methods for providing protective immunity to piglets against rotavirus, comprising administering the inventive subunit vaccines to sows and gilts, prefarrow.

TABLE 1

List of primers used in the construction of the vectors and cloning the genes

| SEQ ID # | # | Description |
|---|---|---|
| 2 | 650 | GST For. NdeI |
| 3 | 651 | GST Rev. BamHI |
| 4 | 644 | AMP$^R$ gene deletion For. |
| 5 | 645 | AMP$^R$ gene deletion Rev. |
| 6 | 660 | PCR Verification For. |
| 7 | 661 | PCR Verification Rev. |

TABLE 1-continued

List of primers used in the construction
of the vectors and cloning the genes

| SEQ ID # | # | Description |
|---|---|---|
| 8 | 652 | NSP4 For. with BamHI site |
| 9 | 653 | NSP4 Rev. with HindIII site |
| 10 | 654 | VP4 For. with BamHI site |
| 11 | 655 | VP4 Rev. with HindIII site |
| 12 | 656 | VP6 For. with BamHI site |
| 13 | 657 | VP6 Rev. with HindIII site |
| 73 | 760 | KSN760 - rev VP4 |
| 74 | 761 | KSN761 - for VP4 |
| 75 | 762 | KSN762 - rev VP4 |
| 76 | 763 | KSN763 - for VP4 |
| 77 | 772 | Primer 1 to insert His Tag in pNPL1 |
| 78 | 773 | Primer 2 to insert His Tag in pNPL1 |
| 79 | 774 | Rota C NSP4 FOR for pNPL3 |
| 80 | 775 | Rota C NSP4 REV for pNPL3 or pNPL1 |
| 81 | 776 | Rota C VP4 FOR for pNPL3 |
| 82 | 777 | Rota C VP4 REV for pNPL3 or pNPL1 |
| 83 | 778 | Rota C VP6 FOR for pNPL3 |
| 84 | 779 | Rota C VP6 REV for pNPL3 or pNPL1 |
| 85 | 780 | Rota C NSP4 FOR for pNPL1 |
| 86 | 781 | Rota C VP4 FOR for pNPL1 |
| 87 | 782 | Rota C VP6 FOR for pNPL1 |
| 88 | 783 | Rota C VP7 FOR for pNPL3 |
| 89 | 784 | Rota C VP7 REV for pNPL3 or pNPL1 |

The antigenic polypeptides or proteins of the invention are capable of protecting against rotavirus. That is, they are capable of stimulating an immune response in an animal. By "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The term "immunogenic or antigenic polypeptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984; Geysen et al., 1986. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Methods especially applicable to the proteins of *T. parva* are fully described in PCT/US2004/022605 incorporated herein by reference in its entirety.

As discussed herein, the invention encompasses active fragments and variants of the antigenic polypeptide. Thus, the term "immunogenic or antigenic polypeptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response"

includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms and/or clinical disease signs normally displayed by an infected host, a quicker recovery time and/or a lowered viral titer in the infected host.

By "animal" is intended mammals, birds, and the like. Animal or host as used herein includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), porcine (e.g., pig), avian (e.g., chicken, duck, goose, turkey, quail, pheasant, parrot, finches, hawk, crow, ostrich, emu and cassowary), primate (e.g., prosimian, tarsier, monkey, gibbon, ape), ferrets, seals, and fish. The term "animal" also includes an individual animal in all stages of development, including newborn, embryonic and fetal stages.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Compositions

The present invention relates to a rotavirus vaccine or composition which may comprise a rotavirus polypeptide, antigen, epitope or immunogen and a pharmaceutically or veterinarily acceptable carrier, excipient, or vehicle. The rotavirus polypeptide, protein, antigen, epitope or immunogen may be any rotavirus polypeptide, protein, antigen, epitope or immunogen, such as, but not limited to, a protein, peptide or fragment thereof, that elicits, induces or stimulates a response in an animal.

The present invention relates to a rotavirus vaccine or composition which may comprise a rotavirus VP1, VP2, VP3, VP4, NSP1, VP6, NSP3, NSP2, VP7, NSP4, NSP5, or NSP6 polypeptide and a pharmaceutically or veterinarily acceptable carrier, excipient, or vehicle. In one embodiment, the expression vector may further comprise a polynucleotide encoding the VP4, VP6, or NSP4 polypeptide, or combinations thereof. In a particular embodiment, the polynucleotide comprises the sequence as set forth in SEQ ID NO:16, 18, 20, 22, 24, 26, 28, 30, 32, 34, 36, 38, 40, 42, 44, 46, 48, 50, 52, 54, 56, 58, 60, 62, 64, 66, 68, 70, 72, or combinations thereof.

In another embodiment, the pharmaceutically or veterinarily acceptable carrier, excipient, or vehicle may be a water-in-oil emulsion. In yet another embodiment, the water-in-oil emulsion may be a water/oil/water (W/O/W) triple emulsion.

In an embodiment, the rotavirus polypeptide, antigen or fragment or variant thereof comprises a rotavirus polypeptide or fragment or variant thereof. In an aspect of this embodiment, the rotavirus polypeptide or fragment or variant thereof is a recombinant polypeptide produced by a rotavirus gene. In another aspect of this embodiment, the rotavirus gene has at least 70% identity to the sequence as set forth in SEQ ID NO: 16, 18, 20, 22, 24, 26, 28, 30, 32, 34, 36, 38, 40, 42, 44, 46, 48, 50, 52, 54, 56, 58, 60, 62, 64, 66, 68, 70, 72, or combinations thereof. In another aspect of this embodiment, the rotavirus polypeptide or fragment or variant thereof has at least 80% identity to the sequence as set forth in SEQ ID NO:17, 19, 21, 23, 25, 27, 29, 31, 33, 35, 37, 39, 41, 43, 45, 47, 49, 51, 53, 55, 57, 59, 61, 63, 65, 67, 69, or 71, wherein the polypeptide or fragment or variant thereof has the same functional role (i.e. the polypeptide is rotavirus VP4, VP6, or NSP4 polypeptide belonging to a different strain of Group C rotavirus).

Synthetic antigens are also included within the definition, for example, polyepitopes, flanking epitopes, and other recombinant or synthetically derived antigens. See, e.g., Bergmann et al., 1993; Bergmann et al., 1996; Suhrbier, 1997; Gardner et al., 1998. Immunogenic fragments, for purposes of the present invention, will usually include at least about 3 amino acids, at least about 5 amino acids, at least about 10-15 amino acids, or about 15-25 amino acids or more amino acids, of the molecule. There is no critical upper limit to the length of the fragment, which could comprise nearly the full-length of the protein sequence, or even a fusion protein comprising at least one epitope of the protein.

Accordingly, a minimum structure of a polynucleotide expressing an epitope is that it comprises or consists essentially of or consists of nucleotides encoding an epitope or antigenic determinant of a rotavirus polypeptide. A polynucleotide encoding a fragment of a rotavirus polypeptide may comprise or consist essentially of or consist of a minimum of 15 nucleotides, about 30-45 nucleotides, about 45-75, or at least 57, 87 or 150 consecutive or contiguous nucleotides of the sequence encoding the polypeptide. Epitope determination procedures, such as, generating overlapping peptide libraries (Hemmer et al., 1998), Pepscan (Geysen et al., 1984; Geysen et al., 1985; Van der Zee R. et al., 1989; Geysen, 1990; Multipin® Peptide Synthesis Kits de Chiron) and algorithms (De Groot et al., 1999; PCT/US2004/022605) can be used in the practice of the invention.

The term "nucleic acid" and "polynucleotide" refers to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

The invention further comprises a complementary strand to a polynucleotide encoding a rotavirus antigen, epitope or immunogen. The complementary strand can be polymeric and of any length, and can contain deoxyribonucleotides, ribonucleotides, and analogs in any combination.

An "isolated" biological component (such as a nucleic acid or protein or organelle) refers to a component that has been substantially separated or purified away from other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "purified" as used herein does not require absolute purity; rather, it is intended as a relative term. Thus, for example, a partially purified polypeptide preparation is one in which the polypeptide is more enriched than the polypeptide is in its natural environment. That is the polypeptide is separated from cellular components. By "substantially purified" is intended that such that at least 60%, at least 70%, at least 80%, at least 90%, at least 95%, or at least 98%, or more of the cellular components or materials have been removed. Likewise, a polypeptide may be partially purified. By "partially purified" is intended that less than 60% of the cellular components or material is removed. The same applies to polynucleotides. The polypeptides disclosed herein can be purified by any of the means known in the art.

Moreover, homologs of rotavirus polypeptides are intended to be within the scope of the present invention. As used herein, the term "homologs" includes orthologs, analogs and paralogs. The tem "analogs" refers to two polynucleotides or polypeptides that have the same or similar function, but that have evolved separately in unrelated organisms. The term "orthologs" refers to two polynucleotides or polypeptides from different species, but that have evolved from a common ancestral gene by speciation. Normally, orthologs encode polypeptides having the same or similar functions. The term "paralogs" refers to two polynucleotides or polypeptides that are related by duplication within a genome. Paralogs usually have different functions, but these functions may be related. For example, analogs, orthologs, and paralogs of a wild-type rotavirus polypeptide can differ from the wild-type rotavirus polypeptide by post-translational modifications, by amino acid sequence differences, or by both. In particular, homologs of the invention will generally exhibit at least 80-85%, 85-90%, 90-95%, or 95%, 96%, 97%, 98%, 99% sequence identity, with all or part of the wild-type rotavirus polypeptide or polynucleotide sequences, and will exhibit a similar function.

In another aspect, the present invention provides a polypeptide having at least 70%, at least 75%, at least 80%, at least 85%, at least 90%, at least 95%, 96%, 97%, 98% or 99% sequence identity to a polypeptide having a sequence as set forth in SEQ ID NO: 17, 19, 21, 23, 25, 27, 29, 31, 33, 35, 37, 39, 41, 43, 45, 47, 49, 51, 53, 55, 57, 59, 61, 63, 65, 67, 69, or 71. In yet another aspect, the present invention provides fragments and variants of the rotavirus polypeptides identified above (SEQ ID NO:17, 19, 21, 23, 25, 27, 29, 31, 33, 35, 37, 39, 41, 43, 45, 47, 49, 51, 53, 55, 57, 59, 61, 63, 65, 67, 69, or 71) which may readily be prepared by one of skill in the art using well-known molecular biology techniques.

Variants are homologous polypeptides having an amino acid sequence at least 75%, 80%, 85%, 90%, 95%, 96%, 97%, 98%, or 99% identity to the amino acid sequence as set forth in SEQ ID NO:17, 19, 21, 23, 25, 27, 29, 31, 33, 35, 37, 39, 41, 43, 45, 47, 49, 51, 53, 55, 57, 59, 61, 63, 65, 67, 69, or 71.

Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same gene genetic locus in those species. Any and all such nucleic acid variations and resulting amino acid polymorphisms or variations that are the result of natural allelic variation and that do not alter the functional activity of gene of interest, are intended to be within the scope of the invention.

As used herein, the term "derivative" or "variant" refers to a polypeptide, or a nucleic acid encoding a polypeptide, that has one or more conservative amino acid variations or other minor modifications such that (1) the corresponding polypeptide has substantially equivalent function when compared to the wild type polypeptide or (2) an antibody raised against the polypeptide is immunoreactive with the wild-type polypeptide. These variants or derivatives include polypeptides having minor modifications of the rotavirus polypeptide primary amino acid sequences that may result in peptides which have substantially equivalent activity as compared to the unmodified counterpart polypeptide. Such modifications may be deliberate, as by site-directed mutagenesis, or may be spontaneous. The term "variant" further contemplates deletions, additions and substitutions to the sequence, so long as the polypeptide functions to produce an immunological response as defined herein.

The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, as described above.

An immunogenic fragment of a rotavirus polypeptide includes at least 8, 10, 13, 14, 15, or consecutive amino acids, at least 21 amino acids, at least 23 amino acids, at least 25 amino acids, or at least 30 amino acids of a rotavirus polypeptide having a sequence as set forth in SEQ ID NO:16, 18, 20, 22, 24, 26, 28, 30, 32, 34, 36, 38, 40, 42, 44, 46, 48, 50, 52, 54, 56, 58, 60, 62, 64, 66, 68, 70, 72, or variants or functional fragments thereof.

In another aspect, the present invention provides a polynucleotide encoding a rotavirus polypeptide, such as a polynucleotide encoding a polypeptide having a sequence as set forth in SEQ ID NO:16, 18, 20, 22, 24, 26, 28, 30, 32, 34, 36, 38, 40, 42, 44, 46, 48, 50, 52, 54, 56, 58, 60, 62, 64, 66, 68, 70, 72, or variants or functional fragments thereof. In yet another aspect, the present invention provides a polynucleotide encoding a polypeptide having at least 70%, at least 75%, at least 80%, at least 85%, at least 90%, at least 95%, 96%, 97%, 98% or 99% sequence identity to a polypeptide having a sequence as set forth in SEQ ID NO: 16, 18, 20, 22, 24, 26, 28, 30, 32, 34, 36, 38, 40, 42, 44, 46, 48, 50, 52, 54, 56, 58, 60, 62, 64, 66, 68, 70, 72, or a conservative variant, an allelic variant, a homolog or an immunogenic fragment comprising at least eight or at least ten consecutive amino acids of one of these polypeptides, or a combination of these polypeptides.

In another aspect, the present invention provides a polynucleotide having a nucleotide sequence as set forth in SEQ ID NO:17, 19, 21, 23, 25, 27, 29, 31, 33, 35, 37, 39, 41, 43, 45, 47, 49, 51, 53, 55, 57, 59, 61, 63, 65, 67, 69, or 71, or a variant or functional fragment thereof. In yet another aspect, the present invention provides a polynucleotide having at least 70%, at least 75%, at least 80%, at least 85%, at least 90%, at least 95%, at least 95%, 96%, 97%, 98% or 99% sequence identity to one of a polynucleotide having a sequence as set forth in SEQ ID NO: 17, 19, 21, 23, 25, 27, 29, 31, 33, 35, 37, 39, 41, 43, 45, 47, 49, 51, 53, 55, 57, 59, 61, 63, 65, 67, 69, or 71, or a variant thereof.

The polynucleotides of the disclosure include sequences that are degenerate as a result of the genetic code, e.g., optimized codon usage for a specific host. As used herein, "optimized" refers to a polynucleotide that is genetically engineered to increase its expression in a given species. To provide optimized polynucleotides coding for rotavirus polypeptides, the DNA sequence of the rotavirus gene can be modified to 1) comprise codons preferred by highly expressed genes in a particular host cell expression system (e.g. bacterial host cell); 2) comprise an A+T or G+C content in nucleotide base composition to that substantially found in said host cell; 3) form an initiation sequence of said host cell; or 4) eliminate sequences that cause destabilization, degradation and termination of RNA, or that form secondary structure hairpins. Increased expression of rotavirus protein in said host cell expression system can be achieved by utilizing the distribution frequency of codon usage in prokaryotes.

The sequence identity between two amino acid sequences may be established by the NCBI (National Center for Biotechnology Information) pairwise blast and the blosum62 matrix, using the standard parameters (see, e.g., the BLAST or BLASTX algorithm available on the "National Center for Biotechnology Information" (NCBI, Bethesda, Md., USA) server, as well as in Altschul et al.; and thus, this document speaks of using the algorithm or the BLAST or BLASTX and BLOSUM62 matrix by the term "blasts").

The "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

The sequence identity or sequence similarity of two amino acid sequences, or the sequence identity between two nucleotide sequences can be determined using Vector NTI software package (Invitrogen, 1600 Faraday Ave., Carlsbad, Calif.).

The following documents provide algorithms for comparing the relative identity or homology of sequences, and additionally or alternatively with respect to the foregoing, the teachings in these references can be used for determining percent homology or identity: Needleman S B and Wunsch C D; Smith T F and Waterman M S; Smith T F, Waterman M S and Sadler J R; Feng D F and Dolittle R F; Higgins D G and Sharp P M; Thompson J D, Higgins D G and Gibson T J; and, Devereux J, Haeberlie P and Smithies O. And, without undue experimentation, the skilled artisan can consult with many other programs or references for determining percent homology.

Hybridization reactions can be performed under conditions of different "stringency." Conditions that increase stringency of a hybridization reaction are well known. See for example, "Molecular Cloning: A Laboratory Manual", second edition (Sambrook et al., 1989).

The invention further encompasses the rotavirus polynucleotide contained in a vector molecule or an expression vector and operably linked to a promoter element and optionally to an enhancer.

A "vector" refers to a recombinant DNA or RNA plasmid or virus that comprises a heterologous polynucleotide to be delivered to a target cell, either in vitro or in vivo. The heterologous polynucleotide may comprise a sequence of interest for purposes of prevention or therapy, and may optionally be in the form of an expression cassette. As used herein, a vector needs not be capable of replication in the ultimate target cell or subject. The term includes cloning vectors and viral vectors.

The term "recombinant" means a polynucleotide with semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

Elements for the expression of a rotavirus polypeptide, antigen, epitope or immunogen are advantageously present in an inventive vector. In minimum manner, this comprises an initiation codon (ATG), a stop codon and a promoter, and optionally also a polyadenylation sequence for certain vectors such as plasmid and certain viral vectors, e.g., viral vectors other than poxviruses. When the polynucleotide encodes a polypeptide fragment, e.g. a rotavirus polypeptide, advantageously, in the vector, an ATG is placed at 5' of the reading frame and a stop codon is placed at 3'. Other elements for controlling expression may be present, such as enhancer sequences, stabilizing sequences, such as intron and signal sequences permitting the secretion of the protein.

The present invention also relates to preparations comprising vectors, such as expression vectors, e.g., therapeutic compositions. The preparations can comprise one or more vectors, e.g., expression vectors, such as in vivo expression vectors, comprising and expressing one or more rotavirus polypeptides, antigens, epitopes or immunogens. In one embodiment, the vector contains and expresses a polynucleotide that comprises a polynucleotide coding for and/or expressing a rotavirus antigen, epitope or immunogen, in a pharmaceutically or veterinarily acceptable carrier, excipient or vehicle. Thus, according to an embodiment of the invention, the other vector or vectors in the preparation comprises, consists essentially of or consists of a polynucleotide that encodes, and under appropriate circumstances the vector expresses one or more other proteins of a rotavirus polypeptide, antigen, epitope or immunogen (e.g., hemagglutinin, capsid, neuraminidase, nucleoprotein, non-structural protein, enterotoxin) or a fragment thereof.

According to another embodiment, the vector or vectors in the preparation comprise, or consist essentially of, or consist of polynucleotide(s) encoding one or more proteins or fragment(s) of a rotavirus polypeptide, antigen, epitope or immunogen. In another embodiment, the preparation comprises one, two, or more vectors comprising polynucleotides encoding and expressing, advantageously in vivo, a rotavirus polypeptide, antigen, fusion protein or an epitope thereof. The invention is also directed at mixtures of vectors that comprise polynucleotides encoding and expressing different a rotavirus polypeptides, antigens, epitopes, fusion protein, or immunogens, e.g., a rotavirus polypeptide, antigen, epitope or immunogen from different species such as, but not limited to, humans, pigs, cows or cattle, dogs, cats, and avian.

According to a yet further embodiment of the invention, the expression vector is a plasmid vector, in particular an in vivo expression vector. In a specific, non-limiting example, the pVR1020 or 1012 plasmid (VICAL Inc.; Luke et al., 1997; Hartikka et al., 1996, see, e.g., U.S. Pat. Nos. 5,846, 946 and 6,451,769) can be utilized as a vector for the insertion of a polynucleotide sequence. The pVR1020 plasmid is derived from pVR1012 and contains the human tPA signal sequence. In one embodiment the human tPA signal comprises from amino acid M(1) to amino acid S(23) in Genbank under the accession number HUMTPA14. In another specific, non-limiting example, the plasmid utilized as a vector for the insertion of a polynucleotide sequence can contain the signal peptide sequence of equine IGF1 from amino acid M(24) to amino acid A(48) in Genbank under the accession number U28070. Additional information on DNA plasmids which may be consulted or employed in the practice are found, for example, in U.S. Pat. Nos. 6,852,705; 6,818,628; 6,586,412; 6,576,243; 6,558,674; 6,464,984; 6,451,770; 6,376,473 and 6,221,362.

The term plasmid covers any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention.

Each plasmid comprises or contains or consists essentially of, in addition to the polynucleotide encoding a rotavirus polypeptide, antigen, epitope or immunogen, optionally fused with a heterologous peptide sequence, variant, analog or fragment, operably linked to a promoter or under the control of a promoter or dependent upon a promoter. In general, it is advantageous to employ a strong promoter functional in eukaryotic cells. The strong promoter may be, but not limited to, the immediate early cytomegalovirus promoter (CMV-IE) of human or murine origin, or optionally having another origin such as the rat or guinea pig.

In more general terms, the promoter has either a viral, or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa et al., 2000), or the actin promoter (Miyazaki et al., 1989).

As to the polyadenylation signal (polyA) for the plasmids and viral vectors other than poxviruses, use can be made of the poly(A) signal of the bovine growth hormone (bGH) gene (see U.S. Pat. No. 5,122,458), or the poly(A) signal of the rabbit β-globin gene or the poly(A) signal of the SV40 virus.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof.

Methods of Use and Article of Manufacture

The present invention includes the following method embodiments. In an embodiment, a method of vaccinating an animal comprising administering a composition comprising a vector comprising a rotavirus polypeptide or fragment or variant thereof and a pharmaceutical or veterinarily acceptable carrier, excipient, or vehicle to an animal is disclosed. In one aspect of this embodiment, the animal is a porcine.

In one embodiment of the invention, a prime-boost regimen can be employed, which is comprised of at least one primary administration and at least one booster administration using at least one common polypeptide, antigen, epitope or immunogen. Typically the immunological composition or vaccine used in primary administration is different in nature from those used as a booster. However, it is noted that the same composition can be used as the primary administration and the booster administration. This administration protocol is called "prime-boost".

A prime-boost regimen comprises at least one prime-administration and at least one boost administration using at least one common polypeptide and/or variants or fragments thereof. The vaccine used in prime-administration may be different in nature from those used as a later booster vaccine. The prime-administration may comprise one or more administrations. Similarly, the boost administration may comprise one or more administrations.

The dose volume of compositions for target species that are mammals, e.g., the dose volume of pig or swine compositions, based on viral vectors, e.g., non-poxvirus-viral-vector-based compositions, is generally between about 0.1 to about 2.0 ml, between about 0.1 to about 1.0 ml, and between about 0.5 ml to about 1.0 ml.

The efficacy of the vaccines may be tested about 2 to 4 weeks after the last immunization by challenging animals, such as porcine, with a virulent strain of rotavirus. Both homologous and heterologous strains are used for challenge to test the efficacy of the vaccine. The animal may be challenged by IM or SC injection, spray, intra-nasally, intra-ocularly, intra-tracheally, and/or orally. The challenge virus may be about $10^{5-8}$ $EID_{50}$, $TCID_{50}$ or $10^{3-8}$ genome equivalents as determined by qPCR in a volume depending upon the route of administration. For example, if the administration is by spray, a virus suspension is aerosolized to generate about 1 to 100 µm droplets, if the administration is intra-nasal, intra-tracheal or oral, the volume of the challenge virus is about 0.5 ml, 1-2 ml, and 5-10 ml, respectively. Animals may be observed daily for 14 days following challenge for clinical signs, for example, dehydration, diarrhea, pasty to watery feces, death, and/or loss of weight, failure to thrive, virus shedding. In addition, the groups of animals may be euthanized and evaluated for pathological findings intestinal disease, villous atrophy. Rectal or fecal swabs may be collected from all animals post challenge for virus isolation or quantification, or detection. The presence or absence of viral antigens in intestinal tissues or feces may be evaluated by quantitative real time reverse transcriptase polymerase chain reaction (qRT-PCR). Blood samples may be collected before and post-challenge and may be analyzed for the presence of rotavirus-specific antibody.

The compositions comprising the recombinant antigenic polypeptides of the invention used in the prime-boost protocols are contained in a pharmaceutically or veterinary acceptable vehicle, diluent or excipient. The protocols of the invention protect the animal from rotavirus and/or prevent disease progression in an infected animal.

The various administrations are preferably carried out 1 to 6 weeks apart. Preferred time interval is 3 to 5 weeks, and optimally 4 weeks According to one embodiment, an annual booster is also envisioned. The animals, for example pigs, may be at least 8 weeks of age at the time of the first administration.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation.

The present invention contemplates at least one administration to an animal of a sufficient amount of the therapeutic composition made according to the invention. For example, the sufficient amount may be from about 10 µg to about 300 µg of protein. In an embodiment, about 100 µg of each of three different group C rotavirus proteins be present in a sufficient amount of the therapeutic composition. The animal may be male, female, pregnant female and newborn. This administration may be via various routes including, but not limited to, intramuscular (IM), intradermal (ID), intraperitoneal (IP) or subcutaneous (SC) injection or via intranasal or oral administration. The therapeutic composition according to the invention can also be administered by a needleless apparatus (as, for example with a Pulse Needle Free, Pulse Needlefree, Lenexa, Kans., USA, Pigjet, Dermojet, Biojector, Avijet (Merial, Ga., USA), Vetjet or Vitajet apparatus (Bioject, Oregon, USA)). Another approach to administering plasmid compositions is to use electroporation (see, e.g. Tollefsen et al., 2002; Tollefsen et al., 2003; Babiuk et al., 2002; PCT Application No. WO99/01158). In another embodiment, the therapeutic composition is delivered to the animal by gene gun or gold particle bombardment. In an advantageous embodiment, the animal is a pig, dog, ferret or seal.

Another embodiment of the invention is a kit for performing a method of eliciting or inducing an immunological or protective response against rotavirus in an animal comprising a rotavirus subunit immunological composition or vaccine and instructions for performing the method of delivery in an effective amount for eliciting an immune response in the animal.

Another embodiment of the invention is a kit for performing a method of inducing an immunological or protective response against rotavirus in an animal comprising a composition or vaccine comprising a rotavirus polypeptide or antigen of the invention, and instructions for performing the method of delivery in an effective amount for eliciting an immune response in the animal.

Yet another aspect of the present invention relates to a kit for prime-boost vaccination according to the present invention as described above. The kit may comprise at least two vials: a first vial containing a vaccine or composition for the prime-vaccination according to the present invention, and a second vial containing a vaccine or composition for the boost-vaccination according to the present invention. The kit may advantageously contain additional first or second vials for additional prime-vaccinations or additional boost-vaccinations.

The pharmaceutically or veterinarily acceptable carriers or vehicles or excipients are well known to the one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The cationic lipids containing a quaternary ammonium salt which are advantageously but not exclusively suitable for plasmids, are advantageously those having the following formula:

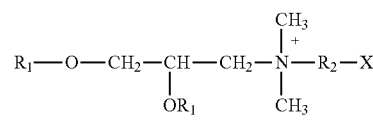

in which R1 is a saturated or unsaturated straight-chain aliphatic radical having 12 to 18 carbon atoms, R2 is another aliphatic radical containing 2 or 3 carbon atoms and X is an amine or hydroxyl group, e.g. the DMRIE. In another embodiment the cationic lipid can be associated with a neutral lipid, e.g. the DOPE.

Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidyl-ethanol amine; Behr, 1994), to form DMRIE-DOPE.

When DOPE is present, the DMRIE:DOPE molar ratio is advantageously about 95:about 5 to about 5:about 95, more advantageously about 1:about 1, e.g., 1:1.

In another embodiment, pharmaceutically or veterinarily acceptable carrier, excipient, or vehicle may be a water-in-oil emulsion. Examples of suitable water-in-oil emulsions include oil-based water-in-oil vaccinal emulsions which are stable and fluid at 4° C. containing from 6 to 50 v/v % of an antigen-containing aqueous phase, preferably from 12 to 25 v/v %, from 50 to 94 v/v % of an oil phase containing in total or in part a non-metabolizable oil (e.g., mineral oil such as paraffin oil) and/or metabolizable oil (e.g., vegetable oil, or fatty acid, polyol or alcohol esters), from 0.2 to 20 p/v % of surfactants, preferably from 3 to 8 p/v %, the latter being in total or in part, or in a mixture either polyglycerol esters, said polyglycerol esters being preferably polyglycerol (poly) ricinoleates, or polyoxyethylene ricin oils or else hydrogenated polyoxyethylene ricin oils. Examples of surfactants that may be used in a water-in-oil emulsion include ethoxylated sorbitan esters (e.g., polyoxyethylene (20) sorbitan monooleate (TWEEN 80®), available from AppliChem, Inc., Cheshire, Conn.) and sorbitan esters (e.g., sorbitan monooleate (SPAN 80®), available from Sigma Aldrich, St. Louis, Mo.). In addition, with respect to a water-in-oil emulsion, see also U.S. Pat. No. 6,919,084. In some embodiments, the antigen-containing aqueous phase comprises a saline solution comprising one or more buffering agents. An example of a suitable buffering solution is phosphate buffered saline. In an advantageous embodiment, the water-in-oil emulsion may be a water/oil/water (W/O/W) triple emulsion (U.S. Pat. No. 6,358,500). Examples of other suitable emulsions are described in U.S. Pat. No. 7,371,395.

The immunological compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on page 147 of "Vaccine Design, The Subunit and Adjuvant Approach" published by M. Powell, M. Newman, Plenum Press 1995, and the emulsion MF59 described on page 183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

The oil in water emulsion (3), which is especially appropriate for viral vectors, can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters.

The oil is used in combination with emulsifiers to form an emulsion. The emulsifiers may be nonionic surfactants, such as: esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated, or polyoxypropylene-polyoxyethylene copolymer blocks, such as Pluronic, e.g., L121.

Among the type (1) adjuvant polymers, preference is given to polymers of crosslinked acrylic or methacrylic acid, especially crosslinked by polyalkenyl ethers of sugars or polyalcohols. These compounds are known under the name carbomer (Pharmeuropa, vol. 8, no. 2, June 1996). One skilled in the art can also refer to U.S. Pat. No. 2,909,462, which provides such acrylic polymers crosslinked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name Carbopol (BF Goodrich, Ohio, USA) are especially suitable. They are crosslinked by allyl saccharose or by allyl pentaerythritol. Among them, reference is made to Carbopol 974P, 934P and 971P.

As to the maleic anhydride-alkenyl derivative copolymers, preference is given to EMA (Monsanto), which are straight-chain or crosslinked ethylene-maleic anhydride copolymers and they are, for example, crosslinked by divinyl ether. Reference is also made to J. Fields et al., 1960.

With regard to structure, the acrylic or methacrylic acid polymers and EMA are preferably formed by basic units having the following formula:

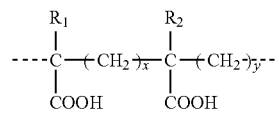

in which:
R1 and R2, which can be the same or different, represent H or CH3
x=0 or 1, preferably x=1
y=1 or 2, with x+y=2.
For EMA, x=0 and y=2 and for carbomers x=y=1.

These polymers are soluble in water or physiological salt solution (20 g/l NaCl) and the pH can be adjusted to 7.3 to 7.4, e.g., by soda (NaOH), to provide the adjuvant solution in which the expression vector(s) can be incorporated. The polymer concentration in the final immunological or vaccine composition can range between about 0.01 to about 1.5% w/v, about 0.05 to about 1% w/v, and about 0.1 to about 0.4% w/v.

The cytokine or cytokines (5) can be in protein form in the immunological or vaccine composition, or can be co-expressed in the host with the immunogen or immunogens or epitope(s) thereof. Preference is given to the co-expression of the cytokine or cytokines, either by the same vector as that expressing the immunogen or immunogens or epitope(s) thereof, or by a separate vector thereof.

The invention comprehends preparing such combination compositions; for instance by admixing the active components, advantageously together and with an adjuvant, carrier, cytokine, and/or diluent.

Cytokines that may be used in the present invention include, but are not limited to, granulocyte colony stimulating factor (G-CSF), granulocyte/macrophage colony stimulating factor (GM-CSF), interferon Δ (IFNγ), interferon β (IFNβ), interferon γ, (IFNγ), interleukin-1α(IL-1α), interleukin-1β (IL-1β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), tumor necrosis factor α (TNFα), tumor necrosis factor β (TNFβ), and transforming growth factor β (TGFβ). It is understood that cytokines can be co-administered and/or sequentially administered with the immunological or vaccine composition of the present invention. Thus, for instance, the vaccine of the instant invention can also contain an exogenous nucleic acid molecule that expresses in vivo a suitable cytokine, e.g., a cytokine matched to this host to be vaccinated or in which an immunological response is to be elicited (for instance, a canine cytokine for preparations to be administered to canine).

The invention will now be further described by way of the following non-limiting examples.

EXAMPLES

Summary

Figure 7:
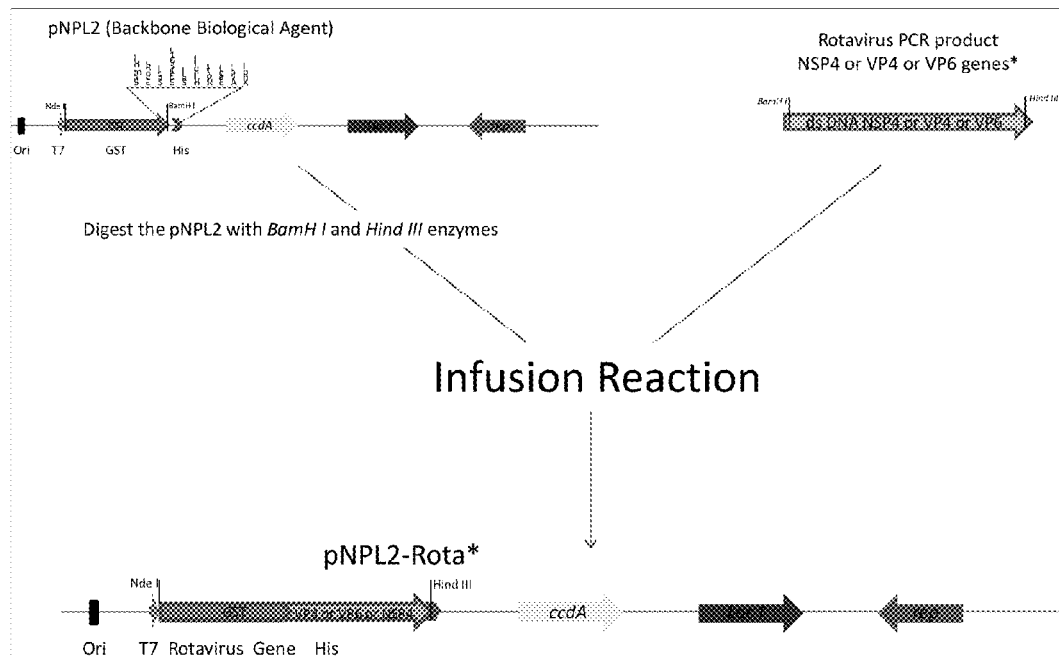
FIG. 7 is a schematic of procedure used to insert donor DNA pNPL2 to yield pNPL2-Rota.
Figure 8:
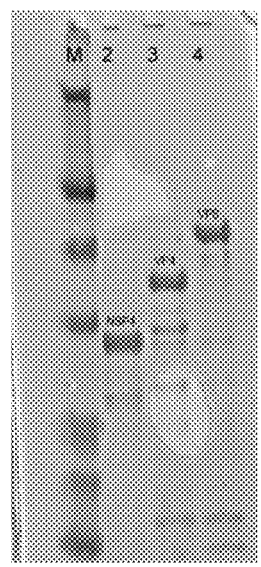
FIG. 8 is a PAGE gel confirming expression and size of the rotavirus VP4, VP6 and NSP4 proteins.
Figure 9C:
FIG. 9C presents nucleotide and peptide sequence alignments (with percent identity table) for VP6 isolates.
Figure 10:
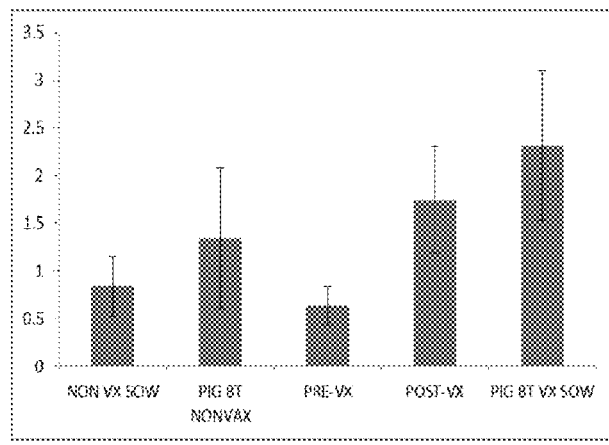
FIG. 10 is a graph showing the overall serology results for the vaccine efficacy study.
Figure 11:
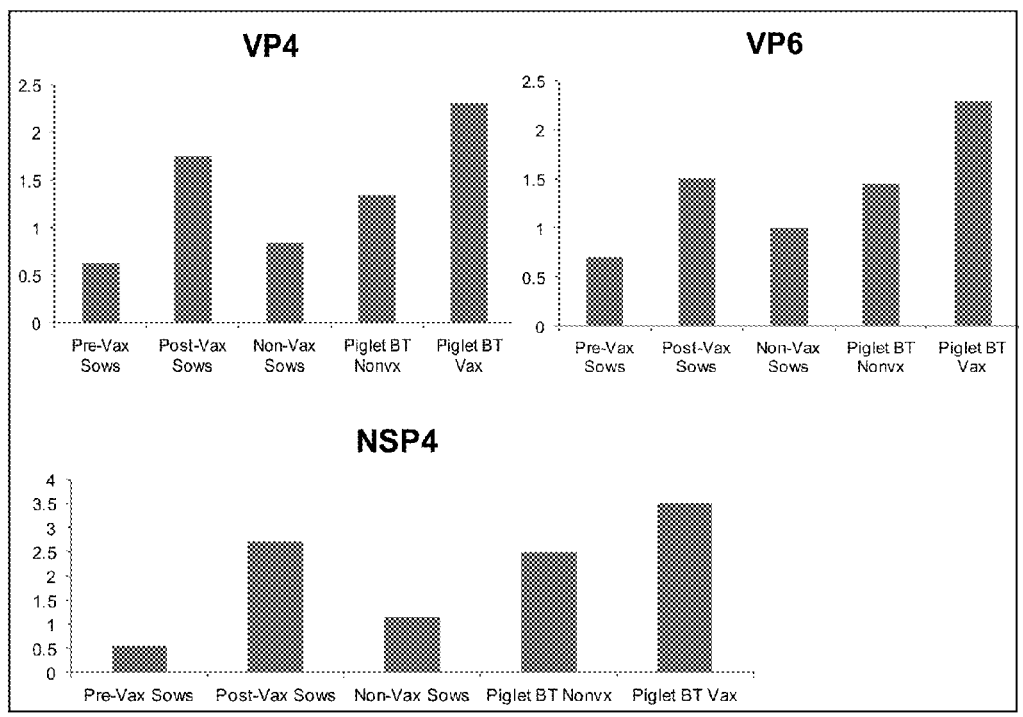
FIG. 11 are graphs showing VP4, VP6, and NSP4-specific serology as measured by ELISA.

Viral vaccines are typically made using whole virus isolated from clinical samples from infected animals, by virus adaptation and propagation in egg embryo or in vitro cell culture. Group C Porcine Rotaviruses are notoriously difficult to recover by these conventional virological techniques, and rotaviruses generally are thought to be prone to antigenic distortion during adaptation to egg embryo or cell culture growth, resulting in suboptimal vaccine production from the isolated whole virus. Thus, an expression vector (pNPL2, SEQ ID NO:15) was constructed to enable production of vaccine comprising Porcine Rotavirus Group C VP4, VP6 and/or NSP4 Recombinant Proteins. Rotavirus genetic material was rescued by PCR from clinical material submitted by a herd veterinarian. To pNPL2 was added (via the process described herein and depicted in FIG. 7) a gene encoding VP4 (18, 20, 22, 24, 26, 28, 30, 32, 34, 36, 38, or 40), VP6 (42, 44, 46, 48, or 50), or NSP4 (52, 54, 56, 58, 60, 62, 64, 66, 68, 70, or 72) polypeptides/subunits, to yield pNPL2-RotaC vectors, each of which encoding and capable of expressing in a bacterial host cell a portion of either NSP4, VP4, or VP6. These vectors were then grown in SE1 E. coli cells, which constitutively express the ccdB proteic toxin, which kills the bacteria in absence of the vector. Cells were grown, inactivated, and then the recombinantly-expressed rotaviral proteins were harvested and formulated with adjuvant for use as a non-viable subunit protein autogenous vaccine. The inventive vaccine compositions elicited in the porcines protective immunity against rotavirus.

Example 1

Construction of Vector for Autogenous or Commercial Production of Rotavirus Subunit Vaccines pNPL1 & 2 expression vector construction. The expression vector pNPL2 (SEQ ID NO:15) was constructed from the pStaby1.2 vector (SEQ ID NO:1) of Delphi Genetics (pStaby1.2 user's manual, as published in 2011), by deletion of the ampicillin resistance gene and insertion of a GST (glutathione S-transferase) gene, to facilitate down-stream protein processing during production. The vector contains nor expresses no known mammalian virulence features, and furthermore, all antibiotic resistance genes were removed from same during its construction. pNPL2 were grown in SE1 E. coli, and together they are a B Strain E. coli host/vector production system (pStaby User Manual).

The restriction map of pStaby1.2 is presented in FIG. 1, and as indicated, contains a T7 promoter to drive the expression of the gene encoding the recombinant protein. The plasmid also contains the ccdA gene, which codes for an unstable antidote protein, which inhibits expression of a stable antigyrase protein (ccdB) which is toxic to Enterobacteriaceae cells. The ccdB protein is coded for by the ccdB gene which is present in the chromosome of the host SE1 E. coli host cells (the ccdB gene is not present in the pStaby1.2 plasmid). After transformation, the presence of the ccdA gene in the plasmid ensures successfully transformed cells are viable while non-plasmid-bearing SE1 cells produce toxin without antidote and are thus non-viable.

Figure 2:
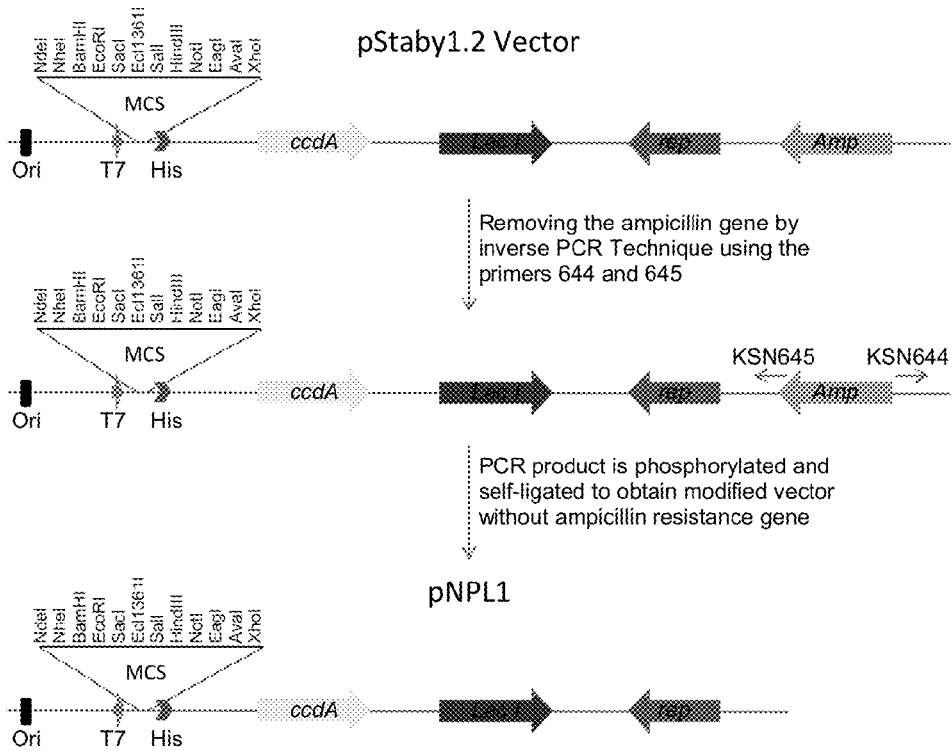
FIG. 2 schematizes removal of the ampicillin resistance gene from pStaby1.2.
Figure 3:
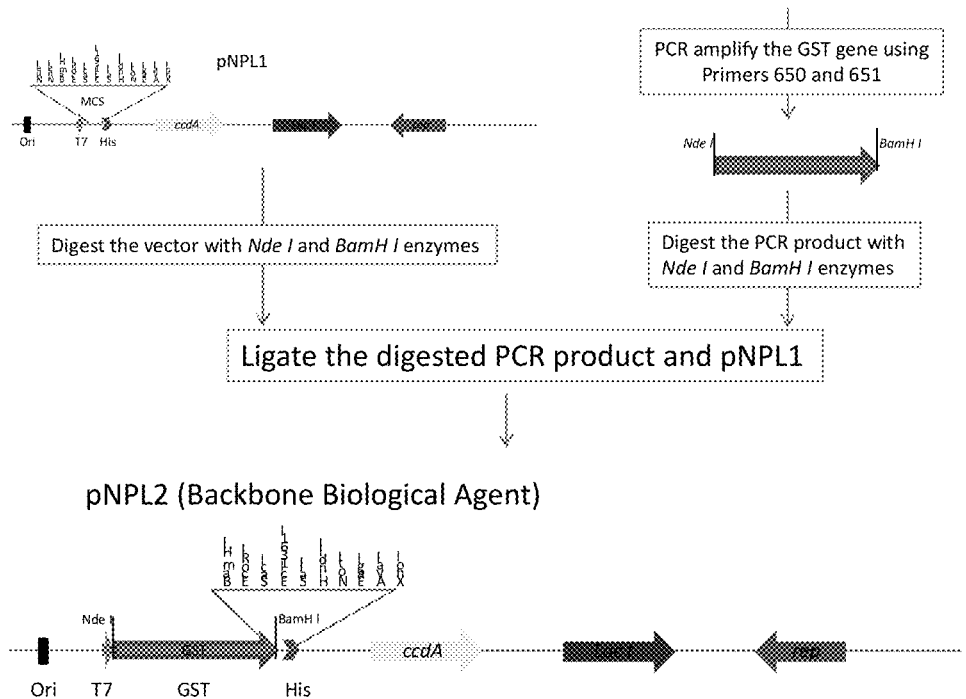
FIG. 3 schematizes insertion of GST gene into pNPL1 to form pNPL2.
Figure 4:
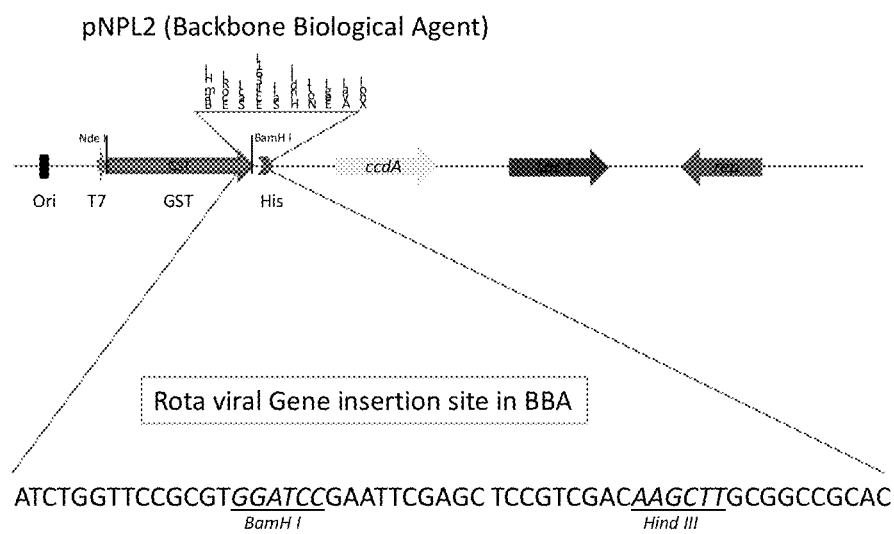
FIG. 4 is a map of flanking regions and the rotavirus gene insertion sites of pNPL2.

The ampicillin resistance gene of pStaby1.2 vector was considered undesirable for use in subunit rotavirus vaccine production, and was therefore removed using inverse PCR technique (FIG. 2). A list of primers used for all disclosed procedures is shown in Table 1. The final PCR product was phosphorylated and self-ligated to yield pNPL1 (SEQ ID NO:14). GST was then added to pNPL1 to increase the size of any expressed protein, and to improve downstream processing/inline analysis. GST was PCR amplified from pGEX4T.1 (GE Life Sciences) using primers #650 (SEQ ID NO:2) and #651 (SEQ ID NO:3), and then the amplicon (SEQ ID NO:16) was digested and cloned into NdeI-BamHI-linearized pNPL1 to yield pNPL2 (FIGS. 2-4). pNPL2 digested with BamHI and HindIII yield two bands visible on an agarose gel (5682 bp and 25 bp).

Construction of pNPL3.

PCR was performed using primers KSN772 (SEQ ID NO:77) and KSN773 (SEQ ID NO:78), and pNPL1 as the template. The PCR product is phosphorylated and self-ligated to from pNPL3, which now contained a hexa-HIS Tag. NSP4, VP4, VP6 or VP7 genes can be cloned into the BamHI and HindIII digested pNPL3 vector by infusion reaction using the PCR products generated by using primers at set forth in SEQ ID NOs:79-89. pNPL3 is similar to pNPL2, except that pNPL3 lacks sequence coding for GST gene. Instead, pNPL3 has a sequence coding for a His Tag, allowing for N-terminal His Tagged fusion peptides.

Example 2

Production of Autogenous Rotavirus Subunit Vaccine

Figure 5:
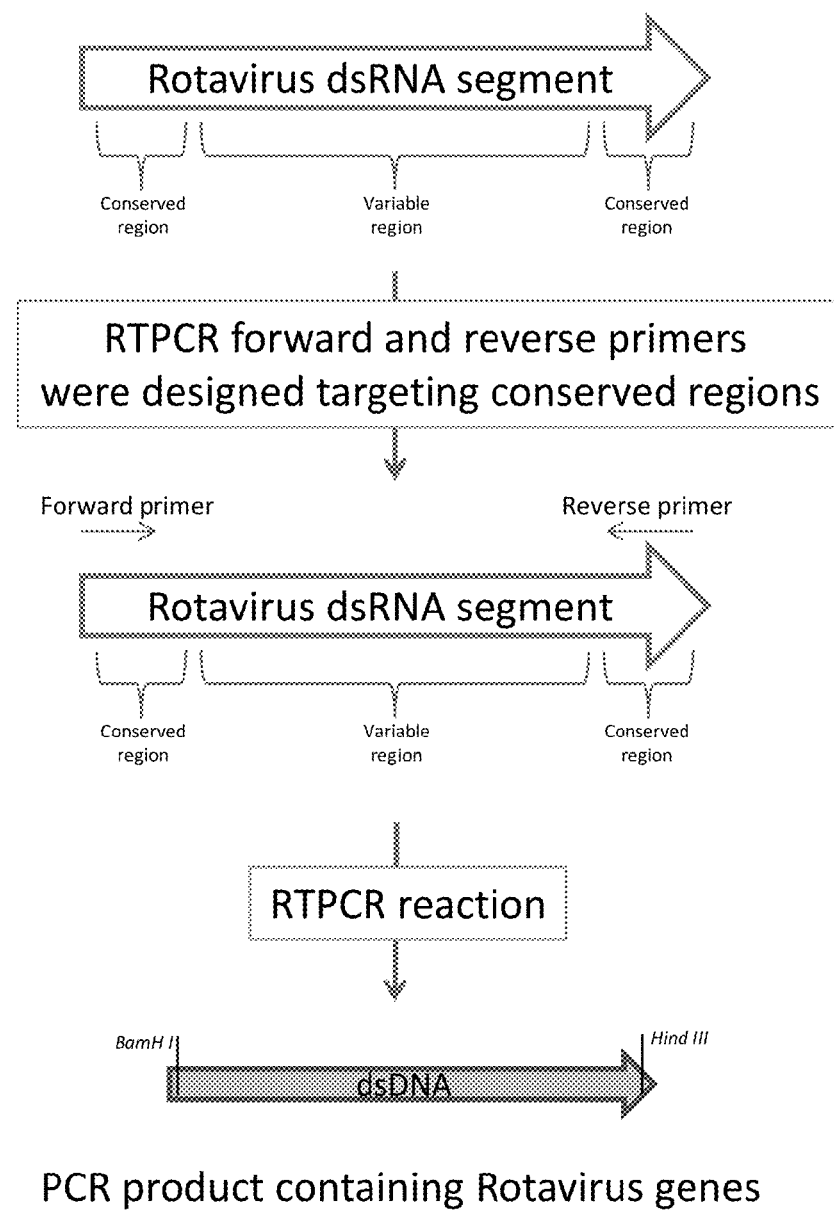
FIG. 5 is a schematic diagram of the donor DNA recovery technique.
Figure 6:
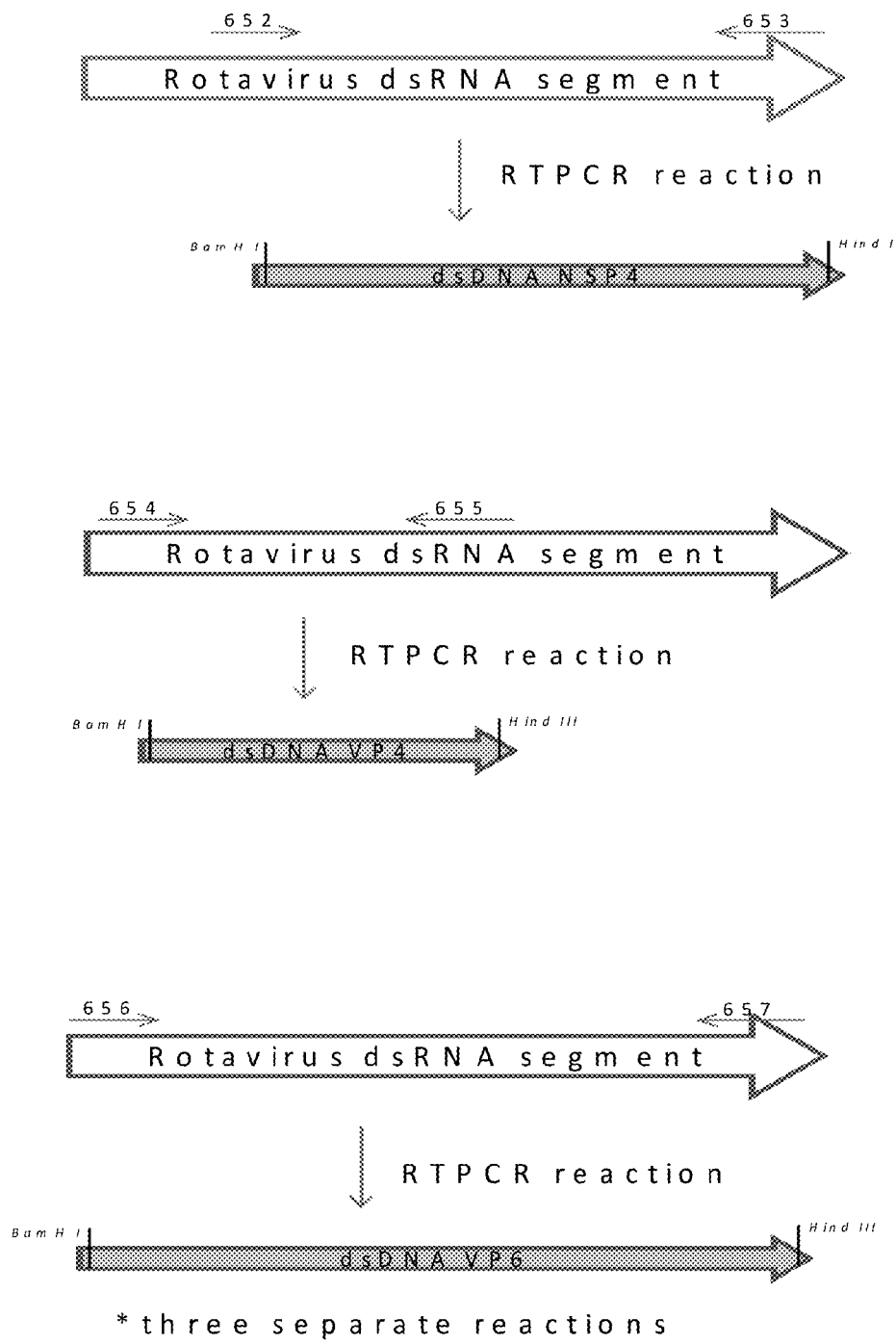
FIG. 6 schematizes the process of isolating autogenous vaccine candidate rotavirus genes from clinical samples.

Rotaviral RNAs were isolated, purified directly from clinical samples collected from infected pigs, and subjected to reverse transcription-PCR (RTPCR) using primers specific for genes encoding VP4 (primers given by SEQ ID NOs:10, 11), VP6 (primers given by SEQ ID NO:12, 13), and NSP4 (primers given by SEQ ID NO:8, 9). Each primer pair was designed to bind to a highly conserved region on each end of the target gene (FIG. 5), enabling amplification of group C rotaviral genes from many different viral isolates. If the genes cannot be amplified using the Rotavirus C gene-specific primers as set forth in SEQ ID NOs:8, 9, 10, 11, 12, and 13, alternate primers may be designed and used by skilled persons using techniques well-known in the art.

For example, degenerate primers may be employed, such that critical primer positions (e.g. the 3' terminal nucleotide) can be varied to accommodate template deviation from the conserved sequences. Primers having the sequence as set forth in SEQ ID NOs:73, 74, 75, and 76 may be used to amplify and clone VP4 sequences into pNPL1 and/or pNPL2. SEQ ID NOs:73 and 74 can be used to amplify the VP4 sequence and clone it into the TOPO vector. Thereafter, SEQ ID NOs:75 and 76 can be used to insert the VP4 sequence into the pNPL2 vector, for subsequent subunit vaccine production.

The 5' end of each primer included a 15-nucleotide sequence to allow for insertion into pNPL2 during a subsequent infusion reaction. Isolation and amplification of the field-origin rotaviral genes for production of Donor DNA to be used in the expression system are shown in FIGS. 4, 5 and 6. The presence of both the ccdA (vector encoded) and ccdB (cell genome encoded) genes within transformed SE1 cells results in viable stable cultures expressing the rotavirus gene. Any non-transformed or plasmid-cured cells are non-viable. Gene insertion was characterized and verified by sequencing, and protein expression was verified by SDS PAGE (FIG. 8), which indicated approximate molecular weights of 36 kDa (NSP4), 52 kDa (VP4), and 68 kDa (VP6). This approach is envisioned to be applicable to any rotavirus field strain having sufficient homology to the cloning primers in the conserved regions.

For large scale production, single colonies or multiple uniform colonies were transferred to 10 mL-200,000 mL LB media. When the optical density, measured at 600 nm, reached 0.4-1.0, IPTG ([Isopropyl β-D-thiogalactopyranoside] Sigma Aldrich Catalog No. I5502 or equivalent) was added at a final concentration of 1 mM. The cultures were incubated for an additional 2-6 hours. Cultures may be grown in a fermenter, as follows:

a. Temperature of the culture is maintained at 36°±3° C.

b. Filtered compressed air flow is maintained at 0.1-300 L/minute.

c. pH of the culture is maintained at 7.4±0.3.

d. When the optical density, measured at 600 nm, reaches 0.4-1.0, IPTG is added at a final concentration of 1 mM. The cultures are incubated for an additional 2-6 hours.

Harvest Technique.

The spent culture medium was separated from the *E. coli* cells by filtration or centrifugation, and the cells were concentrated by filtration using a 0.1-0.45 micron filter. Concentrated cells were then lysed using B-PER reagent (Thermo Scientific, Catalog No. 78248 or equivalent) then stirring or agitating the solution for 0.5-2 hours. The lysed cells were concentrated by centrifugation at 5000-10000 g for 15-30 minutes or by filtration using 0.1-0.45 micron filter and the supernatant/permeate was discarded. The pellet/concentrate was resuspended in wash buffer A (20 mM Tris-HCL, 2 mM EDTA and 0.1% TritonX-100, adjust pH to 7.5-8.5) by stirring or agitating for 0.1-0.5 hours, and the resulting suspension was concentrated by centrifugation at 5000-10000 g for 15-30 minutes or by filtration using a 0.1-0.45 micron filter. The pellet/concentrate was resuspended in wash buffer B (20 mM Tris-HCL and 2 mM EDTA, adjust pH to 7.5-8.5) by stirring or agitating for 0.1-0.5 hours, then the suspension was concentrated by centrifugation at 5000-10000 g for 15-30 minutes or by filtration using a 0.1-0.4 micron filter. After suspending in 8M Urea (Sigma-Aldrich, Catalog No. U6504 or equivalent) and stirring or agitating for 0.5-2 hours, the final suspension was diluted with sterile PBS.

Vaccine Formulations.

After harvest, rotavirus subunits were formulated with TRIGEN (oil-in-water) and preservatives (gentamicin at a concentration of <30.0 μg/mL and amphotericin B at a concentration of <2.50 μg/mL or polymyxin B at a concentration of <30 μg/mL). To the mixture was added a) aluminum hydroxide gel (ALHYDROGEL® "85", manufactured by Brenntag Biosector, Cat. No. EMS 2485-2 or REHYDRAGEL HPA, Reheis Cat. No. 203130070600, REHYDRAGEL LV, Reheis Cat. No. 203120070602 or equivalent) providing from about 0.1 to about 0.5% $Al_2O_3$ in the final product. Alternatively, Quil A adjuvant was present in the formulations at a rate of 0.5 to 2.5% of inactivated fluids with oil in water adjuvant. Adjuvants comprise from about 10 to about 50% of the final product.

Example 3

Immunization of Sows Using Autogenous Rotavirus Subunit Vaccines

Summary.

48 research sows, chronically infected with Rotavirus C and of similar parity were enrolled into the vaccine efficacy study. Twenty-six (26) animals were placebo vaccinated controls, while 22 animals received rotavirus subunit vaccine comprising a mixture of VP4, VP6, NSP4, and emulsion/additional adjuvants. The vaccine is formulated such that there is about 100 microgram of each protein (total of 300 microgram of protein) and 10% Trigen per each dose of vaccine. Vaccines were administered intramuscularly at 6 and 3 weeks prefarrowing. Sow blood serum was collected prior to vaccination and farrowing, and piglets blood serum was subsequently collected at 7 days post farrowing.

Results.

Piglets born from non-vaccinated sows had a 21% mortality rate, as compared to piglets born from vaccinated sows, which had a 14% mortality rate (i.e. 33% decrease). Morbidity was also significantly decreased in pigs born to vaccinated sows. Piglets from vaccinated sows also had significantly ($p<0.05$) higher antibody titers than did control piglets (FIG. 9).

Example 4

Efficacy of a Novel Rotavirus C Vaccine in Reducing Suckling Pig Scour Incidence and Improving Performance Summary.

A 3600 sow breed to wean herd was selected to evaluate the efficacy of a novel Rotavirus C vaccine. The herd consisted of PIC L03 females crossed with Line 02 boars. All diets fed on the farm are formulated to meet or exceed nutrient requirements (NRC, 1998). Sows and gilts were randomly assigned to one of two treatments (control (CON) or Rota C RS vaccine (VACC) based on the day of breeding and within parity. Animals in the assigned VACC group received 2 ml of vaccine intramuscularly at 3 weeks; 3 and 5 weeks; or 3, 5, and 8 weeks pre-farrow. All litters from these animals were cross fostered within 24 hours of birth by treatment. Scour scores were conducted daily from day of birth to day 5. A score was given as 0 (no scour), 1 (small number scouring), 2 (50% of the litter scouring), or 3 (more than 50% of the litter scouring). Pigs removed from the original litters due to mortality associated with scours were recorded. There were no differences scour scores or mortality associated with scours when either the 3 week or the 3, 5, and 8 week vaccination programs were used. However, scour scores were reduced between the CON and VACC (3 and 5 week) treatments (0.56 vs. 0.41, P<0.05). In addition, the percent of scouring litters was reduced from day 1 through day 5 with the VACC treatment (week 3 and 5) versus the CON. In conclusion, the novel Rotavirus C vaccine did not alter the incidence of suckling pig scour rate or mortality when sows were vaccinated once or three times. However, the use of the novel vaccine did appear to reduce scour incidence when given at 3 and 5 weeks pre-farrow.

Treatments.

Sows and gilts were randomly assigned to one of four treatments (control (CON) or Newport vaccine treatments 1-3 (VACC) based on the day of breeding and within parity. The formulation was 100 micrograms of each polypeptide: VP4 (SEQ ID NO:42), VP6 (SEQ ID NO:52) and NSP4 (SEQ ID NO:18), which originated from rotavirus isolate 1. These protein subunits were combined with 10% TRIGEN (composed approximately of 1.6% polyoxyethylene sorbitan monooleate, 10% aluminum hydroxide gel, 38% aqueous/saline, 45% purified mineral oil, and 5% sorbitan monooleate) formulated for a 2 cc dose. Animals in the assigned VACC treatment group 1 received 2 ml of vaccine intramuscularly at 3 weeks pre farrow, animals in the assigned VACC treatment group 2 received 2 ml of vaccine intramuscularly at 5 weeks pre farrow and then again 3 weeks pre farrow, animals in the assigned VACC treatment group 3 received 2 ml of vaccine intramuscularly at 7 weeks pre farrow, 5 weeks pre farrow, and then again 3 weeks pre-farrow. All litters from these animals were cross fostered within 24 hours of birth by treatment.

Data Collection.

Scour scores were conducted daily from day of birth to day 5. The individual collecting all data was blinded from the original treatment assignments. Pigs removed from the original litters due to mortality associated with scours were noted on the day of removal and were compiled as mortality/morbidity in the data set.

Data Analysis.

Mortality/morbidity and scour scores were analyzed using GLM procedures. Room and parity were also included in the model.

Results.

Piglet mortality and morbidity was reduced in the group that received two doses of vaccine prior to farrowing compared to their respective control counterparts although not significant. However, in the groups that received either one or three doses of vaccine, there were no differences. Scour scores were only significantly different on Day 1 post-farrow for the two dose vaccination treatment. No other differences were noted in the scour scores at any other time-point or with either the one or three dose program. Interestingly in this study, the vaccine showed reduction using the two dose vaccination program and not the single or triple dose program.

TABLE 2

Performance data measured with 2 dose vaccination.

|  | CON | VACC | P value |
| --- | --- | --- | --- |
| Mortality due to scours, n | 37 | 23 |  |
| Mortality due to scours, % | 1.72 | 1.02 | .19 |
| Fallouts, % | .69 | .92 | .53 |

TABLE 3

Average scour score by day post-farrow with 2 dose vaccination.

|  | CON | VACC | SEM | P value |
| --- | --- | --- | --- | --- |
| Day 1 | .56 | .41 | .06 | .05 |
| Day 2 | .87 | .84 | .07 | .77 |
| Day 3 | 1.01 | 1.00 | .08 | .98 |
| Day 4 | .51 | .40 | .10 | .41 |
| Day 5 | .29 | .24 | .04 | .37 |

TABLE 4

Average scour score by day post-farrow with 3 dose vaccination.

|  | CON | VACC | SEM | P value |
| --- | --- | --- | --- | --- |
| Day 1 | .30 | .32 | .10 | .84 |
| Day 2 | .61 | .40 | .12 | .15 |
| Day 3 | .80 | .76 | .13 | .79 |
| Day 4 | .25 | .15 | .09 | .32 |
| Day 5 | .02 | .00 | .02 | .31 |

Example 5

Production of Triple Fusion Rotavirus C Vaccine

Summary.

As described above, Rota C subunit vaccine production was accomplished by cloning the three different genes (NSP4, VP4 and VP6) into three different vectors and growing three different *E. coli* cultures. To simply this process, all three genes were placed into a single plasmid vector, tandem and in frame, thus enabling vaccine production using a single batch of *E. coli* culture. This construct was built by cloning the Rota C (isolate 12-1260-5) genes into pNPL2 (GST tag in-frame at the N-terminus). The three gene fusion (not including the GST tag) has the sequence as set forth in SEQ ID NO:94. The encoded polyprotein has the sequence as set forth in SEQ ID NO:95.

Materials and Methods.

RNA is extracted from a clinical sample using Qiagen Viral RNA extraction kit as per manufacturer's protocol. The concentration and purity of the RNA was verified by measuring absorbance at 260 and 280 using Nanodrop. The RNA was qualified if the 260/280 ratio was at least 1.7 and concentration of RNA was at least 50 ng/μl. The rotaviral genes were amplified (primers set forth in Table 5) and PCR products were purified using Qiagen PCR purification kit. the size of the products are confirmed by running on a DNA gel (NSP4-300 bp, VP4-750 bp, VP6-1200 bp) and concentration estimated using nanodrop.

TABLE 5

Rota C triple fusion primers

| SEQ ID | Name | Orientation | Sequence |
|---|---|---|---|
| 8 | KSN652 NSP4 | Forward | GGTTCCGCGTGGATCCATCACCTCAAAAACTG |
| 13 | KSN657 VP6 | Reverse | GTGCGGCCGCAAGCTTCTACATCACCATTCTCTTC |
| 96 | KSN859 NSP4 | Reverse | AAGTGAGGACGCCCTTAGACAAACTTCCGTCTCC |
| 97 | KSN860 VP4 | Forward | AGGGCGTCCTCACTTTATC |
| 98 | KSN861 VP4 | Reverse | TGAAAACAGCACGTCTAACACCATCATTCTC |
| 99 | KSN862 VP6 | Forward | GACGTGCTGTTTTCAATTGC |

Cloning of PCR Products into pNPL2.

All three products were simultaneously cloned into the expression vector. The reaction was set up as below and incubated at 50° C. for 15 min following by 4° C. hold. About 5 ul of the reaction products are used to transform CYS21 E. coli competent cells (Cat # GE-STCB-22) as per manufacturer's recommendations (Delphi Genetics). The recombinant E. coli containing the plasmid is grown in LB media and plasmid DNA is sequenced using primers listed the Table 5 along with T7 promoter and T7 terminator primers (standard free primers). Sequences were aligned to generate a large open reading frame and verified for its accuracy; the ORF contained all three genes in frame with GST tag (GST-NSP4-VP4-VP6; about 2.9 kb).

TABLE 6

Triple fusion ligation reaction mixture

| Label | Volume |
|---|---|
| BamH I and Hind III cut pNPL2 (~50 ng/ul) | 3 µl |
| NSP4 PCR product (~50 ng/ul) | 0.5 µl |
| VP4 PCR product (~50 ng/ul) | 1 µl |
| VP6 PCR product (~50 ng/ul) | 1.5 µl |
| 5X Infusion HD cloning mix (Cat # 639646, Clontech) | 2 µl |
| Nuclease free water | 2 µl |

NSP4-VP4-VP6 Polyprotein Expression Analysis.

Figure 12:
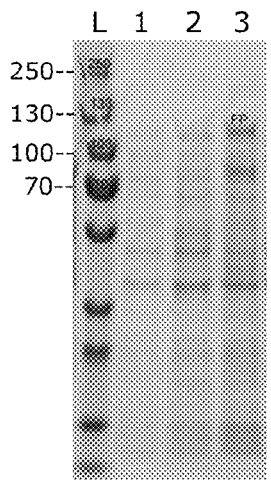
FIG. 12 is a PAGE gel confirming expression of the Rota C NSP4-VP4-VP6 triple fusion protein. L, ladder; 1, before induction (OD=0.6); 2, un-induced cultures (OD=1.5); 3, induced cultures (OD=1.5)
Figure 13:
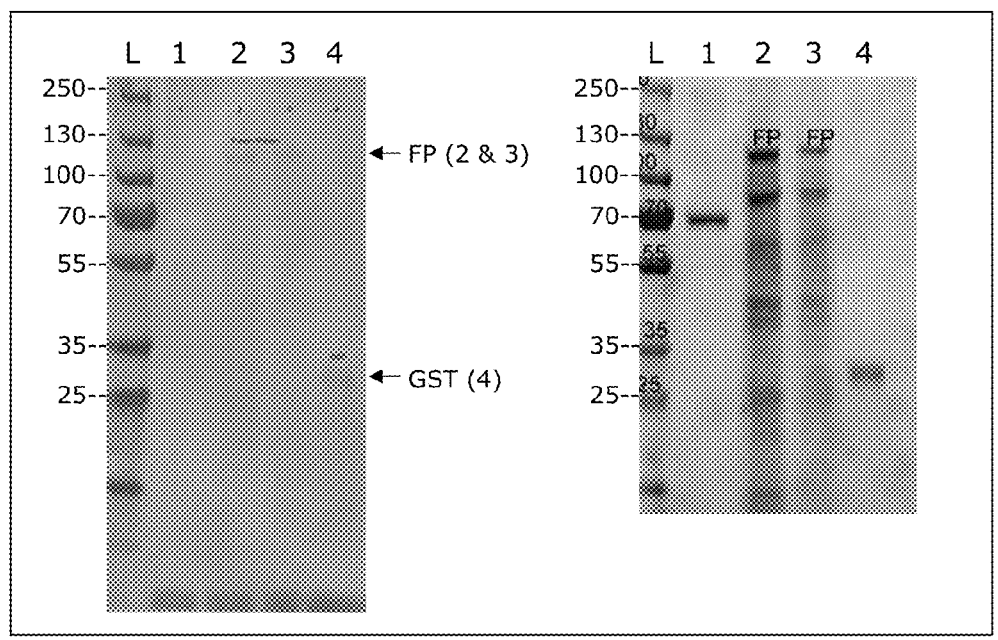
FIG. 13 is a Western blot (left) and PAGE gel (right) confirming fusion protein expression. L-ladder, 1-BSA 1.5 µg, 2-Fusion protein 1:20 diluted, 3-Fusion protein 1:40 diluted, 4-GST 0.5 µg.

Protein expression was induced in the SE1 strain of E. coli by adding IPTG according to standard protocols. The culture fluids were resolved on a PAGE gel to verify expression of the fusion protein (FIG. 12). The fusion protein was present in the urea soluble fraction of the fluids, but not in the B-per solution fraction (PAGE, data not shown). The urea-soluble fusion protein was diluted with water 1:20 and 1:40, and run on a PAGE for subsequent Western blot. The blot was probed using monoclonal antibody against GST (Genscript Cat A00866) at 0.1 µg/mL final concentration using standard protocol (FIG. 13).

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A safe and effective immunological composition comprising:
   a) a recombinant, non-naturally-occurring fusion polypeptide, comprising an NSP4, a VP4 and a VP6 porcine rotavirus C polypeptide; and b) a pharmaceutically or veterinary acceptable vehicle, diluent or excipient;

wherein the composition is effective in eliciting in a porcine animal a protective immune response against a subsequent virulent rotavirus challenge;

wherein the polypeptide has at least 95% sequence identity to the sequence set forth in Seq. Id. No.: 95; and wherein the NSP4 polypeptide has at least 90% identity to the sequence set forth in Seq. Id. No.: 18, the VP4 polypeptide has at least 90% identity to the sequence set forth in Seq. Id. No.: 42, and the VP4 polypeptide has at least 90% identity to the sequence set forth in Seq. Id. No.: 52.

2. The composition of claim 1 further comprising an adjuvant.

3. The composition of claim 2 wherein the adjuvant is an oil-in-water adjuvant.

4. A safe and effective immunological composition comprising:

a) a recombinant, non-naturally-occurring triple polypeptide, consisting essentially of a rotavirus C NSP4-VP4-VP6 triple fusion protein having the sequence set forth in SEQ ID NO:95; and b) a pharmaceutically or veterinary acceptable vehicle, diluent or excipient;

c) an adjuvant comprising mineral oil and surfactants; and wherein the composition is effective in eliciting in a porcine animal in need thereof a protective immune response that is protective against a subsequent virulent rotavirus challenge.

5. The composition of claim 4, further comprising at least one additional antigen associated with a pathogen other than rotavirus.

6. The composition of claim 5, wherein the at least one additional antigen elicits in a porcine an immune response against *Mycoplasma hyopneumoniae* (*M. hyo*), Porcine Circovirus Type 2 (PCV2), Porcine reproductive and respiratory syndrome virus (PRRSV), Swine influenza virus (SIV) or other pathogen capable of infecting and causing illness or susceptibility to illness in a porcine.

7. A method of vaccinating a procine animal, comprising administering to the animal at least one dose of the composition of claim 4.

8. The method of claim 7, wherein the porcine is a sow from about 3 weeks to about 6 weeks prefarrowing.

9. The method of 8, wherein the resulting piglets have a reduced morbidity and/or mortality as compared to piglets coming from unvaccinated sows.

* * * * *

SEQUENCE LISTING

```
<160> NUMBER OF SEQ ID NOS: 99

<210> SEQ ID NO 1
<211> LENGTH: 5932
<212> TYPE: DNA
<213> ORGANISM: Artificial Sequence
<220> FEATURE:
<223> OTHER INFORMATION: pStaby1 plasmid

<400> SEQUENCE: 1
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tccctttagg     180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aacccatct cggtctattc     360 ttttgattta tagggatttt tgccgatttc ggcctattgg ttaaaaatg agctgattta     420
```

```
acaaaaattt aacgcgaatt ttaacaaaat attaacgttt acaatttcag gtggcacttt    480
tcggggaaat gtgcgcggaa cccctatttg tttattttc  taaatacatt caaatatgta    540
tccgctcatg agacaataac cctgataaat gcttcaataa tattgaaaaa ggaagagtat    600
gagtattcaa catttccgtg tcgcccttat tccctttttt gcggcatttt gccttcctgt    660
ttttgctcac ccagaaacgc tggtgaaagt aaaagatgct gaagatcagt tgggtgcacg    720
agtgggttac atcgaactgg atctcaacag cggtaagatc cttgagagtt ttcgccccga    780
agaacgtttt ccaatgatga gcacttttaa agttctgcta tgtggcgcgg tattatcccg    840
tattgacgcc gggcaagagc aactcggtcg ccgcatacac tattctcaga atgacttggt    900
tgagtactca ccagtcacag aaaagcatct tacggatggc atgacagtaa gagaattatg    960
cagtgctgcc ataaccatga gtgataacac tgcggccaac ttacttctga caacgatcgg   1020
aggaccgaag gagctaaccg cttttttgca caacatgggg gatcatgtaa ctcgccttga   1080
tcgttgggaa ccggagctga atgaagccat accaaacgac gagcgtgaca ccacgatgcc   1140
tgcagcaatg gcaacaacgt tgcgcaaact attaactggc gaactactta ctctagcttc   1200
ccggcaacaa ttaatagact ggatggaggc ggataaagtt gcaggaccac ttctgcgctc   1260
ggcccttccg gctggctggt ttattgctga taaatctgga gccggtgagc gtgggtctcg   1320
cggtatcatt gcagcactgg ggccagatgg taagccctcc cgtatcgtag ttatctacac   1380
gacgggagt  caggcaacta tggatgaacg aaatagacag atcgctgaga taggtgcctc   1440
actgattaag cattggtaac tgtcagacca agtttactca tatatacttt agattgattt   1500
aaaacttcat ttttaattta aaaggatcta ggtgaagatc cttttttgata atctcatgac   1560
caaaatccct taacgtgagt tttcgttcca ctgagcgtca gaccccgtag aaaagatcaa   1620
aggatcttct tgagatcctt ttttttctgcg cgtaatctgc tgcttgcaaa caaaaaaacc   1680
accgctacca gcggtggttt gtttgccgga tcaagagcta ccaactcttt ttccgaaggt   1740
aactggcttc agcagagcgc agataccaaa tactgtcctt ctagtgtagc cgtagttagg   1800
ccaccacttc aagaactctg tagcaccgcc tacatacctc gctctgctaa tcctgttacc   1860
agtggctgct gccagtggcg ataagtcgtg tcttaccggg ttggactcaa gacgatagtt   1920
accggataag gcgcagcggt cgggctgaac ggggggttcg tgcacacagc ccagcttgga   1980
gcgaacgacc tacaccgaac tgagatacct acagcgtgag ctatgagaaa gcgccacgct   2040
tcccgaaggg agaaaggcgg acaggtatcc ggtaagcggc agggtcggaa caggagagcg   2100
cacgagggag cttccagggg gaaacgcctg gtatctttat agtcctgtcg ggtttcgcca   2160
cctctgactt gagcgtcgat ttttgtgatg ctcgtcaggg gggcggagcc tatggaaaaa   2220
cgccagcaac gcggcctttt tacggttcct ggccttttgc tggccttttg ctcacatgtt   2280
ctttcctgcg ttatcccctg attctgtgga taaccgtatt accgcctttg agtgagctga   2340
taccgctcgc cgcagccgaa cgaccgagcg cagcgagtca gtgagcgagg aagcggaaga   2400
gcgcctgatg cggtattttc tccttacgca tctgtgcggt atttcacacc gcatatatgg   2460
tgcactctca gtacaatctg ctctgatgcc gcatagttaa gccagtatac actccgctat   2520
cgctacgtga ctgggtcatg gctgcgcccc gacaccgcc  aacacccgct gacgcgccct   2580
gacgggcttg tctgctcccg gcatccgctt acagacaagc tgtgaccgtc tccgggagct   2640
gcatgtgtca gaggttttca ccgtcatcac cgaaacgcgc gaggcagctg cggtaaagct   2700
catcagcgtg tcgtgaagc  gattcacaga tgtctgcctg ttcatccgcg tccagctcgt   2760
tgagtttctc cagaagcgtt aatgtctggc ttctgataaa gcgggccatg ttaagggcgg   2820
```

```
tttttttcctg tttggtcact gatgcctccg tgtaagggqq atttctgttc atgggggtaa    2880
tgataccgat gaaacgagag aggatgctca cgatacgggt tactgatgat gaacatgccc    2940
ggttactgga acgttgtgag ggtaaacaac tggcggtatg gatgcggcgg gaccagagaa    3000
aaatcactca gggtcaatgc cagcgcttcg ttaatacaga tgtaggtgtt ccacagggta    3060
gccagcagca tcctgcgatg cagatccgga acataatggt gcagggcgct gacttccgcg    3120
tttccagact ttacgaaaca cggaaaccga agaccattca tgttgttgct caggtcgcag    3180
acgttttgca gcagcagtcg cttcacgttc gctcgcgtat cggtgattca ttctgctaac    3240
cagtaaggca accccgccag cctagccggg tcctcaacga caggagcacg atcatgcgca    3300
cccgtggggc cgccatgccg gcgataatgg cctgcttctc gccgaaacgt ttggtggcgg    3360
gaccagtgac gaaggcttga gcgagggcgt gcaagattcc gaataccgca agcgacaggc    3420
cgatcatcgt cgcgctccag cgaaagcggt cctcgccgaa aatgacccag agcgctgccg    3480
gcacctgtcc tacgagttgc atgataaaga agacagtcat aagtgcgqcg acgatagtca    3540 tgccccgcgc ccaccggaag gagctgactg ggttgaaggc tctcaagggc atcggtcgag    3600
atcccggtgt ctaatgagtg agctaactta cattaattgc gttgcgctca ctgcccgctt    3660
tccagtcggg aaacctgtcg tgccagctgc attaatgaat cggccaacgc gcggggagag    3720
gcggtttgcg tattgggcgc cagggtggtt tttcttttca ccagtgagac gggcaacagc    3780
tgattgccct tcaccgcctg gccctgagag agttgcagca agcggtccac gctggtttgc    3840
cccagcaggc gaaaatcctg tttgatggtg gttaacggcg ggatataaca tgagctgtct    3900
tcggtatcgt cgtatcccac taccgagata tccgcaccaa cgcgcagccc ggactcggta    3960
atggcgcgca ttgcgcccag cgccatctga tcgttggcaa ccagcatcgc agtgggaacg    4020
atgccctcat tcagcatttg catggtttgt tgaaaaccgg acatggcact ccagtcgcct    4080
tcccgttccg ctatcggctg aatttgattg cgagtgagat attatgcca gccagccaga    4140 cgcagacgcg ccgagacaga acttaatggg cccgctaaca gcgcgatttg ctggtgaccc    4200
aatgcgacca gatgctccac gcccagtcgc gtaccgtctt catgggagaa aataatactg    4260
ttgatgggtg tctggtcaga gacatcaaga ataacgccg gaacattagt gcaggcagct    4320
tccacagcaa tggcatcctg gtcatccagc ggatagttaa tgatcagccc actgacgcgt    4380
tgcgcgagaa gattgtgcac cgccgcttta caggcttcga cgccgcttcg ttctaccatc    4440
gacaccacca cgctggcacc cagttgatcg gcgcgagatt taatcgccgc gacaatttgc    4500
gacggcgcgt gcagggccag actggaggtg caacgccaa tcagcaacga ctgtttgccc    4560
gccagttgtt gtgccacgcg gttgggaatg taattcagct ccgccatcgc cgcttccact    4620 tttcccgcg ttttcgcaga aacgtggctg gcctggttca ccacgcggga aacggtctga    4680
taagagacac cggcatactc tgcgacatcg tataacgtta ctggtttcac attcaccacc    4740
ctgaattgac tctcttccgg cgctatcat gccataccgc gaaaggtttt cgccattcg    4800 atggtgtccg ggatctcgac gctctccctt atgcgactcc tgcattagga agcagcccag    4860
tagtaggttg aggccgttga gcaccgccgc cgcaaggaat ggtgcatgct caccagtccc    4920
tgttctcgtc agcaaaagag ccgttcattt caataaaccg ggcgacctca gccatccctt    4980 cctgatttc cgctttccag cgttcggcac gcagacgacg ggcttcattc tgcatggttg    5040
tgcttaccag accggagata ttgacatcgt atgccttgag caactgatag ctgtcgctgt    5100
caactgtcac tgtaatacgc tgcttcatgc ctgcccctcc cttttggtgt ccaaccggct    5160
```

```
cgacggggc  agcgcaaggc  ggtgcctccg  gcgggccact  caatgcttga  gtatactcac    5220
tagactttgc  ttcgcaaagt  cgtgaccgcc  tacggcggct  gcggcgccct  acgggcttgc    5280
tctccgggct  tcgccctgcg  cggtcgctgc  gctcccttgc  cagcccgtgg  atatgtggac    5340
gatggccgcg  agcggccacc  ggctggtcg   cttcgctcgg  cccgtggaca  acgcatgcaa    5400
ggagatggcg  cccaacagtc  ccccggccac  ggggcctgcc  accataccca  cgccgaaaca    5460
agcgctcatg  agcccgaagt  ggcgagcccg  atcttcccca  tcggtgatgt  cggcgatata    5520
ggcgccagca  accgcacctg  tggcgccggt  gatgccggcc  acgatgcgtc  cggcgtagag    5580
gatcgagatc  tcgatcccgc  gaaattaata  cgactcacta  tagggaatt   gtgagcggat    5640 aacaattccc  ctctagaaat  aattttgttt  aactttaaga  aggagatata  catatggcta    5700
gcatgactgg  tggacagcaa  atgggtcgcg  gatccgaatt  cgagctccgt  cgacaagctt    5760
gcggccgcac  tcgagcacca  ccaccaccac  cactgagatc  cggctgctaa  caaagcccga    5820
aaggaagctg  agttggctgc  tgccaccgct  gagcaataac  tagcataacc  ccttggggcc    5880
tctaaacggg  tcttgagggg  ttttttgctg  aaaggaggaa  ctatatccgg  at            5932
```

<210> SEQ ID NO 2
<211> LENGTH: 29
<212> TYPE: DNA
<213> ORGANISM: Artificial Sequence
<220> FEATURE:
<223> OTHER INFORMATION: GST forward NdeI primer

<400> SEQUENCE: 2
gtccatatgt cccctatact aggttattg                                29

<210> SEQ ID NO 3
<211> LENGTH: 30
<212> TYPE: DNA
<213> ORGANISM: Artificial Sequence
<220> FEATURE:
<223> OTHER INFORMATION: GST Rev. BamHI primer

<400> SEQUENCE: 3
gtcggatccg gatccacgcg gaaccagatc                               30

<210> SEQ ID NO 4
<211> LENGTH: 28
<212> TYPE: DNA
<213> ORGANISM: Artificial Sequence
<220> FEATURE:
<223> OTHER INFORMATION: AMPR gene deletion For. primer

<400> SEQUENCE: 4
actcttcctt tttcaatatt attgaagc                                 28

<210> SEQ ID NO 5
<211> LENGTH: 28
<212> TYPE: DNA
<213> ORGANISM: Artificial Sequence
<220> FEATURE:
<223> OTHER INFORMATION: AMPR gene deletion Rev. primer

<400> SEQUENCE: 5
ctgtcagacc aagtttactc atatatac                                 28

<210> SEQ ID NO 6
<211> LENGTH: 29
<212> TYPE: DNA
<213> ORGANISM: Artificial Sequence

```
<220> FEATURE:
<223> OTHER INFORMATION: PCR Verification For. primer

<400> SEQUENCE: 6
ctcgatcccg cgaaattaat acgactcac                              29

<210> SEQ ID NO 7
<211> LENGTH: 29
<212> TYPE: DNA
<213> ORGANISM: Artificial Sequence
<220> FEATURE:
<223> OTHER INFORMATION: PCR Verification Rev. primer

<400> SEQUENCE: 7
cagccaactc agcttccttt cgggctttg                              29

<210> SEQ ID NO 8
<211> LENGTH: 32
<212> TYPE: DNA
<213> ORGANISM: Artificial Sequence
<220> FEATURE:
<223> OTHER INFORMATION: NSP4 For. with BamHI site primer

<400> SEQUENCE: 8
ggttccgcgt ggatccatca cctcaaaaac tg                          32

<210> SEQ ID NO 9
<211> LENGTH: 37
<212> TYPE: DNA
<213> ORGANISM: Artificial Sequence
<220> FEATURE:
<223> OTHER INFORMATION: NSP4 Rev. with HindIII site

<400> SEQUENCE: 9
gtgcggccgc aagctttcat agacaaactt ccgtctc                     37

<210> SEQ ID NO 10
<211> LENGTH: 35
<212> TYPE: DNA
<213> ORGANISM: Artificial Sequence
<220> FEATURE:
<223> OTHER INFORMATION: VP4 For. with BamHI site primer

<400> SEQUENCE: 10
ggttccgcgt ggatccaggg cgtcctcact ttatc                       35

<210> SEQ ID NO 11
<211> LENGTH: 35
<212> TYPE: DNA
<213> ORGANISM: Artificial Sequence
<220> FEATURE:
<223> OTHER INFORMATION: VP4 Rev. with HindIII site primer

<400> SEQUENCE: 11
gtgcggccgc aagcttttat aacaccatca ttctc                       35

<210> SEQ ID NO 12
<211> LENGTH: 35
<212> TYPE: DNA
<213> ORGANISM: Artificial Sequence
<220> FEATURE:
<223> OTHER INFORMATION: VP6 For. with BamHI site primer

<400> SEQUENCE: 12
ggttccgcgt ggatccgacg tgctgttttc aattg                       35
```

<210> SEQ ID NO 13
<211> LENGTH: 35
<212> TYPE: DNA
<213> ORGANISM: Artificial Sequence
<220> FEATURE:
<223> OTHER INFORMATION: VP6 Rev. with HindIII site primer

<400> SEQUENCE: 13
gtgcggccgc aagcttctac atcaccattc tcttc                          35

<210> SEQ ID NO 14
<211> LENGTH: 5071
<212> TYPE: DNA
<213> ORGANISM: Artificial Sequence
<220> FEATURE:
<223> OTHER INFORMATION: pNPL1 plasmid (pStaby1 less the AmpR gene)

<400> SEQUENCE: 14
tggcgaatgg gacgcgccct gtagcggcgc attaagcgcg gcgggtgtgg tggttacgcg    60
cagcgtgacc gctacacttg ccagcgccct agcgcccgct cctttcgctt tcttcccttc   120
ctttctcgcc acgttcgccg gctttccccg tcaagctcta atcggggggc tccctttagg   180
gttccgattt agtgctttac ggcacctcga ccccaaaaaa cttgattagg gtgatggttc   240
acgtagtggg ccatcgccct gatagacggt ttttcgccct ttgacgttgg agtccacgtt   300
ctttaatagt ggactcttgt tccaaactgg aacaacactc aaccctatct cggtctattc   360
ttttgattta agggattt tgccgatttc ggcctattgg ttaaaaaatg agctgattta    420
acaaaaattt aacgcgaatt ttaacaaaat attaacgttt acaatttcag gtggcacttt   480
tcggggaaat gtgcgcggaa cccctatttg tttatttttc taaatacatt caaatatgta   540
tccgctcatg agacaataac cctgataaat gcttcaataa tattgaaaaa ggaagagtct   600
gtcagaccaa gtttactcat atatacttta gattgattta aaacttcatt tttaatttaa   660
aaggatctag gtgaagatcc ttttttgataa tctcatgacc aaaatccctt aacgtgagtt   720
ttcgttccac tgagcgtcag accccgtaga aaagatcaaa ggatcttctt gagatccttt   780
ttttctgcgc gtaatctgct gcttgcaaac aaaaaaacca ccgctaccag cggtggtttg   840
tttgccggat caagagctac caactctttt tccgaaggta actggcttca gcagagcgca   900
gataccaaat actgtccttc tagtgtagcc gtagttaggc caccacttca agaactctgt   960
agcaccgcct acatacctcg ctctgctaat cctgttacca gtggctgctg ccagtggcga  1020
taagtcgtgt cttaccgggt tggactcaag acgatagtta ccggataagg cgcagcggtc  1080
gggctgaacg gggggttcgt gcacacagcc cagcttggag cgaacgacct acaccgaact  1140
gagataccta cagcgtgagc tatgagaaag cgccacgctt cccgaaggga gaaaggcgga  1200
caggtatccg gtaagcggca gggtcggaac aggagagcgc acgagggagc ttccaggggg  1260
aaacgcctgg tatctttata gtcctgtcgg gtttcgccac ctctgacttg agcgtcgatt  1320
tttgtgatgc tcgtcagggg ggcggagcct atggaaaaac gccagcaacg cggccttttt  1380
acggttcctg gccttttgct ggccttttgc tcacatgttc tttcctgcgt tatcccctga  1440
ttctgtggat aaccgtatta ccgcctttga gtgagctgat accgctcgcc gcagccgaac  1500
gaccgagcgc agcgagtcag tgagcgagga agcggaagag cgcctgatgc ggtatttttct  1560 ccttacgcat ctgtgcggta tttcacaccg catatatggt gcactctcag tacaatctgc  1620
tctgatgccg catagttaag ccagtataca ctccgctatc gctacgtgac tgggtcatgg  1680
ctgcgccccg acacccgcca acacccgctg acgcgccctg acgggcttgt ctgctcccgg  1740

```
catccgctta cagacaagct gtgaccgtct ccgggagctg catgtgtcag aggttttcac    1800
cgtcatcacc gaaacgcgcg aggcagctgc ggtaaagctc atcagcgtgg tcgtgaagcg    1860
attcacagat gtctgcctgt tcatccgcgt ccagctcgtt gagtttctcc agaagcgtta    1920
atgtctggct tctgataaag cgggccatgt taagggcggt tttttcctgt ttggtcactg    1980
atgcctccgt gtaaggggga tttctgttca tgggggtaat gataccgatg aaacgagaga    2040
ggatgctcac gatacgggtt actgatgatg aacatgcccg gttactggaa cgttgtgagg    2100
gtaaacaact ggcggtatgg atgcggcggg accagagaaa aatcactcag gtcaatgcc     2160 agcgcttcgt taatacagat gtaggtgttc cacagggtag ccagcagcat cctgcgatgc    2220
agatccggaa cataatggtg cagggcgctg acttccgcgt ttccagactt tacgaaacac    2280
ggaaaccgaa gaccattcat gttgttgctc aggtcgcaga cgttttgcag cagcagtcgc    2340
ttcacgttcg ctcgcgtatc ggtgattcat tctgctaacc agtaaggcaa ccccgccagc    2400
ctagccgggt cctcaacgac aggagcacga tcatgcgcac ccgtggggcc gcatgccgg     2460 cgataatggc ctgcttctcg ccgaaacgtt tggtggcggg accagtgacg aaggcttgag    2520
cgagggcgtg caagattccg aataccgcaa gcgacaggcc gatcatcgtc gcgctccagc    2580
gaaagcggtc ctcgccgaaa atgacccaga gcgctgccgg cacctgtcct acgagttgca    2640
tgataaagaa gacagtcata agtgcggcga cgatagtcat gccccgcgcc accggaagg     2700 agctgactgg gttgaaggct ctcaagggca tcggtcgaga tcccggtgcc taatgagtga    2760
gctaacttac attaattgcg ttgcgctcac tgcccgcttt ccagtcggga aacctgtcgt    2820
gccagctgca ttaatgaatc ggccaacgcg cggggagagg cggtttgcgt attgggcgcc    2880
agggtggttt ttcttttcac cagtgagacg ggcaacagct gattgcccct caccgcctgg    2940
ccctgagaga gttgcagcaa gcggtccacg ctggtttgcc ccagcaggcg aaaatcctgt    3000
ttgatggtgg ttaacggcgg gatataacat gagctgtctt cggtatcgtc gtatcccact    3060
accgagatat ccgcaccaac gcgcagcccg gactcggtaa tggcgcgcat tgcgcccagc    3120
gccatctgat cgttggcaac cagcatcgca gtgggaacga tgccctcatt cagcatttgc    3180
atggtttgtt gaaaaccgga catggcactc cagtcgcctt cccgttccgc tatcggctga    3240
atttgattgc gagtgagata tttatgccag ccagccagac gcagacgcgc cgagacagaa    3300
cttaatgggc ccgctaacag cgcgatttgc tggtgaccca atgcgaccag atgctccacg    3360
cccagtcgcg taccgtcttc atgggagaaa ataatactgt tgatgggtgt ctggtcagag    3420
acatcaagaa ataacgccgg aacattagtg caggcagctt ccacagcaat ggcatcctgg    3480
tcatccagcg gatagttaat gatcagccca ctgacgcgtt gcgcgagaag attgtgcacc    3540
gccgctttac aggcttcgac gccgcttcgt tctaccatcg acaccaccac gctggcaccc    3600
agttgatcgg cgcgagattt aatcgccgcg acaatttgcg acggcgcgtg cagggccaga    3660
ctggaggtgg caacgccaat cagcaacgac tgtttgcccg ccagttgttg tgccacgcgg    3720
ttgggaatgt aattcagctc cgccatcgcc gcttccactt ttcccgcgt tttcgcagaa     3780 acgtggctgg cctggttcac cacgcgggaa acggtctgat aagagacacc ggcatactct    3840
gcgacatcgt ataacgttac tggtttcaca ttcaccaccc tgaattgact ctcttccggg    3900
cgctatcatg ccataccgcg aaaggttttg cgccattcga tggtgtccgg gatctcgacg    3960
ctctccctta tgcgactcct gcattaggaa gcagcccagt agtaggttga ggccgttgag    4020
caccgccgcc gcaaggaatg gtgcatgctc accagtccct gttctcgtca gcaaaagagc    4080
```

```
cgttcatttc aataaaccgg gcgacctcag ccatcccttc ctgattttcc gctttccagc    4140
gttcggcacg cagacgacgg gcttcattct gcatggttgt gcttaccaga ccggagatat    4200
tgacatcgta tgccttgagc aactgatagc tgtcgctgtc aactgtcact gtaatacgct    4260
gcttcatgcc tgcccctccc ttttggtgtc aaccggctc gacggggca gcgcaaggcg      4320 gtgcctccgg cgggccactc aatgcttgag tatactcact agactttgct tcgcaaagtc    4380
gtgaccgcct acgcggctg cggcgcccta cgggcttgct ctccgggctt cgccctgcgc     4440
ggtcgctgcg ctcccttgcc agcccgtgga tatgtggacg atggccgcga gcggccaccg    4500
gctggctcgc ttcgctcggc ccgtggacaa cgcatgcaag gagatggcgc caacagtcc     4560 cccggccacg gggcctgcca ccatacccac gccgaaacaa gcgctcatga gcccgaagtg    4620
gcgagcccga tcttccccat cggtgatgtc ggcgatatag gcgccagcaa ccgcacctgt    4680
ggcgccggtg atgccggcca cgatgcgtcc ggcgtagagg atcgagatct cgatcccgcg    4740
aaattaatac gactcactat aggggaattg tgagcggata caattcccc tctagaaata    4800 attttgttta actttaagaa ggagatatac atatggctag catgactggt ggacagcaaa    4860
tgggtcgcgg atccgaattc gagctccgtc gacaagcttg cggccgcact cgagcaccac    4920
caccaccacc actgagatcc ggctgctaac aaagcccgaa aggaagctga gttggctgct    4980
gccaccgctg agcaataact agcataaccc cttggggcct ctaaacgggt cttgaggggt    5040
tttttgctga aaggaggaac tatatccgga t                                    5071
```

```
<210> SEQ ID NO 15
<211> LENGTH: 5707
<212> TYPE: DNA
<213> ORGANISM: Artificial Sequence
<220> FEATURE:
<223> OTHER INFORMATION: pNPL2 SEQ ID NO:15

<400> SEQUENCE: 15
```

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc    120
ctttctcgcc acgttcgccg gctttccccg tcaagctcta aatcgggggc tccctttagg    180
gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta agggatttt gccgatttc ggcctattgg ttaaaaatg agctgattta       420 acaaaatt aacgcgaatt ttaacaaaat attaacgttt acaatttcag gtggcacttt     480
tcggggaaat gtgcgcggaa cccctatttg tttattttc taaatacatt caaatatgta     540
tccgctcatg agacaataac cctgataaat gcttcaataa tattgaaaa ggaagagtct    600 gtcagaccaa gtttactcat atactttta gattgattta aacttcatt tttaatttaa     660 aaggatctag gtgaagatcc ttttgataa tctcatgacc aaaatccctt aacgtgagtt    720 tcgttccac tgagcgtcag accccgtaga aagatcaaa ggatcttctt gagatccttt     780
ttttctgcgc gtaatctgct gcttgcaaac aaaaaaacca ccgctaccag cggtggttg    840 tttgccggat caagagctac caactctttt tccgaaggta actggcttca gcagagcgca    900
gataccaaat actgtccttc tagtgtagcc gtagttaggc caccacttca gaactctgt     960 agcaccgcct acatacctcg ctctgctaat cctgttacca gtggctgctg ccagtggcga   1020
taagtcgtgt cttaccgggt tggactcaag acgatagtta ccggataagg cgcagcggtc   1080
```

```
gggctgaacg gggggttcgt gcacacagcc cagcttggag cgaacgacct acaccgaact   1140
gagataccta cagcgtgagc tatgagaaag cgccacgctt cccgaaggga gaaaggcgga   1200
caggtatccg gtaagcggca gggtcggaac aggagagcgc acgagggagc ttccaggggg   1260
aaacgcctgg tatctttata gtcctgtcgg gtttcgccac ctctgacttg agcgtcgatt   1320
tttgtgatgc tcgtcagggg ggcggagcct atggaaaaac gccagcaacg cggcctttt   1380
acggttcctg gccttttgct ggccttttgc tcacatgttc tttcctgcgt tatccctga   1440
ttctgtggat aaccgtatta ccgcctttga gtgagctgat accgctcgcc gcagccgaac   1500
gaccgagcgc agcgagtcag tgagcgagga agcggaagag cgcctgatgc ggtattttct   1560
ccttacgcat ctgtgcggta tttcacaccg catatatggt gcactctcag tacaatctgc   1620
tctgatgccg catagttaag ccagtataca ctccgctatc gctacgtgac tgggtcatgg   1680
ctgcgcccg acaccgcca acacccgctg acgcgccctg acgggcttgt ctgctcccgg   1740
catccgctta cagacaagct gtgaccgtct ccgggagctg catgtgtcag aggttttcac   1800
cgtcatcacc gaaacgcgcg aggcagctgc ggtaaagctc atcagcgtgg tcgtgaagcg   1860
attcacagat gtctgcctgt tcatccgcgt ccagctcgtt gagtttctcc agaagcgtta   1920
atgtctggct tctgataaag cgggccatgt taagggcggt ttttcctgt ttggtcactg   1980
atgcctccgt gtaaggggga tttctgttca tgggggtaat gataccgatg aaacgagaga   2040
ggatgctcac gatacgggtt actgatgatg aacatgcccg gttactggaa cgttgtgagg   2100
gtaaacaact ggcggtatgg atgcggcggg accagagaaa aatcactcag ggtcaatgcc   2160
agcgcttcgt taatacagat gtaggtgttc cacagggtag ccagcagcat cctgcgatgc   2220
agatccggaa cataatggtg cagggcgctg acttccgcgt ttccagactt tacgaaacac   2280
ggaaaccgaa gaccattcat gttgttgctc aggtcgcaga cgttttgcag cagcagtcgc   2340
ttcacgttcg ctcgcgtatc ggtgattcat tctgctaacc agtaaggcaa ccccgccagc   2400
ctagccgggt cctcaacgac aggagcacga tcatgcgcac ccgtggggcc gccatgccgg   2460
cgataatggc ctgcttctcg ccgaaacgtt tggtggcggg accagtgacg aaggcttgag   2520
cgagggcgtg caagattccg aataccgcaa gcgacaggcc gatcatcgtc gcgctccagc   2580
gaaagcggtc ctcgccgaaa atgacccaga gcgctgccgg cacctgtcct acgagttgca   2640
tgataaagaa gacagtcata agtgcggcga cgatagtcat gccccgcgcc caccggaagg   2700
agctgactgg gttgaaggct ctcaagggca tcggtcgaga tcccggtgcc taatgagtga   2760
gctaacttac attaattgcg ttgcgctcac tgcccgcttt ccagtcggga aacctgtcgt   2820
gccagctgca ttaatgaatc ggccaacgcg cggggagagg cggtttgcgt attgggcgcc   2880
agggtggttt tcttttcac cagtgagacg ggcaacagct gattgccctt caccgcctgg   2940
ccctgagaga gttgcagcaa gcggtccacg ctggtttgcc ccagcaggcg aaaatcctgt   3000
ttgatggtgg ttaacggcgg gatataacat gagctgtctt cggtatcgtc gtatcccact   3060
accgagatat ccgcaccaac gcgcagcccg gactcggtaa tggcgcgcat tgcgcccagc   3120
gccatctgat cgttggcaac cagcatcgca gtgggaacga tgccctcatt cagcatttgc   3180
atggtttgtt gaaaaccgga catggcactc cagtcgcctt cccgttccgc tatcggctga   3240
atttgattgc gagtgagata tttatgccag ccagccagac gcagacgcgc cgagacagaa   3300
cttaatgggc ccgctaacag cgcgatttgc tggtgaccca atgcgaccag atgctccacg   3360
cccagtcgcg taccgtcttc atgggagaaa ataatactgt tgatgggtgt ctggtcagag   3420
```

```
acatcaagaa ataacgccgg aacattagtg caggcagctt ccacagcaat ggcatcctgg    3480
tcatccagcg gatagttaat gatcagccca ctgacgcgtt gcgcgagaag attgtgcacc    3540
gccgctttac aggcttcgac gccgcttcgt tctaccatcg acaccaccac gctggcaccc    3600
agttgatcgg cgcgagattt aatcgccgcg acaatttgcg acggcgcgtg cagggccaga    3660
ctggaggtgg caacgccaat cagcaacgac tgtttgcccg ccagttgttg tgccacgcgg    3720
ttgggaatgt aattcagctc cgccatcgcc gcttccactt tttcccgcgt tttcgcagaa    3780
acgtggctgg cctggttcac cacgcgggaa acggtctgat aagagacacc ggcatactct    3840
gcgacatcgt ataacgttac tggtttcaca ttcaccaccc tgaattgact ctcttccggg    3900
cgctatcatg ccataccgcg aaaggttttg cgccattcga tggtgtccgg gatctcgacg    3960
ctctcccttA tgcgactcct gcattaggaa gcagcccagt agtaggttga ggccgttgag    4020
caccgccgcc gcaaggaatg gtgcatgctc accagtccct gttctcgtca gcaaaagagc    4080
cgttcatttc aataaaccgg gcgacctcag ccatcccttc ctgattttcc gctttccagc    4140
gttcggcacg cagacgacgg gcttcattct gcatggttgt gcttaccaga ccggagatat    4200
tgacatcgta tgccttgagc aactgatagc tgtcgctgtc aactgtcact gtaatacgct    4260
gcttcatgcc tgcccctccc ttttggtgtc caaccggctc gacggggggca gcgcaaggcg    4320 gtgcctccgg cgggccactc aatgcttgag tatactcact agactttgct tcgcaaagtc    4380
gtgaccgcct acgcggctg cggcgcccta cgggcttgct ctccgggctt cgccctgcgc    4440
ggtcgctgcg ctcccttgcc agcccgtgga tatgtggacg atggccgcga gcggccaccg    4500
gctggctcgc ttcgctcggc ccgtggacaa cgcatgcaag gagatggcgc caacagtcc    4560 cccggccacg gggcctgcca ccatacccac gccgaaacaa gcgctcatga gcccgaagtg    4620
gcgagcccga tcttccccat cggtgatgtc ggcgatatag gcgccagcaa ccgcacctgt    4680
ggcgccggtg atgccggcca cgatgcgtcc ggcgtagagg atcgagatct cgatcccgcg    4740
aaattaatac gactcactat aggggaattg tgagcggata acaattcccc tctagaaata    4800
attttgttta actttaagaa ggagatatac atatgtcccc tatactaggt tattggaaaa    4860
ttaagggcct tgtgcaaccc actcgacttc ttttggaata tcttgaagaa aaatatgaag    4920
agcatttgta tgagcgcgat gaaggtgata atggcgaaa caaaaagttt gaattgggtt    4980
tggagtttcc caatcttcct tattatattg atggtgatgt taaattaaca cagtctatgg    5040
ccatcatacg ttatatagct gacaagcaca acatgttggg tggttgtcca aaagagcgtg    5100
cagagatttc aatgcttgaa ggagcggttt tggatattag atacggtgtt tcgagaattg    5160
catatagtaa agactttgaa actctcaaag ttgatttct tagcaagcta cctgaaatgc    5220
tgaaaatgtt cgaagatcgt ttatgtcata aaacatattt aaatggtgat catgtaaccc    5280
atcctgactt catgttgtat gacgctcttg atgttgtttt atacatggac ccaatgtgcc    5340
tggatgcgtt cccaaaatta gtttgtttta aaaaacgtat tgaagctatc ccacaaattg    5400
ataagtactt gaaatccagc aagtatatag catggccttt gcagggctgg caagccacgt    5460
ttggtggtgg cgaccatcct ccaaaatcgg atctggttcc gcgtggatcc gaattcgagc    5520
tccgtcgaca gcttgcggc cgcactcgag caccaccacc accaccactg agatccggct    5580
gctaacaaag cccgaaagga agctgagttg gctgctgcca ccgctgagca ataactagca    5640 taacccttg gggcctctaa acgggtcttg aggggttttt tgctgaaagg aggaactata    5700
tccggat                                                             5707
```

<210> SEQ ID NO 16
<211> LENGTH: 687
<212> TYPE: DNA
<213> ORGANISM: Artificial Sequence
<220> FEATURE:
<223> OTHER INFORMATION: GST amplicon produced using SEQ ID NOs 2 and 3
      (primers)

<400> SEQUENCE: 16

```
gtccatatgt cccctatact aggttattgg aaaattaagg gccttgtgca acccactcga    60
cttcttttgg aatatcttga agaaaaatat gaagagcatt tgtatgagcg cgatgaaggt   120
gataaatggc gaaacaaaaa gtttgaattg ggtttggagt ttcccaatct tccttattat   180
attgatggtg atgttaaatt aacacagtct atggccatca tacgttatat agctgacaag   240
cacaacatgt tgggtggttg tccaaaagag cgtgcagaga tttcaatgct gaaggagcg    300
gttttggata ttagatacgg tgtttcgaga attgcatata gtaaagactt tgaaactctc   360
aaagttgatt tcttagcaa gctacctgaa atgctgaaaa tgttcgaaga tcgtttatgt   420
cataaaacat atttaaatgg tgatcatgta acccatcctg acttcatgtt gtatgacgct   480
cttgatgttg ttttatacat ggacccaatg tgcctggatg cgttcccaaa attagtttgt   540
tttaaaaaac gtattgaagc tatcccacaa attgataagt acttgaaatc cagcaagtat   600
atagcatggc ctttgcaggg ctggcaagcc acgtttggtg gtggcgacca tcctccaaaa   660
tcggatctgg ttccgcgtgg atccgac                                       687
```

<210> SEQ ID NO 17
<211> LENGTH: 297
<212> TYPE: DNA
<213> ORGANISM: Artificial Sequence
<220> FEATURE:
<223> OTHER INFORMATION: NSP4 isolate 1

<400> SEQUENCE: 17

```
atcaccctcaa aaactgtgat tggtaaattc aagactgaaa acaatattag tcatcagaat    60
gacgacattc ataaagaata tgaagaggtg atgaaacaaa tgcgtgacat gagagttcat   120
gtaactgcac tatttaatag tatacataag gataatatgg agtggagaat gagtgaatcg   180
attcgcagag aaaagaagcg tgaaatgaaa acaaatacgg tcgagaatga agttaagaat   240
cacgtagatg atgtaaatat atgtggtacg tctggattag agacggaagt ttgtcta    297
```

<210> SEQ ID NO 18
<211> LENGTH: 99
<212> TYPE: PRT
<213> ORGANISM: Artificial Sequence
<220> FEATURE:
<223> OTHER INFORMATION: NSP4 isolate 1

<400> SEQUENCE: 18

```
Ile Thr Ser Lys Thr Val Ile Gly Lys Phe Lys Thr Glu Asn Asn Ile
1               5                  10                  15

Ser His Gln Asn Asp Asp Ile His Lys Glu Tyr Glu Glu Val Met Lys
            20                  25                  30

Gln Met Arg Asp Met Arg Val His Val Thr Ala Leu Phe Asn Ser Ile
        35                  40                  45

His Lys Asp Asn Met Glu Trp Arg Met Ser Glu Ser Ile Arg Arg Glu
    50                  55                  60

Lys Lys Arg Glu Met Lys Thr Asn Thr Val Glu Asn Glu Val Lys Asn
65                  70                  75                  80
```

His Val Asp Asp Val Asn Ile Cys Gly Thr Ser Gly Leu Glu Thr Glu
                85                  90                  95

Val Cys Leu

<210> SEQ ID NO 19
<211> LENGTH: 297
<212> TYPE: DNA
<213> ORGANISM: Artificial Sequence
<220> FEATURE:
<223> OTHER INFORMATION: NSP4 Isolate 63

<400> SEQUENCE: 19
atcacctcaa agactgtgat tagtaagttc aagactgaaa atgacattag ccaccagaac    60
aatgatatca ataaggaata tgaagaggtg atgaaacaaa tgcgtgaaat gagagttcat   120
atgactgcat tatttaatag tatacataaa gataatatgg agtggagaat gagtgaatca   180
attcgcagag aaaagaagcg tgaaatgaaa tcaaatacaa ccgggaatga agtcaagaat   240
cacaccaatg atgtaaatgt atgtgatacg tctggattag agacggaggt ttgtcta      297

<210> SEQ ID NO 20
<211> LENGTH: 99
<212> TYPE: PRT
<213> ORGANISM: Artificial Sequence
<220> FEATURE:
<223> OTHER INFORMATION: NSP4 Isolate 63

<400> SEQUENCE: 20

Ile Thr Ser Lys Thr Val Ile Ser Lys Phe Lys Thr Glu Asn Asp Ile
1               5                   10                  15

Ser His Gln Asn Asn Asp Ile Asn Lys Glu Tyr Glu Glu Val Met Lys
                20                  25                  30

Gln Met Arg Glu Met Arg Val His Met Thr Ala Leu Phe Asn Ser Ile
            35                  40                  45

His Lys Asp Asn Met Glu Trp Arg Met Ser Glu Ser Ile Arg Arg Glu
        50                  55                  60

Lys Lys Arg Glu Met Lys Ser Asn Thr Thr Gly Asn Glu Val Lys Asn
65                  70                  75                  80

His Thr Asn Asp Val Asn Val Cys Asp Thr Ser Gly Leu Glu Thr Glu
                85                  90                  95

Val Cys Leu

<210> SEQ ID NO 21
<211> LENGTH: 297
<212> TYPE: DNA
<213> ORGANISM: Artificial Sequence
<220> FEATURE:
<223> OTHER INFORMATION: NSP4 Isolate 64

<400> SEQUENCE: 21
atcacctcaa agactgtgat tagtaagttc aagactgaaa atgacattag ccaccagaac    60
aacgatatca ataaggaata tgaagaggtg atgaaacaaa tgcgtgaaat gagagttcat   120
atgactgcat tatttaatag tatacataaa gataatatgg aatggagaat gagtgaatca   180
attcgcagag aaaagaagcg tgaaatgaaa tcaaatgcaa ccgggaatga agtcaagatt   240
cacaccaatg atgtaaatgt atgtgatacg tctggattag agacggaggt ttgtcta      297

<210> SEQ ID NO 22
<211> LENGTH: 99
<212> TYPE: PRT

```
<213> ORGANISM: Artificial Sequence
<220> FEATURE:
<223> OTHER INFORMATION: NSP4 Isolate 64

<400> SEQUENCE: 22

Ile Thr Ser Lys Thr Val Ile Ser Lys Phe Lys Thr Glu Asn Asp Ile
1               5                   10                  15

Ser His Gln Asn Asn Asp Ile Asn Lys Glu Tyr Glu Val Met Lys
            20                  25                  30

Gln Met Arg Glu Met Arg Val His Met Thr Ala Leu Phe Asn Ser Ile
            35                  40                  45

His Lys Asp Asn Met Glu Trp Arg Met Ser Glu Ser Ile Arg Arg Glu
        50                  55                  60

Lys Lys Arg Glu Met Lys Ser Asn Ala Thr Gly Asn Glu Val Lys Ile
65                  70                  75                  80

His Thr Asn Asp Val Asn Val Cys Asp Thr Ser Gly Leu Glu Thr Glu
                85                  90                  95

Val Cys Leu

<210> SEQ ID NO 23
<211> LENGTH: 297
<212> TYPE: DNA
<213> ORGANISM: Artificial Sequence
<220> FEATURE:
<223> OTHER INFORMATION: NSP4 Isolate 66

<400> SEQUENCE: 23
atcacctcaa agactgtgat tagtaagttc aagactgaaa atgacattag ccaccagaac      60
aacgatatca ataaggaata tgaagaggtg atgaaacaaa tgcgtgaaat gagagttcat     120
atgactgcat tatttaatag tatacataaa gataatatgg agtggagaat gagtgaatca     180
attcgcagag aaaagaagcg tgaaatgaaa tcaaatgcaa ccgggaatga agtcaagatt     240
cacaccaatg atgtaaatgt atgtgatacg tctggattag agacggaggt ttgtcta        297

<210> SEQ ID NO 24
<211> LENGTH: 99
<212> TYPE: PRT
<213> ORGANISM: Artificial Sequence
<220> FEATURE:
<223> OTHER INFORMATION: NSP4 Isolate 66

<400> SEQUENCE: 24

Ile Thr Ser Lys Thr Val Ile Ser Lys Phe Lys Thr Glu Asn Asp Ile
1               5                   10                  15

Ser His Gln Asn Asn Asp Ile Asn Lys Glu Tyr Glu Val Met Lys
            20                  25                  30

Gln Met Arg Glu Met Arg Val His Met Thr Ala Leu Phe Asn Ser Ile
            35                  40                  45

His Lys Asp Asn Met Glu Trp Arg Met Ser Glu Ser Ile Arg Arg Glu
        50                  55                  60

Lys Lys Arg Glu Met Lys Ser Asn Ala Thr Gly Asn Glu Val Lys Ile
65                  70                  75                  80

His Thr Asn Asp Val Asn Val Cys Asp Thr Ser Gly Leu Glu Thr Glu
                85                  90                  95

Val Cys Leu

<210> SEQ ID NO 25
<211> LENGTH: 297
```

<212> TYPE: DNA
<213> ORGANISM: Artificial Sequence
<220> FEATURE:
<223> OTHER INFORMATION: NSP4 Isolate 67

<400> SEQUENCE: 25

```
atcacctcaa agactgtgat tagtaagttc aagactgaaa atgacattag ccaccagaac    60
aacgatatca ataaggaata tgaagaggta atgaaacaaa tgcgtgaaat gagagttcat   120
atgactgcat tatttaatag tatacataaa gataatatgg agtggagaat gagtgaatca   180
attcgcagag aaaagaagcg tgaaatgaaa tcaaatgcaa ccgggaatga agtcaagaat   240
cacaccaatg atgtaaatgt atgtgatacg tctggattag atggaggt ttgtcta        297
```

<210> SEQ ID NO 26
<211> LENGTH: 99
<212> TYPE: PRT
<213> ORGANISM: Artificial Sequence
<220> FEATURE:
<223> OTHER INFORMATION: NSP4 Isolate 67

<400> SEQUENCE: 26

```
Ile Thr Ser Lys Thr Val Ile Ser Lys Phe Lys Thr Glu Asn Asp Ile
1               5                  10                  15

Ser His Gln Asn Asn Asp Ile Asn Lys Glu Tyr Glu Glu Val Met Lys
            20                  25                  30

Gln Met Arg Glu Met Arg Val His Met Thr Ala Leu Phe Asn Ser Ile
        35                  40                  45

His Lys Asp Asn Met Glu Trp Arg Met Ser Glu Ser Ile Arg Arg Glu
    50                  55                  60

Lys Lys Arg Glu Met Lys Ser Asn Ala Thr Gly Asn Glu Val Lys Asn
65                  70                  75                  80

His Thr Asn Asp Val Asn Val Cys Asp Thr Ser Gly Leu Glu Met Glu
                85                  90                  95

Val Cys Leu
```

<210> SEQ ID NO 27
<211> LENGTH: 297
<212> TYPE: DNA
<213> ORGANISM: Artificial Sequence
<220> FEATURE:
<223> OTHER INFORMATION: NSP4 Isolate 68

<400> SEQUENCE: 27

```
atcacctcaa agactgtgat tagtaagttc aagactgaaa atgacattag ccaccagaac    60
aacgatatca ataaggaata tgaagaggtg atgaaacaaa tgcgtgaaat gagagttcat   120
atgactgcat tatttaatag tatacataaa gataatatgg agtggagaat gagtgaatca   180
atccgcagag aaaagaagcg tgaaatgaaa tcaaatgcaa ccgggaatga agtcaagaat   240
cacacgaatg atgtaaatgt atgtgatacg tctggattag agacggaggt ttgtcta      297
```

<210> SEQ ID NO 28
<211> LENGTH: 99
<212> TYPE: PRT
<213> ORGANISM: Artificial Sequence
<220> FEATURE:
<223> OTHER INFORMATION: NSP4 Isolate 68

<400> SEQUENCE: 28

```
Ile Thr Ser Lys Thr Val Ile Ser Lys Phe Lys Thr Glu Asn Asp Ile
1               5                  10                  15
```

Ser His Gln Asn Asn Asp Ile Asn Lys Glu Tyr Glu Glu Val Met Lys
            20                  25                  30

Gln Met Arg Glu Met Arg Val His Met Thr Ala Leu Phe Asn Ser Ile
        35                  40                  45

His Lys Asp Asn Met Glu Trp Arg Met Ser Glu Ser Ile Arg Arg Glu
 50                  55                  60

Lys Lys Arg Glu Met Lys Ser Asn Ala Thr Gly Asn Glu Val Lys Asn
65                  70                  75                  80

His Thr Asn Asp Val Asn Val Cys Asp Thr Ser Gly Leu Glu Thr Glu
                85                  90                  95

Val Cys Leu

<210> SEQ ID NO 29
<211> LENGTH: 297
<212> TYPE: DNA
<213> ORGANISM: Artificial Sequence
<220> FEATURE:
<223> OTHER INFORMATION: NSP4 Isolate 69

<400> SEQUENCE: 29
atcacctcga agactgtgat tagtaagttc aagactgaaa atgacattag ccaccagaac      60
aacgatatca ataaggaata tgaagaggtg atgaaacaaa tgcgtgaaat gagagttcat     120
atgactgcat tatttaatag tatacataaa gataatatgg agtggagaat gagtgaatca     180
atccgcagag aaaagaagcg tgaaatgaaa tcaaatgcaa ccgggaatga agtcaagaat     240
cacaccaatg atgtaaatgt atgtgatacg tctggattag agacggaggt ttgtcta       297

<210> SEQ ID NO 30
<211> LENGTH: 99
<212> TYPE: PRT
<213> ORGANISM: Artificial Sequence
<220> FEATURE:
<223> OTHER INFORMATION: NSP4 Isolate 69

<400> SEQUENCE: 30

Ile Thr Ser Lys Thr Val Ile Ser Lys Phe Lys Thr Glu Asn Asp Ile
1               5                   10                  15

Ser His Gln Asn Asn Asp Ile Asn Lys Glu Tyr Glu Glu Val Met Lys
            20                  25                  30

Gln Met Arg Glu Met Arg Val His Met Thr Ala Leu Phe Asn Ser Ile
        35                  40                  45

His Lys Asp Asn Met Glu Trp Arg Met Ser Glu Ser Ile Arg Arg Glu
 50                  55                  60

Lys Lys Arg Glu Met Lys Ser Asn Ala Thr Gly Asn Glu Val Lys Asn
65                  70                  75                  80

His Thr Asn Asp Val Asn Val Cys Asp Thr Ser Gly Leu Glu Thr Glu
                85                  90                  95

Val Cys Leu

<210> SEQ ID NO 31
<211> LENGTH: 297
<212> TYPE: DNA
<213> ORGANISM: Artificial Sequence
<220> FEATURE:
<223> OTHER INFORMATION: NSP4 Isolate 70

<400> SEQUENCE: 31
atcacctcaa agactgtgat tagtaagttc aagactgaaa atgacattag ccaccagaac      60

```
aacgatatca ataaggaata tgaagaggtg atgaaacaaa tgcgtgaaat gagagttcat    120
atgactgcat tatttaatag tatacataaa gataatatgg agtggagaat gagtgaatca    180
attcgcagag aaaagaaacg tgaaatgaaa tcaaatgcaa ccgggaatga agtcaagaat    240
cacaccaatg atgtaaatgt atgtgatacg tctggattag agacggaggt ttgtcta       297
```

<210> SEQ ID NO 32
<211> LENGTH: 99
<212> TYPE: PRT
<213> ORGANISM: Artificial Sequence
<220> FEATURE:
<223> OTHER INFORMATION: NSP4 Isolate 70

<400> SEQUENCE: 32

```
Ile Thr Ser Lys Thr Val Ile Ser Lys Phe Lys Thr Glu Asn Asp Ile
1               5                   10                  15

Ser His Gln Asn Asn Asp Ile Asn Lys Glu Tyr Glu Glu Val Met Lys
            20                  25                  30

Gln Met Arg Glu Met Arg Val His Met Thr Ala Leu Phe Asn Ser Ile
        35                  40                  45

His Lys Asp Asn Met Glu Trp Arg Met Ser Glu Ser Ile Arg Arg Glu
    50                  55                  60

Lys Lys Arg Glu Met Lys Ser Asn Ala Thr Gly Asn Glu Val Lys Asn
65                  70                  75                  80

His Thr Asn Asp Val Asn Val Cys Asp Thr Ser Gly Leu Glu Thr Glu
                85                  90                  95

Val Cys Leu
```

<210> SEQ ID NO 33
<211> LENGTH: 297
<212> TYPE: DNA
<213> ORGANISM: Artificial Sequence
<220> FEATURE:
<223> OTHER INFORMATION: NSP4 Isolate 71

<400> SEQUENCE: 33

```
atcacctcaa agactgtgat tagtaagttc aagactgaaa atgacattag ccaccagaac     60
aacgatatca ataaggaata tgaagaggtg atgaaacaaa tgcgtgaaat gagagttcat    120
atgactgcat tatttaatag tatacataaa gataatatgg agtggagaat gagtgaatca    180
attcgcagag aaaagaaacg tgaaatgaaa tcaaatgcaa ccgggaatga agtcaagaat    240
cacaccaatg atgtaaatgt atgtgatacg tctggattag agacggaggt ttgtcta       297
```

<210> SEQ ID NO 34
<211> LENGTH: 99
<212> TYPE: PRT
<213> ORGANISM: Artificial Sequence
<220> FEATURE:
<223> OTHER INFORMATION: NSP4 Isolate 71 AA sequence

<400> SEQUENCE: 34

```
Ile Thr Ser Lys Thr Val Ile Ser Lys Phe Lys Thr Glu Asn Asp Ile
1               5                   10                  15

Ser His Gln Asn Asn Asp Ile Asn Lys Glu Tyr Glu Glu Val Met Lys
            20                  25                  30

Gln Met Arg Glu Met Arg Val His Met Thr Ala Leu Phe Asn Ser Ile
        35                  40                  45

His Lys Asp Asn Met Glu Trp Arg Met Ser Glu Ser Ile Arg Arg Glu
```

```
            50                  55                  60
Lys Lys Arg Glu Met Lys Ser Asn Ala Thr Gly Asn Glu Val Lys Asn
 65                  70                  75                  80

His Thr Asn Asp Val Asn Val Cys Asp Thr Ser Gly Leu Glu Thr Glu
                 85                  90                  95

Val Cys Leu

<210> SEQ ID NO 35
<211> LENGTH: 297
<212> TYPE: DNA
<213> ORGANISM: Artificial Sequence
<220> FEATURE:
<223> OTHER INFORMATION: NSP4 Isolate 72

<400> SEQUENCE: 35
atcacctcaa agactgtgat tagtaagttc aagactgaaa atgacattag ccaccagaac    60
aacgatatca ataaggaata tgaagaggtg atgaaacaaa tgcgtgaaat gagagttcat   120
atgactgcat tatttaatag tatacataaa gataatatgg agtggagaat gagtgaatca   180
attcgcagag aaaagaagcg tgaaatgaaa tcaaatgcaa ccgggaatga agtcaagatt   240
cacaccaatg atgtaaatgt atgtgatacg tctggattag agacggaggt ttgtcta      297

<210> SEQ ID NO 36
<211> LENGTH: 99
<212> TYPE: PRT
<213> ORGANISM: Artificial Sequence
<220> FEATURE:
<223> OTHER INFORMATION: NSP4 Isolate 72

<400> SEQUENCE: 36

Ile Thr Ser Lys Thr Val Ile Ser Lys Phe Lys Thr Glu Asn Asp Ile
  1               5                  10                  15

Ser His Gln Asn Asn Asp Ile Asn Lys Glu Tyr Glu Glu Val Met Lys
                 20                  25                  30

Gln Met Arg Glu Met Arg Val His Met Thr Ala Leu Phe Asn Ser Ile
             35                  40                  45

His Lys Asp Asn Met Glu Trp Arg Met Ser Glu Ser Ile Arg Arg Glu
     50                  55                  60

Lys Lys Arg Glu Met Lys Ser Asn Ala Thr Gly Asn Glu Val Lys Ile
 65                  70                  75                  80

His Thr Asn Asp Val Asn Val Cys Asp Thr Ser Gly Leu Glu Thr Glu
                 85                  90                  95

Val Cys Leu

<210> SEQ ID NO 37
<211> LENGTH: 297
<212> TYPE: DNA
<213> ORGANISM: Artificial Sequence
<220> FEATURE:
<223> OTHER INFORMATION: NSP4 Isolate 3882

<400> SEQUENCE: 37
atcacctcaa aaactgtgat tggtaaattc aagactgaaa acaatattag tcatcagaat    60
gacgacattc ataaagaata tgaagaggtg atgaaacaaa tgcgtgacat gagagttcat   120
gtaactgcac tatttaatag tatacataag gataatatgg agtggagaat gagtgaatcg   180
attcgcagag aaaagaagcg tgaaatgaaa acaaatacgg tcgagaatga agttaagaat   240
cacgtagatg atgtaaatat atgtgatacg tctggattag agacggaagt ttgtcta      297
```

<210> SEQ ID NO 38
<211> LENGTH: 99
<212> TYPE: PRT
<213> ORGANISM: Artificial Sequence
<220> FEATURE:
<223> OTHER INFORMATION: NSP4 Isolate 3882

<400> SEQUENCE: 38

```
Ile Thr Ser Lys Thr Val Ile Gly Lys Phe Lys Thr Glu Asn Asn Ile
1               5                   10                  15

Ser His Gln Asn Asp Asp Ile His Lys Glu Tyr Glu Glu Val Met Lys
            20                  25                  30

Gln Met Arg Asp Met Arg Val His Val Thr Ala Leu Phe Asn Ser Ile
        35                  40                  45

His Lys Asp Asn Met Glu Trp Arg Met Ser Glu Ser Ile Arg Arg Glu
    50                  55                  60

Lys Lys Arg Glu Met Lys Thr Asn Thr Val Glu Asn Glu Val Lys Asn
65                  70                  75                  80

His Val Asp Asp Val Asn Ile Cys Asp Thr Ser Gly Leu Glu Thr Glu
                85                  90                  95

Val Cys Leu
```

<210> SEQ ID NO 39
<211> LENGTH: 297
<212> TYPE: DNA
<213> ORGANISM: Artificial Sequence
<220> FEATURE:
<223> OTHER INFORMATION: NSP4 Isolate 3509

<400> SEQUENCE: 39

```
atcacctcaa aaactgtgat tggtaaattc aagactgaaa atgacattag ccaccagaac    60
aacgatatca ataaggaata tgaagaggtg atgaaacaaa tgcgtgaaat gagagttcat   120
atgactgcat tatttaatag atacataaaa gataatatgg agtggagaat gagtgaatca   180
attcgcagag aaaagaagcg tgaaatgaaa tcaaatgcaa ccgggaatga agtcaagatt   240
cacaccaatg atgtaaatgt atgtgatacg tctggattag agacggaagt ttgtcta      297
```

<210> SEQ ID NO 40
<211> LENGTH: 99
<212> TYPE: PRT
<213> ORGANISM: Artificial Sequence
<220> FEATURE:
<223> OTHER INFORMATION: NSP4 Isolate 3509

<400> SEQUENCE: 40

```
Ile Thr Ser Lys Thr Val Ile Gly Lys Phe Lys Thr Glu Asn Asp Ile
1               5                   10                  15

Ser His Gln Asn Asn Asp Ile Asn Lys Glu Tyr Glu Glu Val Met Lys
            20                  25                  30

Gln Met Arg Glu Met Arg Val His Met Thr Ala Leu Phe Asn Ser Ile
        35                  40                  45

His Lys Asp Asn Met Glu Trp Arg Met Ser Glu Ser Ile Arg Arg Glu
    50                  55                  60

Lys Lys Arg Glu Met Lys Ser Asn Ala Thr Gly Asn Glu Val Lys Ile
65                  70                  75                  80

His Thr Asn Asp Val Asn Val Cys Asp Thr Ser Gly Leu Glu Thr Glu
                85                  90                  95
```

Val Cys Leu

<210> SEQ ID NO 41
<211> LENGTH: 732
<212> TYPE: DNA
<213> ORGANISM: Artificial Sequence
<220> FEATURE:
<223> OTHER INFORMATION: VP4 Isolate 1

<400> SEQUENCE: 41

```
agggcgtcct cactttatca tcaattaatt tctcagaatt attattcaac tgggaatgag      60
atcttaaaag atttacaaac gactaaaact actgttgact atgtagatgc tgggaattat     120
acatatgctc aattgccgcc aacgaagtgg ggagctggag ctaccttcga atcagtcttt     180
agcgcagctg aaataacagg accgcacaca aatagagtta tagagtggaa gaatttacta     240
aattctgacc agtggttgct gtttccaaaa ccagctgaca cagttaaatt acttaaacat     300
ggacctcaaa catatgatag cactttagcg gcatgtgaat tgtggtatgg gaaggctaat     360
actatagtga catcagaaca ctattcatca ttaagtgata atcaggtgaa tgtaaatgcc     420
gattcattag tattattttg gaatgctgga gggacaacat tcgataaaca aatagttaat     480
tttgcttggg atatgggtgg aattctgatt aagccgtcaa gtcaacaacc tagattagat     540
atatacatgg ccaacatgaa taatttcaat agtgataatt tcaattggga agagtggcgt     600
ttcacactac ctcgcagtaa tgcaacaatt aacatataca ctgattatta cctagctagc     660
agtgatccat acaatcagct gaaagaatta caacagtcaa ctattaccac attcgaaatg     720
agaatgatgg tg                                                          732
```

<210> SEQ ID NO 42
<211> LENGTH: 244
<212> TYPE: PRT
<213> ORGANISM: Artificial Sequence
<220> FEATURE:
<223> OTHER INFORMATION: VP4 Isolate 1

<400> SEQUENCE: 42

```
Arg Ala Ser Ser Leu Tyr His Gln Leu Ile Ser Gln Asn Tyr Tyr Ser
1               5                   10                  15
Thr Gly Asn Glu Ile Leu Lys Asp Leu Gln Thr Thr Lys Thr Thr Val
            20                  25                  30
Asp Tyr Val Asp Ala Gly Asn Tyr Thr Tyr Ala Gln Leu Pro Pro Thr
        35                  40                  45
Lys Trp Gly Ala Gly Ala Thr Phe Glu Ser Val Phe Ser Ala Ala Glu
    50                  55                  60
Ile Thr Gly Pro His Thr Asn Arg Val Ile Glu Trp Lys Asn Leu Leu
65                  70                  75                  80
Asn Ser Asp Gln Trp Leu Leu Phe Pro Lys Pro Ala Asp Thr Val Lys
                85                  90                  95
Leu Leu Lys His Gly Pro Gln Thr Tyr Asp Ser Thr Leu Ala Ala Cys
            100                 105                 110
Glu Leu Trp Tyr Gly Lys Ala Asn Thr Ile Val Thr Ser Glu His Tyr
        115                 120                 125
Ser Ser Leu Ser Asp Asn Gln Val Asn Val Asn Ala Asp Ser Leu Val
    130                 135                 140
Leu Phe Trp Asn Ala Gly Gly Thr Thr Phe Asp Lys Gln Ile Val Asn
145                 150                 155                 160
Phe Ala Trp Asp Met Gly Gly Ile Leu Ile Lys Pro Ser Ser Gln Gln
```

165                 170                 175
Pro Arg Leu Asp Ile Tyr Met Ala Asn Met Asn Asn Phe Asn Ser Asp
                180                 185                 190

Asn Phe Asn Trp Glu Glu Trp Arg Phe Thr Leu Pro Arg Ser Asn Ala
            195                 200                 205

Thr Ile Asn Ile Tyr Thr Asp Tyr Tyr Leu Ala Ser Ser Asp Pro Tyr
        210                 215                 220

Asn Gln Leu Lys Glu Leu Gln Gln Ser Thr Ile Thr Thr Phe Glu Met
225                 230                 235                 240

Arg Met Met Val

<210> SEQ ID NO 43
<211> LENGTH: 735
<212> TYPE: DNA
<213> ORGANISM: Artificial Sequence
<220> FEATURE:
<223> OTHER INFORMATION: VP4 Isolate 66

<400> SEQUENCE: 43
agggcgtcct cactttatca gcaattaatt tcacagaatt attattcaac tggaaatgat      60
attttactgg atcagcaaac aaataacaca actgttgact atatagatat aggaaattat     120
tcgtatacac aattaccgcc gacatcatgg ggagcaggaa tgacttttaa gtctgcattt     180
aatgcagagg aaattacagg acccaataca ggtgatatag atttgaataa tttgacaaat     240
gcgaatgggt ggatattgta tgacaaacca actgatacaa acgattgtt aaaactagga      300
ccagaaagtt atgacagtgt gtacgcagca ttcgaattat ggtatggtaa agcaaatact     360
gtagtcacat caatatacta ttcatcagtg caaaactctg aaaacactgt aacagtacaa     420
catgactcat tagtgttatt cttttaatgtt ggttatactg gtctaactaa gcaaatagtt    480
aaatttaact ggaatatggg aggcatatta gttagaccga ctgctgatgg tagagtggat    540
atttgtatgg ctgacatgaa tgattttaat agtgataatt ttaattggga atcttggaaa     600
cgtagttttc cacgtagcaa cattaacatg tacactgaat attatttagc gaatgttgat    660
ccatataatc aactaaaaat attaaaccaa ctaactgcaa aaaatgtaga aattagaatg    720
atgaaggcaa ttaag                                                   735

<210> SEQ ID NO 44
<211> LENGTH: 245
<212> TYPE: PRT
<213> ORGANISM: Artificial Sequence
<220> FEATURE:
<223> OTHER INFORMATION: VP4 Isolate 66

<400> SEQUENCE: 44

Arg Ala Ser Ser Leu Tyr Gln Gln Leu Ile Ser Gln Asn Tyr Tyr Ser
1               5                   10                  15

Thr Gly Asn Asp Ile Leu Leu Asp Gln Gln Thr Asn Asn Thr Thr Val
            20                  25                  30

Asp Tyr Ile Asp Ile Gly Asn Tyr Ser Tyr Thr Gln Leu Pro Pro Thr
        35                  40                  45

Ser Trp Gly Ala Gly Met Thr Phe Lys Ser Ala Phe Asn Ala Glu Glu
    50                  55                  60

Ile Thr Gly Pro Asn Thr Gly Asp Ile Asp Leu Asn Asn Leu Thr Asn
65                  70                  75                  80

Ala Asn Gly Trp Ile Leu Tyr Asp Lys Pro Thr Asp Thr Lys Arg Leu
                85                  90                  95

```
Leu Lys Leu Gly Pro Glu Ser Tyr Asp Ser Val Tyr Ala Ala Phe Glu
            100                 105                 110
Leu Trp Tyr Gly Lys Ala Asn Thr Val Val Thr Ser Ile Tyr Tyr Ser
            115                 120                 125
Ser Val Gln Asn Ser Glu Asn Thr Val Thr Val Gln His Asp Ser Leu
        130                 135                 140
Val Leu Phe Phe Asn Val Gly Tyr Thr Gly Leu Thr Lys Gln Ile Val
145                 150                 155                 160
Lys Phe Asn Trp Asn Met Gly Gly Ile Leu Val Arg Pro Thr Ala Asp
                165                 170                 175
Gly Arg Val Asp Ile Cys Met Ala Asp Met Asn Asp Phe Asn Ser Asp
            180                 185                 190
Asn Phe Asn Trp Glu Ser Trp Lys Arg Ser Phe Pro Arg Ser Asn Ile
        195                 200                 205
Asn Met Tyr Thr Glu Tyr Tyr Leu Ala Asn Val Asp Pro Tyr Asn Gln
    210                 215                 220
Leu Lys Ile Leu Asn Gln Leu Thr Ala Lys Asn Val Glu Ile Arg Met
225                 230                 235                 240
Met Lys Ala Ile Lys
            245

<210> SEQ ID NO 45
<211> LENGTH: 735
<212> TYPE: DNA
<213> ORGANISM: Artificial Sequence
<220> FEATURE:
<223> OTHER INFORMATION: VP4 Isolate 71

<400> SEQUENCE: 45
agggcgtcct cactttatca gcaattaatc tcacagaatt attattcaac tggaaatgat      60
attttactgg atcagcaaac aaataacaca actgttgact atatagatat aggaaattac     120
tcgtatacac aattaccgcc gacatcatgg ggagcaggaa tgacttttaa gtctgcattt     180
aatgcagagg aaattacagg acccaatacg ggtgatatag atttgaataa tttgacaaat     240
gcgaatggat ggatattgta tgacaaacca actgataaa acgattgtt aaaactagga      300 ccagaaagtt atgacagtgt gtacgcagca ttcgaattat ggtatggtaa agcaaatact     360
gtagtcacat caatatacta ttcatcagtg caaaactctg aaaacactgt aacagtacag     420
catgactcat tagtgttatt ctttaatgtt ggttatactg gtctaactaa gcaaatagtt     480
aaatttaatt ggaatatggg aggcatatta gttagaccga ctactgatgg tagagtggat     540
atttgtatgg ctgacatgaa tgatttagt agtgataatt ttaattggga atcttggaaa     600
cgtagttttc cacgtagcaa cattaacatg tacactgaat attatttagc gaatgttgat     660
ccatataatc aactaaaaat attaaaccaa ctaactgcaa aaaatgtaga aattagaatg     720
atgaaggcaa ttaag                                                      735

<210> SEQ ID NO 46
<211> LENGTH: 245
<212> TYPE: PRT
<213> ORGANISM: Artificial Sequence
<220> FEATURE:
<223> OTHER INFORMATION: VP4 Isolate 71

<400> SEQUENCE: 46

Arg Ala Ser Ser Leu Tyr Gln Gln Leu Ile Ser Gln Asn Tyr Tyr Ser
1               5                   10                  15
```

Thr Gly Asn Asp Ile Leu Leu Asp Gln Gln Thr Asn Thr Thr Val
            20                  25                  30

Asp Tyr Ile Asp Ile Gly Asn Tyr Ser Tyr Thr Gln Leu Pro Pro Thr
        35                  40                  45

Ser Trp Gly Ala Gly Met Thr Phe Lys Ser Ala Phe Asn Ala Glu Glu
 50                  55                  60

Ile Thr Gly Pro Asn Thr Gly Asp Ile Asp Leu Asn Asn Leu Thr Asn
 65                  70                  75                  80

Ala Asn Gly Trp Ile Leu Tyr Asp Lys Pro Thr Asp Thr Lys Arg Leu
                85                  90                  95

Leu Lys Leu Gly Pro Glu Ser Tyr Asp Ser Val Tyr Ala Ala Phe Glu
            100                 105                 110

Leu Trp Tyr Gly Lys Ala Asn Thr Val Val Thr Ser Ile Tyr Tyr Ser
        115                 120                 125

Ser Val Gln Asn Ser Glu Asn Thr Val Thr Val Gln His Asp Ser Leu
130                 135                 140

Val Leu Phe Phe Asn Val Gly Tyr Thr Gly Leu Thr Lys Gln Ile Val
145                 150                 155                 160

Lys Phe Asn Trp Asn Met Gly Gly Ile Leu Val Arg Pro Thr Thr Asp
                165                 170                 175

Gly Arg Val Asp Ile Cys Met Ala Asp Met Asn Asp Phe Ser Ser Asp
            180                 185                 190

Asn Phe Asn Trp Glu Ser Trp Lys Arg Ser Phe Pro Arg Ser Asn Ile
        195                 200                 205

Asn Met Tyr Thr Glu Tyr Tyr Leu Ala Asn Val Asp Pro Tyr Asn Gln
            210                 215                 220

Leu Lys Ile Leu Asn Gln Leu Thr Ala Lys Asn Val Glu Ile Arg Met
225                 230                 235                 240

Met Lys Ala Ile Lys
                245

<210> SEQ ID NO 47
<211> LENGTH: 735
<212> TYPE: DNA
<213> ORGANISM: Artificial Sequence
<220> FEATURE:
<223> OTHER INFORMATION: VP4 Isolate 3509

<400> SEQUENCE: 47
agggcgtcct cactttatca gcaattaatc tcacagaatt attattcaac tggaaatgat    60
attttactgg atcagcaaac aaataacaca actgttgact atatagatat aggaaattat   120
tcgtatacac aattaccgcc gacatcatgg ggagcaggaa tgactttttac gtctgcattt   180 aatgcagagg aaattacagg acccaataca ggtgatatag atttgaataa tttgacaaat   240
gcgaatgggt ggatattgta tgacaaacca actgatacaa aacgattgtt aaaactagga   300
ccagaaagtt atgacagtgt atacgcagca ttcgaattat ggtatggtaa agcaaatact   360
gtagtcacat caatatacta ttcatcagtg caaaactctg aaaacactgt aacagtacag   420
catgactcat tagtgttatt ctttaatgtt ggttatactg gtctaactaa gcaaatagtt   480
aaatttaact ggaatatggg aggcatatta gttagaccga ctactgatgg tagagtggat   540
atttgcatgg ctgacatgaa tgatttttaat agtgataatt ttaattggga atcttggaaa   600
cgtagttttc cacgtagcaa cattaacatg tacactgaat attatttagc gaatgttgat   660
ccatataatc aactaaaaat attaaaccaa ctaactgcaa aaaatgtaga aattagaatg   720
atgaaggcaa ttaag                                                         735

<210> SEQ ID NO 48
<211> LENGTH: 245
<212> TYPE: PRT
<213> ORGANISM: Artificial Sequence
<220> FEATURE:
<223> OTHER INFORMATION: VP4 Isolate 3509

<400> SEQUENCE: 48

Arg Ala Ser Ser Leu Tyr Gln Gln Leu Ile Ser Gln Asn Tyr Tyr Ser
1               5                   10                  15

Thr Gly Asn Asp Ile Leu Leu Asp Gln Gln Thr Asn Asn Thr Thr Val
            20                  25                  30

Asp Tyr Ile Asp Ile Gly Asn Tyr Ser Tyr Thr Gln Leu Pro Pro Thr
        35                  40                  45

Ser Trp Gly Ala Gly Met Thr Phe Thr Ser Ala Phe Asn Ala Glu Glu
    50                  55                  60

Ile Thr Gly Pro Asn Thr Gly Asp Ile Asp Leu Asn Asn Leu Thr Asn
65                  70                  75                  80

Ala Asn Gly Trp Ile Leu Tyr Asp Lys Pro Thr Asp Thr Lys Arg Leu
                85                  90                  95

Leu Lys Leu Gly Pro Glu Ser Tyr Asp Ser Val Tyr Ala Ala Phe Glu
            100                 105                 110

Leu Trp Tyr Gly Lys Ala Asn Thr Val Val Thr Ser Ile Tyr Tyr Ser
        115                 120                 125

Ser Val Gln Asn Ser Glu Asn Thr Val Thr Val Gln His Asp Ser Leu
    130                 135                 140

Val Leu Phe Phe Asn Val Gly Tyr Thr Gly Leu Thr Lys Gln Ile Val
145                 150                 155                 160

Lys Phe Asn Trp Asn Met Gly Gly Ile Leu Val Arg Pro Thr Thr Asp
                165                 170                 175

Gly Arg Val Asp Ile Cys Met Ala Asp Met Asn Asp Phe Asn Ser Asp
            180                 185                 190

Asn Phe Asn Trp Glu Ser Trp Lys Arg Ser Phe Pro Arg Ser Asn Ile
        195                 200                 205

Asn Met Tyr Thr Glu Tyr Tyr Leu Ala Asn Val Asp Pro Tyr Asn Gln
    210                 215                 220

Leu Lys Ile Leu Asn Gln Leu Thr Ala Lys Asn Val Glu Ile Arg Met
225                 230                 235                 240

Met Lys Ala Ile Lys
                245

<210> SEQ ID NO 49
<211> LENGTH: 735
<212> TYPE: DNA
<213> ORGANISM: Artificial Sequence
<220> FEATURE:
<223> OTHER INFORMATION: VP4 Isolate 3882
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (690)..(690)
<223> OTHER INFORMATION: n is a, c, g, or t
<220> FEATURE:
<221> NAME/KEY: misc_feature
<222> LOCATION: (699)..(700)

<223> OTHER INFORMATION: n is a, c, g, or t

<400> SEQUENCE: 49

```
agggcgtcct cactttatca gcaattaatc tcacaaaatt attattcaac tgggaatgnt      60
atattattgg atcagcaaac gaataaaaca actgttgatt atgtagatgt gggaaattat     120
tcatatacac aattaccacc aacatcatgg ggagcaggaa tgactttaa gtctgcattt      180
aatgcagaag aaatgacggg acctaacaca ggtgatatag atctgagtaa tctcacaact    240
gcgaatggat ggatattata tgagaagccg acaattacca aacggttatt aaaactaggg    300
ccagatgttt acgatagtgt ttatgccgca tttgaactgt ggtatggtaa agcaaataca    360
gtagttacat caatatatta tgcatcagca caaaattctg agaatactgt aacattacag    420
tatgactcat tagtactatt tttcaatgtt ggttacactg gtctgactaa gcaaatagtt    480
agatttaatt gggatatggg aggcatatta gttaggccaa ctgctgatgg tagagtagat    540
atctgtatgg cagacatgaa tgattttagc agcgacaatt ttaattggga gaaatggact    600
cgtagctttc cacgcagtaa tattaatatg tatgctgaat attacttagc aaatgttgac    660
ccgtatagtc aattaaaagc attaaatcan ctcacaacnn aaaatataga aattagaatg    720
atgaagtcaa ttaag                                                     735
```

<210> SEQ ID NO 50
<211> LENGTH: 245
<212> TYPE: PRT
<213> ORGANISM: Artificial Sequence
<220> FEATURE:
<223> OTHER INFORMATION: VP4 Isolate 3882
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (230)..(230)
<223> OTHER INFORMATION: Xaa can be any naturally occurring amino acid
<220> FEATURE:
<221> NAME/KEY: misc_feature
<222> LOCATION: (233)..(234)
<223> OTHER INFORMATION: Xaa can be any naturally occurring amino acid
<220> FEATURE:
<221> NAME/KEY: misc_feature
<222> LOCATION: (245)..(245)
<223> OTHER INFORMATION: Xaa can be any naturally occurring amino acid

<400> SEQUENCE: 50

```
Arg Ala Ser Ser Leu Tyr Gln Gln Leu Ile Ser Gln Asn Tyr Tyr Ser
1               5                   10                  15

Thr Gly Asn Xaa Ile Leu Leu Asp Gln Gln Thr Asn Lys Thr Thr Val
            20                  25                  30

Asp Tyr Val Asp Val Gly Asn Tyr Ser Tyr Thr Gln Leu Pro Pro Thr
        35                  40                  45

Ser Trp Gly Ala Gly Met Thr Phe Lys Ser Ala Phe Asn Ala Glu Glu
    50                  55                  60

Met Thr Gly Pro Asn Thr Gly Asp Ile Asp Leu Ser Asn Leu Thr Thr
65                  70                  75                  80

Ala Asn Gly Trp Ile Leu Tyr Glu Lys Pro Thr Ile Thr Lys Arg Leu
                85                  90                  95

Leu Lys Leu Gly Pro Asp Val Tyr Asp Ser Val Tyr Ala Ala Phe Glu
            100                 105                 110

Leu Trp Tyr Gly Lys Ala Asn Thr Val Val Thr Ser Ile Tyr Tyr Ala
        115                 120                 125
```

Ser Ala Gln Asn Ser Glu Asn Thr Val Thr Leu Gln Tyr Asp Ser Leu
    130                 135                 140

Val Leu Phe Phe Asn Val Gly Tyr Thr Gly Leu Thr Lys Gln Ile Val
145                 150                 155                 160

Arg Phe Asn Trp Asp Met Gly Gly Ile Leu Val Arg Pro Thr Ala Asp
                165                 170                 175

Gly Arg Val Asp Ile Cys Met Ala Asp Met Asn Asp Phe Ser Ser Asp
            180                 185                 190

Asn Phe Asn Trp Glu Lys Trp Thr Arg Ser Phe Pro Arg Ser Asn Ile
        195                 200                 205

Asn Met Tyr Ala Glu Tyr Tyr Leu Ala Asn Val Asp Pro Tyr Ser Gln
    210                 215                 220

Leu Lys Ala Leu Asn Xaa Leu Thr Xaa Xaa Asn Ile Glu Ile Arg Met
225                 230                 235                 240

Met Lys Ser Ile Xaa
            245

<210> SEQ ID NO 51
<211> LENGTH: 1182
<212> TYPE: DNA
<213> ORGANISM: Artificial Sequence
<220> FEATURE:
<223> OTHER INFORMATION: VP6 Isolate 1

<400> SEQUENCE: 51
gacgtgctgt ttcaattgc gaaaactgta tctgaactca aaagaaagt tgtagttggt        60
actatttaca ctaatgtaga agatataatt caacaaacca atgaactgat agaactttg     120
aatggtaata cgtttcatac aggtggtatt ggaacacagc ctcaggaaga gtggaatttt    180
caattaccgc agctaggtac gacactctta aatttagatg acaactatgt tcaagccact    240
agaagtgtta ttgattattt ggcttcattt atagaatcag tatgtgatga tgaaattgtc    300
agagaagcat ctagaaatgg aatgcagcca cagtcgccag cacttataac gctgtcatca    360
tcaaagttta agactatcaa ctttaataac agttcacaat caattaaaaa ttggagtgct    420
caatcaagac gtgaaaatcc agtctatgaa tacagaaatc caatgatatt cgaatataga    480
aattcataca ttcttcagcg tgctaatcca caatttggaa tcgtaatggg attgaggtat    540
tatacaactg gtaacacctg tcaagttgca gcttttgatt caacatttgc tgaaaatgct    600
cctaataata ctcaacgttt tatctataat ggaagactta agagaccaac ttctaatgca    660
ttgatgaaaa ttgaggctgg cgctcagaac atcagtattc aacagttttt gcctgatctg    720
gcaaatcaaa caacatggtt atttaatcca gtgcaagtaa tgaatggaac attctctatt    780
gaattttata caatggaca actagttgat atgattagaa tatgggagt agttactgtt    840
agaactttg attcttacag aataacaatc gatgtgatta ccagcagc tatgacacaa       900
tacgttcaga gaacattccc gcaaggtggt cctatccat accaagctgc atacatgttg     960
acgctcagtg tattagatgc gacaacggaa tctgtcctat gcgattcaca ctctgtggat   1020
tattcaattg ttgcaaacgt tagaagagac tcagcaatgc cagctggaac agtatttcaa   1080
ccagggtttc catgggaaca gacattatcc aactacactg ttgctcagga agataattta   1140
gaaagacttt tactagttgc gtccgtgaag agaatggtga tg                      1182

<210> SEQ ID NO 52
<211> LENGTH: 394
<212> TYPE: PRT

<213> ORGANISM: Artificial Sequence
<220> FEATURE:
<223> OTHER INFORMATION: VP6 Isolate 1

<400> SEQUENCE: 52

```
Asp Val Leu Phe Ser Ile Ala Lys Thr Val Ser Glu Leu Lys Lys Lys
1               5                   10                  15

Val Val Val Gly Thr Ile Tyr Thr Asn Val Glu Asp Ile Ile Gln Gln
            20                  25                  30

Thr Asn Glu Leu Ile Arg Thr Leu Asn Gly Asn Thr Phe His Thr Gly
        35                  40                  45

Gly Ile Gly Thr Gln Pro Gln Glu Glu Trp Asn Phe Gln Leu Pro Gln
    50                  55                  60

Leu Gly Thr Thr Leu Leu Asn Leu Asp Asp Asn Tyr Val Gln Ala Thr
65                  70                  75                  80

Arg Ser Val Ile Asp Tyr Leu Ala Ser Phe Ile Glu Ser Val Cys Asp
                85                  90                  95

Asp Glu Ile Val Arg Glu Ala Ser Arg Asn Gly Met Gln Pro Gln Ser
            100                 105                 110

Pro Ala Leu Ile Thr Leu Ser Ser Ser Lys Phe Lys Thr Ile Asn Phe
        115                 120                 125

Asn Asn Ser Ser Gln Ser Ile Lys Asn Trp Ser Ala Gln Ser Arg Arg
    130                 135                 140

Glu Asn Pro Val Tyr Glu Tyr Arg Asn Pro Met Ile Phe Glu Tyr Arg
145                 150                 155                 160

Asn Ser Tyr Ile Leu Gln Arg Ala Asn Pro Gln Phe Gly Ile Val Met
                165                 170                 175

Gly Leu Arg Tyr Tyr Thr Thr Gly Asn Thr Cys Gln Val Ala Ala Phe
            180                 185                 190

Asp Ser Thr Phe Ala Glu Asn Ala Pro Asn Asn Thr Gln Arg Phe Ile
        195                 200                 205

Tyr Asn Gly Arg Leu Lys Arg Pro Thr Ser Asn Ala Leu Met Lys Ile
    210                 215                 220

Glu Ala Gly Ala Gln Asn Ile Ser Ile Pro Thr Val Leu Pro Asp Leu
225                 230                 235                 240

Ala Asn Gln Thr Thr Trp Leu Phe Asn Pro Val Gln Val Met Asn Gly
                245                 250                 255

Thr Phe Ser Ile Glu Phe Tyr Asn Asn Gly Gln Leu Val Asp Met Ile
            260                 265                 270

Arg Asn Met Gly Val Val Thr Val Arg Thr Phe Asp Ser Tyr Arg Ile
        275                 280                 285

Thr Ile Asp Val Ile Arg Pro Ala Ala Met Thr Gln Tyr Val Gln Arg
    290                 295                 300

Thr Phe Pro Gln Gly Gly Pro Tyr Pro Tyr Gln Ala Ala Tyr Met Leu
305                 310                 315                 320

Thr Leu Ser Val Leu Asp Ala Thr Thr Glu Ser Val Leu Cys Asp Ser
                325                 330                 335

His Ser Val Asp Tyr Ser Ile Val Ala Asn Val Arg Arg Asp Ser Ala
            340                 345                 350

Met Pro Ala Gly Thr Val Phe Gln Pro Gly Phe Pro Trp Glu Gln Thr
        355                 360                 365

Leu Ser Asn Tyr Thr Val Ala Gln Glu Asp Asn Leu Glu Arg Leu Leu
    370                 375                 380

Leu Val Ala Ser Val Lys Arg Met Val Met
```

<210> SEQ ID NO 53
<211> LENGTH: 1182
<212> TYPE: DNA
<213> ORGANISM: Artificial Sequence
<220> FEATURE:
<223> OTHER INFORMATION: VP6 Isolate 63

<400> SEQUENCE: 53

```
gatgtgctgt tctccattgc gaagactgtc tcagatctta agaagaaagt tgtagttggt      60
actatttata caaatgtaga agatataatc caacagacta atgaattgat tagaactttg     120
aatggcaaca cattccatac tggtggaatt ggaacacaac ctcagaaaga atggaatttt     180
caactaccac agctaggtac aacactttg aatttagatg ataactatgt tcaagcaact     240
agaagtatca tcgattattt ggcctcattt atagaagctg tgtgtgatga cgaaattgtt     300
agagaagcgt caagaaatgg aatgcaacct caatctcctg cacttatagc gttatcttca     360
gcaaaattta agactattaa tttaacaat agttcacaat ccattaagaa ttggagtgct     420
cagtcaagac gtgaaaatcc agtgtatgaa tataaaaatc caatggtgtt tgagtataga     480
aattcatata ttcttcagcg tgccaatgca caatatggga acgtaatggg gctgagatat     540
tacacagcca gcaatgcctg tcagattgca gcttttgatt caactttagc tgaaaatgct     600
cctaatggca ctcaacggtt tatttataat ggaagactta aaagaccaat ttctaatgtg     660
ttgatgaaaa ttgaggcggg tgctccaaac attagtaatc caacaatact acctgatcca     720
gcaaatcaga acatggct atttaatcca gtgcagataa tgaatggaac atttactatt     780
gagttttata ataatgggca gttagttgat ttgattagaa atatgggagt agttactgtt     840
agaacatttg atacgtacag aattacaatt gacatgatta gaccagcaac catgacacag     900
tatgtacaaa gactgttcc acagggtggc ccatatcaac atcaagccgc atatatgata     960
actcttagta tattggatgc cacaacagaa tcagtcatgt gtgattcaca ttcagtagat    1020
tattcaatcg tcgcaaatgt cagaagagac tcagcaatgc cagctggaac agtatttcaa    1080
ccaggatttc catgggaaca gatattatcc aactacactg ttgctcagga ggataattta    1140
gaaagacttt tgttagttgc gtctgtgaag agaatggtga tg                       1182
```

<210> SEQ ID NO 54
<211> LENGTH: 394
<212> TYPE: PRT
<213> ORGANISM: Artificial Sequence
<220> FEATURE:
<223> OTHER INFORMATION: VP6 Isolate 63

<400> SEQUENCE: 54

```
Asp Val Leu Phe Ser Ile Ala Lys Thr Val Ser Asp Leu Lys Lys Lys
1               5                   10                  15

Val Val Val Gly Thr Ile Tyr Thr Asn Val Glu Asp Ile Ile Gln Gln
            20                  25                  30

Thr Asn Glu Leu Ile Arg Thr Leu Asn Gly Asn Thr Phe His Thr Gly
        35                  40                  45

Gly Ile Gly Thr Gln Pro Gln Lys Glu Trp Asn Phe Gln Leu Pro Gln
    50                  55                  60

Leu Gly Thr Thr Leu Leu Asn Leu Asp Asp Asn Tyr Val Gln Ala Thr
65                  70                  75                  80

Arg Ser Ile Ile Asp Tyr Leu Ala Ser Phe Ile Glu Ala Val Cys Asp
                85                  90                  95
```

```
Asp Glu Ile Val Arg Glu Ala Ser Arg Asn Gly Met Gln Pro Gln Ser
                100                 105                 110
Pro Ala Leu Ile Ala Leu Ser Ser Ala Lys Phe Lys Thr Ile Asn Phe
            115                 120                 125
Asn Asn Ser Ser Gln Ser Ile Lys Asn Trp Ser Ala Gln Ser Arg Arg
130                 135                 140
Glu Asn Pro Val Tyr Glu Tyr Lys Asn Pro Met Val Phe Glu Tyr Arg
145                 150                 155                 160
Asn Ser Tyr Ile Leu Gln Arg Ala Asn Ala Gln Tyr Gly Asn Val Met
                165                 170                 175
Gly Leu Arg Tyr Tyr Thr Ala Ser Asn Ala Cys Gln Ile Ala Ala Phe
            180                 185                 190
Asp Ser Thr Leu Ala Glu Asn Ala Pro Asn Gly Thr Gln Arg Phe Ile
        195                 200                 205
Tyr Asn Gly Arg Leu Lys Arg Pro Ile Ser Asn Val Leu Met Lys Ile
    210                 215                 220
Glu Ala Gly Ala Pro Asn Ile Ser Asn Pro Thr Ile Leu Pro Asp Pro
225                 230                 235                 240
Ala Asn Gln Thr Thr Trp Leu Phe Asn Pro Val Gln Ile Met Asn Gly
                245                 250                 255
Thr Phe Thr Ile Glu Phe Tyr Asn Asn Gly Gln Leu Val Asp Leu Ile
            260                 265                 270
Arg Asn Met Gly Val Val Thr Val Arg Thr Phe Asp Thr Tyr Arg Ile
        275                 280                 285
Thr Ile Asp Met Ile Arg Pro Ala Thr Met Thr Gln Tyr Val Gln Arg
    290                 295                 300
Leu Phe Pro Gln Gly Gly Pro Tyr Gln His Gln Ala Ala Tyr Met Ile
305                 310                 315                 320
Thr Leu Ser Ile Leu Asp Ala Thr Thr Glu Ser Val Met Cys Asp Ser
                325                 330                 335
His Ser Val Asp Tyr Ser Ile Val Ala Asn Val Arg Arg Asp Ser Ala
            340                 345                 350
Met Pro Ala Gly Thr Val Phe Gln Pro Gly Phe Pro Trp Glu Gln Ile
        355                 360                 365
Leu Ser Asn Tyr Thr Val Ala Gln Glu Asp Asn Leu Glu Arg Leu Leu
    370                 375                 380
Leu Val Ala Ser Val Lys Arg Met Val Met
385                 390

<210> SEQ ID NO 55
<211> LENGTH: 1182
<212> TYPE: DNA
<213> ORGANISM: Artificial Sequence
<220> FEATURE:
<223> OTHER INFORMATION: VP6 Isolate 64

<400> SEQUENCE: 55
gatgtgctgt tctccattgc gaagactgtc tcagatctta agaagaaagt tgtagttggt      60
actatttata caaatgtaga agatataatc aacagacta atgaattgat tagaactttg     120
aatggcaaca catttcatac tggtggaatt ggaacacaac ctcagaaaga atggaatttt     180
caactaccac agctaggtac aacactttg aatttagatg ataactatgt tcaagcaact     240
agaagtatca tcgattattt ggcctcattt atagaagctg tgtgtgatga cgaaattgtt     300
agagaagcgt caagaaatgg aatgcaacct caatctcctg cacttatagc gttatcttca     360
```

```
gcaaaattta agactattaa ttttaacaat agttcacaat ccattaagaa ttggagtgct    420
cagtcaagac gtgaaaatcc agtgtatgaa tataaaaatc caatggtgtt tgagtataga    480
aattcatata ttcttcagcg tgctaatgca caatatggga atgtaatggg gctgagatat    540
tacacagcga gtaatgcctg tcagattgca gcttttgatt caactttagc tgaaaatgcc    600
cctaatggta ctcaacggtt tatttataat ggaagactta aagaccaat ttctaatgtg    660 ttgatgaaaa ttgaggcggg tgctccaaac attagtaatc caacaatact acctgatcca    720
gcaaatcaga caacatggct atttaatcca gtacagataa tgaatggaac atttactatt    780
gagttttata ataatgggca gttagttgat ttaattagaa atatgggagt agttactgtt    840
agaacatttg atacgtacag aattacaatt gacatgatta gaccagcagc catgacacag    900
tatgtacaaa gactgtttcc acagggtggc ccatatcaac atcaagccgc atatatgata    960
actcttagta tattggatgc cacaacagaa tcagtcatgt gtgattcaca ttcagtagat   1020
tattcaatcg tcgcaaatgt cagaagagac tcagcaatgc cagctggaac agtatttcaa   1080
ccaggctttc catgggaaca gatattatcc aactacactg ttgctcagga ggataattta   1140
gaaagacttt tgttagttgc gtctgtgaag agaatggtga tg                      1182
```

<210> SEQ ID NO 56  
<211> LENGTH: 394  
<212> TYPE: PRT  
<213> ORGANISM: Artificial Sequence  
<220> FEATURE:  
<223> OTHER INFORMATION: VP6 Isolate 64 AA sequences
<400> SEQUENCE: 56

```
Asp Val Leu Phe Ser Ile Ala Lys Thr Val Ser Asp Leu Lys Lys Lys
1               5                   10                  15

Val Val Val Gly Thr Ile Tyr Thr Asn Val Glu Asp Ile Ile Gln Gln
            20                  25                  30

Thr Asn Glu Leu Ile Arg Thr Leu Asn Gly Asn Thr Phe His Thr Gly
        35                  40                  45

Gly Ile Gly Thr Gln Pro Gln Lys Glu Trp Asn Phe Gln Leu Pro Gln
    50                  55                  60

Leu Gly Thr Thr Leu Leu Asn Leu Asp Asp Asn Tyr Val Gln Ala Thr
65                  70                  75                  80

Arg Ser Ile Ile Asp Tyr Leu Ala Ser Phe Ile Glu Ala Val Cys Asp
                85                  90                  95

Asp Glu Ile Val Arg Glu Ala Ser Arg Asn Gly Met Gln Pro Gln Ser
            100                 105                 110

Pro Ala Leu Ile Ala Leu Ser Ser Ala Lys Phe Lys Thr Ile Asn Phe
        115                 120                 125

Asn Asn Ser Ser Gln Ser Ile Lys Asn Trp Ser Ala Gln Ser Arg Arg
    130                 135                 140

Glu Asn Pro Val Tyr Glu Tyr Lys Asn Pro Met Val Phe Glu Tyr Arg
145                 150                 155                 160

Asn Ser Tyr Ile Leu Gln Arg Ala Asn Ala Gln Tyr Gly Asn Val Met
                165                 170                 175

Gly Leu Arg Tyr Tyr Thr Ala Ser Asn Ala Cys Gln Ile Ala Ala Phe
            180                 185                 190

Asp Ser Thr Leu Ala Glu Asn Ala Pro Asn Gly Thr Gln Arg Phe Ile
        195                 200                 205

Tyr Asn Gly Arg Leu Lys Arg Pro Ile Ser Asn Val Leu Met Lys Ile
```

```
                210                 215                 220
Glu Ala Gly Ala Pro Asn Ile Ser Asn Pro Thr Ile Leu Pro Asp Pro
225                 230                 235                 240

Ala Asn Gln Thr Thr Trp Leu Phe Asn Pro Val Gln Ile Met Asn Gly
                245                 250                 255

Thr Phe Thr Ile Glu Phe Tyr Asn Asn Gly Gln Leu Val Asp Leu Ile
            260                 265                 270

Arg Asn Met Gly Val Val Thr Val Arg Thr Phe Asp Thr Tyr Arg Ile
        275                 280                 285

Thr Ile Asp Met Ile Arg Pro Ala Ala Met Thr Gln Tyr Val Gln Arg
    290                 295                 300

Leu Phe Pro Gln Gly Gly Pro Tyr Gln His Gln Ala Ala Tyr Met Ile
305                 310                 315                 320

Thr Leu Ser Ile Leu Asp Ala Thr Thr Glu Ser Val Met Cys Asp Ser
                325                 330                 335

His Ser Val Asp Tyr Ser Ile Val Ala Asn Val Arg Arg Asp Ser Ala
            340                 345                 350

Met Pro Ala Gly Thr Val Phe Gln Pro Gly Phe Pro Trp Glu Gln Ile
        355                 360                 365

Leu Ser Asn Tyr Thr Val Ala Gln Glu Asp Asn Leu Glu Arg Leu Leu
    370                 375                 380

Leu Val Ala Ser Val Lys Arg Met Val Met
385                 390
```

<210> SEQ ID NO 57
<211> LENGTH: 1182
<212> TYPE: DNA
<213> ORGANISM: Artificial Sequence
<220> FEATURE:
<223> OTHER INFORMATION: VP6 Isolate 65

<400> SEQUENCE: 57

```
gatgtgctgt tttcaattgc gaagactgtc tcagaactca aaaagaaagt tgtagttggt    60
actatttaca ctaatgtaga agatataatt cagcaaacta tgaattaat tagaactttg    120
aatggcaaca cgtttcatac aggtggtatt ggaacgcagc ctcaaaaaga gtggaatttt    180
caattaccac agctaggtac aacactcttg aatttagatg ataactatgt ccaagctact    240
agaagtgtta ttgactattt ggcctcattc atagaagcag tatgtgatga tgagattgtc    300
agagaagcat cgagaaatgg aatgcagcct caatcaccta cactttatagc gctgtcctca    360
tcaaaattta aaactattaa ttttaataac agttcacaat ctattaaaaa ctggagtgct    420
caatcaagac gcgaaaatcc agtctacgag tacagaaatc cgatgatatt cgaatataga    480
aattcataca ttcttcagcg cgctaatcca caatttggaa atgtaatggg ttgaggtat    540
tatacaacta gtaacacttg tcaaatcgca gcttttgact caacatttgc tgagaatgct    600
cctaataata ctcaacgttt catctataat ggaagactta agagaccaat ttctaatgtg    660
ctaatgaaaa ttgaggctgg tgctcagaac atcagtagtc caacagtcct acctgatccg    720
acaaatcaaa caacatggct atttaatcca gtacaagtaa tgaatggaac tttactatt    780
gagttttata ataatggaca attagttgat atgattagaa acatggagt agttactgtt    840
agaacttttg attcttatag aataacaatt gatatgatca gaccagcagc tatgacacaa    900
tacgttcaga gaacattccc caagggtggt cctatccat accaagctgc atacatgttg    960
acactcagtg tattagatgc tacaacagaa tctgtcctat gcgattcaca ctctgtagac   1020
```

```
tattcaattg ttgcaaacat tagaagagac tcagcaatgc cagctggaac agtatttcaa    1080
ccaggatttc catgggaaca gacattatcc aactacactg ttgctcagga ggataattta    1140
gaaagacttc tactagttgc gtccgtgaag agaatggtga tg                        1182
```

<210> SEQ ID NO 58
<211> LENGTH: 394
<212> TYPE: PRT
<213> ORGANISM: Artificial Sequence
<220> FEATURE:
<223> OTHER INFORMATION: VP6 Isolate 65

<400> SEQUENCE: 58

```
Asp Val Leu Phe Ser Ile Ala Lys Thr Val Ser Glu Leu Lys Lys Lys
1               5                   10                  15

Val Val Gly Thr Ile Tyr Thr Asn Val Glu Asp Ile Ile Gln Gln
            20                  25                  30

Thr Asn Glu Leu Ile Arg Thr Leu Asn Gly Asn Thr Phe His Thr Gly
        35                  40                  45

Gly Ile Gly Thr Gln Pro Gln Lys Glu Trp Asn Phe Gln Leu Pro Gln
    50                  55                  60

Leu Gly Thr Thr Leu Leu Asn Leu Asp Asp Asn Tyr Val Gln Ala Thr
65                  70                  75                  80

Arg Ser Val Ile Asp Tyr Leu Ala Ser Phe Ile Glu Ala Val Cys Asp
                85                  90                  95

Asp Glu Ile Val Arg Glu Ala Ser Arg Asn Gly Met Gln Pro Gln Ser
            100                 105                 110

Pro Thr Leu Ile Ala Leu Ser Ser Lys Phe Lys Thr Ile Asn Phe
        115                 120                 125

Asn Asn Ser Ser Gln Ser Ile Lys Asn Trp Ser Ala Gln Ser Arg Arg
130                 135                 140

Glu Asn Pro Val Tyr Glu Tyr Arg Asn Pro Met Ile Phe Glu Tyr Arg
145                 150                 155                 160

Asn Ser Tyr Ile Leu Gln Arg Ala Asn Pro Gln Phe Gly Asn Val Met
                165                 170                 175

Gly Leu Arg Tyr Tyr Thr Thr Ser Asn Thr Cys Gln Ile Ala Ala Phe
            180                 185                 190

Asp Ser Thr Phe Ala Glu Asn Ala Pro Asn Asn Thr Gln Arg Phe Ile
        195                 200                 205

Tyr Asn Gly Arg Leu Lys Arg Pro Ile Ser Asn Val Leu Met Lys Ile
    210                 215                 220

Glu Ala Gly Ala Gln Asn Ile Ser Ser Pro Thr Val Leu Pro Asp Pro
225                 230                 235                 240

Thr Asn Gln Thr Thr Trp Leu Phe Asn Pro Val Gln Val Met Asn Gly
                245                 250                 255

Thr Phe Thr Ile Glu Phe Tyr Asn Asn Gly Gln Leu Val Asp Met Ile
            260                 265                 270

Arg Asn Met Gly Val Val Thr Val Arg Thr Phe Asp Ser Tyr Arg Ile
        275                 280                 285

Thr Ile Asp Met Ile Arg Pro Ala Ala Met Thr Gln Tyr Val Gln Arg
    290                 295                 300

Thr Phe Pro Gln Gly Gly Pro Tyr Pro Tyr Gln Ala Ala Tyr Met Leu
305                 310                 315                 320

Thr Leu Ser Val Leu Asp Ala Thr Thr Glu Ser Val Leu Cys Asp Ser
                325                 330                 335
```

His Ser Val Asp Tyr Ser Ile Val Ala Asn Ile Arg Arg Asp Ser Ala
                340                 345                 350

Met Pro Ala Gly Thr Val Phe Gln Pro Gly Phe Pro Trp Glu Gln Thr
            355                 360                 365

Leu Ser Asn Tyr Thr Val Ala Gln Glu Asp Asn Leu Glu Arg Leu Leu
        370                 375                 380

Leu Val Ala Ser Val Lys Arg Met Val Met
385                 390

<210> SEQ ID NO 59
<211> LENGTH: 1182
<212> TYPE: DNA
<213> ORGANISM: Artificial Sequence
<220> FEATURE:
<223> OTHER INFORMATION: VP6 Isolate 66

<400> SEQUENCE: 59
gatgtgctgt tttcaattgc gaagactgtc tcagatctta agaagaaagt tgtagttggt      60
actatttata caaatgtaga agatataatc aacagacta atgaattgat tagaactttg     120
aatggcaaca catttcatac tggtggaatt ggaacacaac ctcagaaaga atggaatttt     180
caactaccac agctaggtac aacacttttg aatttagatg ataactatgt tcaagcaact     240
agaagtatca tcgattattt ggcctcattt atagaagctg tgtgtgatga cgaaattgtt     300
agagaggcgt caagaaatgg aatgcaacct caatctcctg cacttatagc gttatcttca     360
gcaaaattta agactattaa ttttaacaat agttcacaat ccattaagaa ttggagtgct     420
cagtcaagac gtgaaaatcc agtgtatgaa tataaaaatc caatggtgtt tgagtataga     480
aattcatata ttcttcagcg tgctaatgca caatatggga atgtaatggg gctgagatat     540
tacacagcga gtaatgcctg tcagattgca gcttttgatt caactttagc tgaaaatgcc     600
cctaatggta ctcaacggtt tatttataat ggaagactta aagaccaat tctaatgtg      660
ttgatgaaaa ttgaggcggg tgctccaaac attagtaatc aacaatact acctgatcca     720
gcaaatcaga acaatggct atttaatcca gtacagataa tgaatggaac atttactatt     780
gagtttttata ataatgggca gttagttgat ttaattagaa atatgggagt agttactgtt     840
agaacatttg atacgtacag aattacaatt gacatgatta gaccagcagc catgacacag     900
tatgtacaaa gactgtttcc acagggtggc ccatatcaac atcaagccgc atatatgata     960
actcttagta tattggatgc cacaacagaa tcagtcatgt gtgattcaca ttcagtagat    1020
tattcaatcg tcgcaaatgt cagaagagac tcagcaatgc cagctggaac agtatttcaa    1080
ccaggctttc catgggaaca gatattatcc aactacactg ttgctcagga ggataattta    1140
gaaagacttt tgttagttgc gtctgtgaag agaatggtga tg                        1182

<210> SEQ ID NO 60
<211> LENGTH: 394
<212> TYPE: PRT
<213> ORGANISM: Artificial Sequence
<220> FEATURE:
<223> OTHER INFORMATION: VP6 Isolate 66

<400> SEQUENCE: 60

Asp Val Leu Phe Ser Ile Ala Lys Thr Val Ser Asp Leu Lys Lys Lys
1               5                  10                  15

Val Val Val Gly Thr Ile Tyr Thr Asn Val Glu Asp Ile Ile Gln Gln
            20                  25                  30

Thr Asn Glu Leu Ile Arg Thr Leu Asn Gly Asn Thr Phe His Thr Gly 35                  40                  45
Gly Ile Gly Thr Gln Pro Gln Lys Glu Trp Asn Phe Gln Leu Pro Gln
 50                  55                  60

Leu Gly Thr Thr Leu Leu Asn Leu Asp Asp Asn Tyr Val Gln Ala Thr
 65                  70                  75                  80

Arg Ser Ile Ile Asp Tyr Leu Ala Ser Phe Ile Glu Ala Val Cys Asp
                 85                  90                  95

Asp Glu Ile Val Arg Glu Ala Ser Arg Asn Gly Met Gln Pro Gln Ser
            100                 105                 110

Pro Ala Leu Ile Ala Leu Ser Ser Ala Lys Phe Lys Thr Ile Asn Phe
        115                 120                 125

Asn Asn Ser Ser Gln Ser Ile Lys Asn Trp Ser Ala Gln Ser Arg Arg
130                 135                 140

Glu Asn Pro Val Tyr Glu Tyr Lys Asn Pro Met Val Phe Glu Tyr Arg
145                 150                 155                 160

Asn Ser Tyr Ile Leu Gln Arg Ala Asn Ala Gln Tyr Gly Asn Val Met
                165                 170                 175

Gly Leu Arg Tyr Tyr Thr Ala Ser Asn Ala Cys Gln Ile Ala Ala Phe
            180                 185                 190

Asp Ser Thr Leu Ala Glu Asn Ala Pro Asn Gly Thr Gln Arg Phe Ile
        195                 200                 205

Tyr Asn Gly Arg Leu Lys Arg Pro Ile Ser Asn Val Leu Met Lys Ile
210                 215                 220

Glu Ala Gly Ala Pro Asn Ile Ser Asn Pro Thr Ile Leu Pro Asp Pro
225                 230                 235                 240

Ala Asn Gln Thr Thr Trp Leu Phe Asn Pro Val Gln Ile Met Asn Gly
                245                 250                 255

Thr Phe Thr Ile Glu Phe Tyr Asn Asn Gly Gln Leu Val Asp Leu Ile
            260                 265                 270

Arg Asn Met Gly Val Val Thr Val Arg Thr Phe Asp Thr Tyr Arg Ile
        275                 280                 285

Thr Ile Asp Met Ile Arg Pro Ala Ala Met Thr Gln Tyr Val Gln Arg
290                 295                 300

Leu Phe Pro Gln Gly Gly Pro Tyr Gln His Gln Ala Ala Tyr Met Ile
305                 310                 315                 320

Thr Leu Ser Ile Leu Asp Ala Thr Thr Glu Ser Val Met Cys Asp Ser
                325                 330                 335

His Ser Val Asp Tyr Ser Ile Val Ala Asn Val Arg Arg Asp Ser Ala
            340                 345                 350

Met Pro Ala Gly Thr Val Phe Gln Pro Gly Phe Pro Trp Glu Gln Ile
        355                 360                 365

Leu Ser Asn Tyr Thr Val Ala Gln Glu Asp Asn Leu Glu Arg Leu Leu
370                 375                 380

Leu Val Ala Ser Val Lys Arg Met Val Met
385                 390

<210> SEQ ID NO 61
<211> LENGTH: 1182
<212> TYPE: DNA
<213> ORGANISM: Artificial Sequence
<220> FEATURE:
<223> OTHER INFORMATION: VP6 Isolate 67

<400> SEQUENCE: 61
gatgtgctgt tctctattgc gaagactgtc tcagatctta agaagaaagt tgtagttggt      60

```
actatttata caaatgtaga agatataatc caacaaacta atgaattgat tagaactttg      120
aatggcaaca cattccatac tggtggaatt ggaacacaac ctcagaaaga atggaatttt      180
caactaccgc agctaggtac aacacttttg aatttagatg ataactatgt tcaagcaact      240
agaagtatca tcgattattt gacctcattt atagaagctg tgtgtgatga cgaaattgtt      300
agagaagcgt caagaaatgg aatgcaacct caatctcctg cacttatagc gttatcttca      360
gcaaaattta agactattaa tttaacaat agttcacaat ccattaagaa ttggagtgct       420
cagtcaagac gtgaaaatcc agtgtatgaa tataaaaatc caatggtgtt tgagtataga      480
aattcatata ttcttcagcg tgccaatgca caatatggga acgtgatggg gctgagatat      540
tacacagcta gcaatgcctg tcagattgca gcttttgatt caactttagc tgaaaatgcc      600
cctaatggta ctcaacggtt tatttataat gggagactta aaagaccaat ttctaatgtg      660
ttgatgaaaa ttgaggcggg tgctccaaac attagtactc caacaatact acctgatcca      720
gcaaatcaga caacatggct atttaatcca gtacagataa tgaatggaac atttactatt      780
gagttttata ataatgggca gttagttgat ttaattagaa atatgggagt agttactgtt      840
agaacattcg atacgtacag aattacaatt gacatgatta gaccagcagc catgacacag      900
tatgtacaaa gactgtttcc acagggtggc ccatatcaac atcaagccgc atatatgata      960
actcttagta tattggatgc cacaacagaa tcagtcatgt gtgattcaca ttcagtagat     1020
tattcaatcg tcgcaaatgt cagaagagac tcagcaatgc cagctggaac agtatttcaa     1080
ccaggctttc catgggaaca gatattatcc aactacactg ttgctcagga ggataattta     1140
gaaagacttt tgttagttgc gtctgtgaag agaatggtga tg                        1182
```

<210> SEQ ID NO 62
<211> LENGTH: 394
<212> TYPE: PRT
<213> ORGANISM: Artificial Sequence
<220> FEATURE:
<223> OTHER INFORMATION: VP6 Isolate 67

<400> SEQUENCE: 62

```
Asp Val Leu Phe Ser Ile Ala Lys Thr Val Ser Asp Leu Lys Lys Lys
1               5                   10                  15

Val Val Val Gly Thr Ile Tyr Thr Asn Val Glu Asp Ile Ile Gln Gln
            20                  25                  30

Thr Asn Glu Leu Ile Arg Thr Leu Asn Gly Asn Thr Phe His Thr Gly
        35                  40                  45

Gly Ile Gly Thr Gln Pro Gln Lys Glu Trp Asn Phe Gln Leu Pro Gln
    50                  55                  60

Leu Gly Thr Thr Leu Leu Asn Leu Asp Asp Asn Tyr Val Gln Ala Thr
65                  70                  75                  80

Arg Ser Ile Ile Asp Tyr Leu Thr Ser Phe Ile Glu Ala Val Cys Asp
                85                  90                  95

Asp Glu Ile Val Arg Glu Ala Ser Arg Asn Gly Met Gln Pro Gln Ser
            100                 105                 110

Pro Ala Leu Ile Ala Leu Ser Ser Ala Lys Phe Lys Thr Ile Asn Phe
        115                 120                 125

Asn Asn Ser Ser Gln Ser Ile Lys Asn Trp Ser Ala Gln Ser Arg Arg
    130                 135                 140

Glu Asn Pro Val Tyr Glu Tyr Lys Asn Pro Met Val Phe Glu Tyr Arg
145                 150                 155                 160
```

```
Asn Ser Tyr Ile Leu Gln Arg Ala Asn Ala Gln Tyr Gly Asn Val Met
                165                 170                 175
Gly Leu Arg Tyr Tyr Thr Ala Ser Asn Ala Cys Gln Ile Ala Ala Phe
            180                 185                 190
Asp Ser Thr Leu Ala Glu Asn Ala Pro Asn Gly Thr Gln Arg Phe Ile
        195                 200                 205
Tyr Asn Gly Arg Leu Lys Arg Pro Ile Ser Asn Val Leu Met Lys Ile
    210                 215                 220
Glu Ala Gly Ala Pro Asn Ile Ser Thr Pro Thr Ile Leu Pro Asp Pro
225                 230                 235                 240
Ala Asn Gln Thr Thr Trp Leu Phe Asn Pro Val Gln Ile Met Asn Gly
                245                 250                 255
Thr Phe Thr Ile Glu Phe Tyr Asn Asn Gly Gln Leu Val Asp Leu Ile
            260                 265                 270
Arg Asn Met Gly Val Val Thr Val Arg Thr Phe Asp Thr Tyr Arg Ile
        275                 280                 285
Thr Ile Asp Met Ile Arg Pro Ala Ala Met Thr Gln Tyr Val Gln Arg
    290                 295                 300
Leu Phe Pro Gln Gly Gly Pro Tyr Gln His Gln Ala Ala Tyr Met Ile
305                 310                 315                 320
Thr Leu Ser Ile Leu Asp Ala Thr Thr Glu Ser Val Met Cys Asp Ser
                325                 330                 335
His Ser Val Asp Tyr Ser Ile Val Ala Asn Val Arg Arg Asp Ser Ala
            340                 345                 350
Met Pro Ala Gly Thr Val Phe Gln Pro Gly Phe Pro Trp Glu Gln Ile
        355                 360                 365
Leu Ser Asn Tyr Thr Val Ala Gln Glu Asp Asn Leu Glu Arg Leu Leu
    370                 375                 380
Leu Val Ala Ser Val Lys Arg Met Val Met
385                 390

<210> SEQ ID NO 63
<211> LENGTH: 1182
<212> TYPE: DNA
<213> ORGANISM: Artificial Sequence
<220> FEATURE:
<223> OTHER INFORMATION: VP6 Isolate 68

<400> SEQUENCE: 63
gatgtgctgt tctccattgc gaagactgtc tcagatctta agaagaaagt tgtagttggt      60
actatttata caaatgtaga agatataatc aacagacta atgaattgat tagaactttg     120
aatggcaaca cattccatac tggtggaatt ggaacacaac ctcagaaaga atggaatttt     180
caactaccac agctaggtac aacactttg aatttagatg ataactatgt tcaagcaact     240
agaagtatca tcgattattt ggcctcattt atagaagctg tgtgtgatga cgaaattgtt     300
agagaagcgt caagaaatgg aatgcaacct caatctcctg cacttatagc gttatcttca     360
gcaaaattta agactattaa ttttaacaat agttcacaat ccattaagaa ttggagcgct     420
cagtcaagac gtgaaaatcc agtgtatgaa tataaaaatc caatggtgtt tgagtataga     480
aattcatata ttcttcagcg tgccaatgca caatatggga cgtaatggg gctgagatat     540 tacacagcca gcaatgcctg tcagattgca gcttttgatt caactttagc tgaaaatgcc     600
cctaatggca ctcaacggtt tatttataat ggaagactta aaagaccgat ttctaatgtg     660
ttgatgaaaa tcgaggcggg tgctccaaac attagtaatc caacaatact acctgatcca     720
```

-continued

```
gcaaatcaga caacatggct gtttaatcca gtgcagataa tgaatggaac atttactatt    780
gagttttata ataatgggca gttagttgat ttgattagaa atatgggagt agttactgtt    840
agaacatttg atacgtacag aattacaatt gacatgatta gaccagcaac catgacacag    900
tatgtacaaa gactgtttcc acagggtggc ccatatcaac atcaagccgc atatatgata    960
actcttagta tattggatgc cacaacagaa tcagtcatgt gtgattcaca ttcagtagat   1020
tattcaatcg tcgcaaatgt cagaagagac tcagcaatgc cagctggaac agtatttcaa   1080
ccaggatttc catgggaaca gatattatcc aactacactg ttgctcagga ggataattta   1140
gaaagacttt tgttagttgc gtctgtgaag agaatggtga tg                      1182
```

<210> SEQ ID NO 64
<211> LENGTH: 394
<212> TYPE: PRT
<213> ORGANISM: Artificial Sequence
<220> FEATURE:
<223> OTHER INFORMATION: VP6 Isolate 68

<400> SEQUENCE: 64

```
Asp Val Leu Phe Ser Ile Ala Lys Thr Val Ser Asp Leu Lys Lys Lys
1               5                   10                  15

Val Val Val Gly Thr Ile Tyr Thr Asn Val Glu Asp Ile Ile Gln Gln
            20                  25                  30

Thr Asn Glu Leu Ile Arg Thr Leu Asn Gly Asn Thr Phe His Thr Gly
        35                  40                  45

Gly Ile Gly Thr Gln Pro Gln Lys Glu Trp Asn Phe Gln Leu Pro Gln
    50                  55                  60

Leu Gly Thr Thr Leu Leu Asn Leu Asp Asp Asn Tyr Val Gln Ala Thr
65                  70                  75                  80

Arg Ser Ile Ile Asp Tyr Leu Ala Ser Phe Ile Glu Ala Val Cys Asp
                85                  90                  95

Asp Glu Ile Val Arg Glu Ala Ser Arg Asn Gly Met Gln Pro Gln Ser
            100                 105                 110

Pro Ala Leu Ile Ala Leu Ser Ser Ala Lys Phe Lys Thr Ile Asn Phe
        115                 120                 125

Asn Asn Ser Ser Gln Ser Ile Lys Asn Trp Ser Ala Gln Ser Arg Arg
    130                 135                 140

Glu Asn Pro Val Tyr Glu Tyr Lys Asn Pro Met Val Phe Glu Tyr Arg
145                 150                 155                 160

Asn Ser Tyr Ile Leu Gln Arg Ala Asn Ala Gln Tyr Gly Asn Val Met
                165                 170                 175

Gly Leu Arg Tyr Tyr Thr Ala Ser Asn Ala Cys Gln Ile Ala Ala Phe
            180                 185                 190

Asp Ser Thr Leu Ala Glu Asn Ala Pro Asn Gly Thr Gln Arg Phe Ile
        195                 200                 205

Tyr Asn Gly Arg Leu Lys Arg Pro Ile Ser Asn Val Leu Met Lys Ile
    210                 215                 220

Glu Ala Gly Ala Pro Asn Ile Ser Asn Pro Thr Ile Leu Pro Asp Pro
225                 230                 235                 240

Ala Asn Gln Thr Thr Trp Leu Phe Asn Pro Val Gln Ile Met Asn Gly
                245                 250                 255

Thr Phe Thr Ile Glu Phe Tyr Asn Asn Gly Gln Leu Val Asp Leu Ile
            260                 265                 270

Arg Asn Met Gly Val Val Thr Val Arg Thr Phe Asp Thr Tyr Arg Ile
        275                 280                 285
```

```
Thr Ile Asp Met Ile Arg Pro Ala Thr Met Thr Gln Tyr Val Gln Arg
    290                 295                 300
Leu Phe Pro Gln Gly Gly Pro Tyr Gln His Gln Ala Ala Tyr Met Ile
305                 310                 315                 320
Thr Leu Ser Ile Leu Asp Ala Thr Thr Glu Ser Val Met Cys Asp Ser
                325                 330                 335
His Ser Val Asp Tyr Ser Ile Val Ala Asn Val Arg Arg Asp Ser Ala
            340                 345                 350
Met Pro Ala Gly Thr Val Phe Gln Pro Gly Phe Pro Trp Glu Gln Ile
        355                 360                 365
Leu Ser Asn Tyr Thr Val Ala Gln Glu Asp Asn Leu Glu Arg Leu Leu
    370                 375                 380
Leu Val Ala Ser Val Lys Arg Met Val Met
385                 390
```

<210> SEQ ID NO 65
<211> LENGTH: 1182
<212> TYPE: DNA
<213> ORGANISM: Artificial Sequence
<220> FEATURE:
<223> OTHER INFORMATION: VP6 Isolate 69

<400> SEQUENCE: 65

```
gatgtgctgt tctccattgc gaagactgtc tcagatctta agaagaaagt tgtagttggt    60
actatttata caaatgtaga agatataatc aacagacta  atgaattgat tagaactttg   120
aatggcaaca cattccatac tggtggaatt ggaacacaac ctcagaaaga atggaatttt   180
caactaccac agctaggtac aacacttttg aatttagatg ataactatgt tcaagcaact   240
agaagtatca tcgattattt ggcctcattt atagaagctg tgtgtgatga cgaaattgtt   300
agagaagcgt caagaaatgg aatgcaacct caatctcctg cacttatagc gttatcttca   360
gcaaaattta agactattaa tttaacaat  agttcacaat ccattaagaa ttggagtgct   420
cagtcaagac gtgaaaatcc agtgtatgaa tataaaaatc caatggtgtt tgagtataga   480
aattcatata ttcttcagcg tgccaatgca caatatggga acgtaatggg gctgagatat   540
tacacagcca gcaatgcctg tcagattgca gcttttgatt caactttagc tgaaaatgcc   600
cctaatggca ctcaacggtt tatttataat ggaagactta aaagaccaat ttctaatgtg   660
ttgatgaaaa tcgaggcggg tgctccaaac attagtaatc caacaatact acctgatcca   720
gcaaatcaga caacatggct atttaatcca gtgcagataa tgaatggaac atttactatt   780
gagttttata ataatgggca gttagttgat ttgattagaa atatgggagt agttactgtt   840
agaacatttg atacgtacag aattacaatt gacatgatta gaccagcaac catgacacag   900
tatgtacaaa gactgtttcc acagggtggc ccatatcaac atcaagccgc atatatgata   960
actcttagta tattggatgc cacaacagaa tcagtcatgt gtgattcaca ttcagtagat  1020
tattcaatcg tcgcaaatgt cagaagagac tcagcaatgc cagctggaac agtatttcaa  1080
ccaggatttc catgggaaca gatattatcc aactacactg ttgctcagga ggataattta  1140
gaaagacttt tgttagttgc gtctgtgaag agaatggtga tg                      1182
```

<210> SEQ ID NO 66
<211> LENGTH: 394
<212> TYPE: PRT
<213> ORGANISM: Artificial Sequence
<220> FEATURE:
<223> OTHER INFORMATION: VP6 Isolate 69 AA sequence

<400> SEQUENCE: 66

```
Asp Val Leu Phe Ser Ile Ala Lys Thr Val Ser Asp Leu Lys Lys Lys
1               5                   10                  15

Val Val Val Gly Thr Ile Tyr Thr Asn Val Glu Asp Ile Ile Gln Gln
            20                  25                  30

Thr Asn Glu Leu Ile Arg Thr Leu Asn Gly Asn Thr Phe His Thr Gly
        35                  40                  45

Gly Ile Gly Thr Gln Pro Gln Lys Glu Trp Asn Phe Gln Leu Pro Gln
    50                  55                  60

Leu Gly Thr Thr Leu Leu Asn Leu Asp Asp Asn Tyr Val Gln Ala Thr
65                  70                  75                  80

Arg Ser Ile Ile Asp Tyr Leu Ala Ser Phe Ile Glu Ala Val Cys Asp
                85                  90                  95

Asp Glu Ile Val Arg Glu Ala Ser Arg Asn Gly Met Gln Pro Gln Ser
            100                 105                 110

Pro Ala Leu Ile Ala Leu Ser Ser Ala Lys Phe Lys Thr Ile Asn Phe
        115                 120                 125

Asn Asn Ser Ser Gln Ser Ile Lys Asn Trp Ser Ala Gln Ser Arg Arg
130                 135                 140

Glu Asn Pro Val Tyr Glu Tyr Lys Asn Pro Met Val Phe Glu Tyr Arg
145                 150                 155                 160

Asn Ser Tyr Ile Leu Gln Arg Ala Asn Ala Gln Tyr Gly Asn Val Met
                165                 170                 175

Gly Leu Arg Tyr Tyr Thr Ala Ser Asn Ala Cys Gln Ile Ala Ala Phe
            180                 185                 190

Asp Ser Thr Leu Ala Glu Asn Ala Pro Asn Gly Thr Gln Arg Phe Ile
        195                 200                 205

Tyr Asn Gly Arg Leu Lys Arg Pro Ile Ser Asn Val Leu Met Lys Ile
    210                 215                 220

Glu Ala Gly Ala Pro Asn Ile Ser Asn Pro Thr Ile Leu Pro Asp Pro
225                 230                 235                 240

Ala Asn Gln Thr Thr Trp Leu Phe Asn Pro Val Gln Ile Met Asn Gly
                245                 250                 255

Thr Phe Thr Ile Glu Phe Tyr Asn Asn Gly Gln Leu Val Asp Leu Ile
            260                 265                 270

Arg Asn Met Gly Val Val Thr Val Arg Thr Phe Asp Thr Tyr Arg Ile
        275                 280                 285

Thr Ile Asp Met Ile Arg Pro Ala Thr Met Thr Gln Tyr Val Gln Arg
    290                 295                 300

Leu Phe Pro Gln Gly Gly Pro Tyr Gln His Gln Ala Ala Tyr Met Ile
305                 310                 315                 320

Thr Leu Ser Ile Leu Asp Ala Thr Thr Glu Ser Val Met Cys Asp Ser
                325                 330                 335

His Ser Val Asp Tyr Ser Ile Val Ala Asn Val Arg Arg Asp Ser Ala
            340                 345                 350

Met Pro Ala Gly Thr Val Phe Gln Pro Gly Phe Pro Trp Glu Gln Ile
        355                 360                 365

Leu Ser Asn Tyr Thr Val Ala Gln Glu Asp Asn Leu Glu Arg Leu Leu
    370                 375                 380

Leu Val Ala Ser Val Lys Arg Met Val Met
385                 390
```

<210> SEQ ID NO 67
<211> LENGTH: 1182
<212> TYPE: DNA
<213> ORGANISM: Artificial Sequence
<220> FEATURE:
<223> OTHER INFORMATION: VP6 Isolate 70

<400> SEQUENCE: 67

```
gatgtgctgt tctccattgc gaagactgtc tcagatctta agaagaaagt tgtagttggt      60
actatttata caaatgtaga agatataatc caacagacta atgaattgat tagaactttg     120
aatggcaaca cattccatac tggtggaatt gggacacaac ctcagaaaga atggaatttt     180
caactaccac agctaggtac aacactttttg aatttagatg ataactatgt tcaagcaact    240
agaagtatca tcgattattt ggcctcattt atagaagctg tgtgtgatga tgaaattgtt     300
agagaagcgt caagaaatgg aatgcaacct caatctcctg cacttatagc gttatcttca     360
gcaaaattta agactattaa ttttaacaat agttcacaat ccattaagaa ttggagtgct     420
cagtcaagac gtgaaaatcc agtgtatgaa tataaaaatc caatggtgtt tgagtataga     480
aattcatata ttcttcagcg tgccaatgca caatatggga atgtaatggg gctgagatat     540
tatacagcca gtaatgcctg tcagattgca gcttttgatt caactttagc tgaaaatgcc     600
cctaatggta ctcaacggtt tatttataat ggaagactta aaagaccaat ttctaatgtg     660
ttgatgaaaa ttgaggcggg tgctccaaac attagtaatc taacaatact acctgatcca     720
gcaaatcaga caacatggct atttaatcca gtacaaataa tgaatggaac atttactatt     780
gagtttttata ataatgggca gttagttgat ttgattagaa atatgggagt agttactgtt     840
agaacatttg atacgtacag aatcacaatt gacatgatta gccagcagc catgacacag     900
tatgtacaaa gactgtttcc acagggtggc ccatatcaac atcaagccgc atatatgata     960
actcttagta tattggatgc cacaacagaa tcagtcatgt gtgattcaca ttcagtagat    1020
tattcaatcg tcgcaaatgt cagaagagac tcagcaatgc cagctggaac agtatttcaa    1080
ccaggttttc catgggaaca gatattatcc aactacactg ttgctcagga ggataattta    1140
gaaagacttt tgttagttgc gtctgtgaag agaatggtga tg                       1182
```

<210> SEQ ID NO 68
<211> LENGTH: 394
<212> TYPE: PRT
<213> ORGANISM: Artificial Sequence
<220> FEATURE:
<223> OTHER INFORMATION: VP6 Isolate 70

<400> SEQUENCE: 68

```
Asp Val Leu Phe Ser Ile Ala Lys Thr Val Ser Asp Leu Lys Lys Lys
1               5                   10                  15
Val Val Val Gly Thr Ile Tyr Thr Asn Val Glu Asp Ile Ile Gln Gln
            20                  25                  30
Thr Asn Glu Leu Ile Arg Thr Leu Asn Gly Asn Thr Phe His Thr Gly
        35                  40                  45
Gly Ile Gly Thr Gln Pro Gln Lys Glu Trp Asn Phe Gln Leu Pro Gln
    50                  55                  60
Leu Gly Thr Thr Leu Leu Asn Leu Asp Asp Asn Tyr Val Gln Ala Thr
65                  70                  75                  80
Arg Ser Ile Ile Asp Tyr Leu Ala Ser Phe Ile Glu Ala Val Cys Asp
                85                  90                  95
Asp Glu Ile Val Arg Glu Ala Ser Arg Asn Gly Met Gln Pro Gln Ser
            100                 105                 110
```

```
Pro Ala Leu Ile Ala Leu Ser Ser Ala Lys Phe Lys Thr Ile Asn Phe
        115                 120                 125

Asn Asn Ser Ser Gln Ser Ile Lys Asn Trp Ser Ala Gln Ser Arg Arg
    130                 135                 140

Glu Asn Pro Val Tyr Glu Tyr Lys Asn Pro Met Val Phe Glu Tyr Arg
145                 150                 155                 160

Asn Ser Tyr Ile Leu Gln Arg Ala Asn Ala Gln Tyr Gly Asn Val Met
                165                 170                 175

Gly Leu Arg Tyr Tyr Thr Ala Ser Asn Ala Cys Gln Ile Ala Ala Phe
            180                 185                 190

Asp Ser Thr Leu Ala Glu Asn Ala Pro Asn Gly Thr Gln Arg Phe Ile
        195                 200                 205

Tyr Asn Gly Arg Leu Lys Arg Pro Ile Ser Asn Val Leu Met Lys Ile
    210                 215                 220

Glu Ala Gly Ala Pro Asn Ile Ser Asn Leu Thr Ile Leu Pro Asp Pro
225                 230                 235                 240

Ala Asn Gln Thr Thr Trp Leu Phe Asn Pro Val Gln Ile Met Asn Gly
                245                 250                 255

Thr Phe Thr Ile Glu Phe Tyr Asn Asn Gly Gln Leu Val Asp Leu Ile
            260                 265                 270

Arg Asn Met Gly Val Val Thr Val Arg Thr Phe Asp Thr Tyr Arg Ile
        275                 280                 285

Thr Ile Asp Met Ile Arg Pro Ala Ala Met Thr Gln Tyr Val Gln Arg
    290                 295                 300

Leu Phe Pro Gln Gly Gly Pro Tyr Gln His Gln Ala Ala Tyr Met Ile
305                 310                 315                 320

Thr Leu Ser Ile Leu Asp Ala Thr Thr Glu Ser Val Met Cys Asp Ser
                325                 330                 335

His Ser Val Asp Tyr Ser Ile Val Ala Asn Val Arg Arg Asp Ser Ala
            340                 345                 350

Met Pro Ala Gly Thr Val Phe Gln Pro Gly Phe Pro Trp Glu Gln Ile
        355                 360                 365

Leu Ser Asn Tyr Thr Val Ala Gln Glu Asp Asn Leu Glu Arg Leu Leu
    370                 375                 380

Leu Val Ala Ser Val Lys Arg Met Val Met
385                 390

<210> SEQ ID NO 69
<211> LENGTH: 1182
<212> TYPE: DNA
<213> ORGANISM: Artificial Sequence
<220> FEATURE:
<223> OTHER INFORMATION: VP6 Isolate 71

<400> SEQUENCE: 69
gatgtgctgt tctccattgc gaaaactgtc tcagatctta agaagaaagt tgtagttggt      60
actatttata caaatgtaga agatataatc aacagactaa tgaattaat tagaactttg     120 aatggcaaca cattccatac tggtggaatt ggaacacaac ctcagaaaga atggaatttt     180
caactaccac agctaggtac aacactttg aatttagatg ataactatgt tcaagcaact     240
agaagtatca tcgattattt ggcctcattt atagaagctg tgtgtgatga cgaaattgtt     300
agagaagcgt caagaaatgg aatgcaacct caatctcctg cacttatagc gttatcttca     360
gcaaaattta agactattaa ttttaacaat agttcacaat ccattaagaa ttggagtgct     420
```

```
cagtcaagac gtgaaaatcc agtgtatgaa ataaaaatc caatggtgtt tgagtataga      480
aattcatata ttcttcagcg tgccaatgca caatatggga atgtaatggg gctgagatat      540
tacacagcca gtaatgcctg tcagattgca gcttttgatt caactttagc tgaaaatgcc      600
cctaatggta ctcaacggtt tatttataat ggaagactta aaagaccaat ttctaatgta      660
ttgatgaaaa ttgaggcggg tgctccaaac attagtaatc caacaatact acctgatcca      720
gcaaatcaga caacatggct atttaatcca gtacagataa tgaatggaac atttactatt      780
gagttttata ataatgggca gttagttgat ttgattagaa atatgggagt agttactgtt      840
agaacatttg atacgtacag aattacaatt gacatgatta gaccagcagc catgacgcag      900
tatgttcaaa gactgtttcc acagggtggc ccatatcaac atcaagccgc atatatgata      960
actcttagta tattggatgc cacaacagaa tcagtcatgt gtgattcaca ttcagtagat     1020
tattcaatcg tcgcaaatgt cagaagagac tcagcaatgc cagctggaac agtatttcaa     1080
ccaggctttc catgggaaca gatattatcc aactcactg ttgctcagga ggataattta     1140
gaaagacttt tgttagttgc gtctgtgaag agaatggtga tg                         1182
```

<210> SEQ ID NO 70
<211> LENGTH: 394
<212> TYPE: PRT
<213> ORGANISM: Artificial Sequence
<220> FEATURE:
<223> OTHER INFORMATION: VP6 Isolate 71

<400> SEQUENCE: 70

```
Asp Val Leu Phe Ser Ile Ala Lys Thr Val Ser Asp Leu Lys Lys Lys
1               5                  10                  15

Val Val Val Gly Thr Ile Tyr Thr Asn Val Glu Asp Ile Ile Gln Gln
            20                  25                  30

Thr Asn Glu Leu Ile Arg Thr Leu Asn Gly Asn Thr Phe His Thr Gly
        35                  40                  45

Gly Ile Gly Thr Gln Pro Gln Lys Glu Trp Asn Phe Gln Leu Pro Gln
    50                  55                  60

Leu Gly Thr Thr Leu Leu Asn Leu Asp Asp Asn Tyr Val Gln Ala Thr
65                  70                  75                  80

Arg Ser Ile Ile Asp Tyr Leu Ala Ser Phe Ile Glu Ala Val Cys Asp
                85                  90                  95

Asp Glu Ile Val Arg Glu Ala Ser Arg Asn Gly Met Gln Pro Gln Ser
            100                 105                 110

Pro Ala Leu Ile Ala Leu Ser Ser Ala Lys Phe Lys Thr Ile Asn Phe
        115                 120                 125

Asn Asn Ser Ser Gln Ser Ile Lys Asn Trp Ser Ala Gln Ser Arg Arg
    130                 135                 140

Glu Asn Pro Val Tyr Glu Tyr Lys Asn Pro Met Val Phe Glu Tyr Arg
145                 150                 155                 160

Asn Ser Tyr Ile Leu Gln Arg Ala Asn Ala Gln Tyr Gly Asn Val Met
                165                 170                 175

Gly Leu Arg Tyr Tyr Thr Ala Ser Asn Ala Cys Gln Ile Ala Ala Phe
            180                 185                 190

Asp Ser Thr Leu Ala Glu Asn Ala Pro Asn Gly Thr Gln Arg Phe Ile
        195                 200                 205

Tyr Asn Gly Arg Leu Lys Arg Pro Ile Ser Asn Val Leu Met Lys Ile
    210                 215                 220

Glu Ala Gly Ala Pro Asn Ile Ser Asn Pro Thr Ile Leu Pro Asp Pro
```

```
                    225                 230                 235                 240

Ala Asn Gln Thr Thr Trp Leu Phe Asn Pro Val Gln Ile Met Asn Gly
                        245                 250                 255

Thr Phe Thr Ile Glu Phe Tyr Asn Asn Gly Gln Leu Val Asp Leu Ile
                        260                 265                 270

Arg Asn Met Gly Val Val Thr Val Arg Thr Phe Asp Thr Tyr Arg Ile
                        275                 280                 285

Thr Ile Asp Met Ile Arg Pro Ala Ala Met Thr Gln Tyr Val Gln Arg
                        290                 295                 300

Leu Phe Pro Gln Gly Gly Pro Tyr Gln His Gln Ala Ala Tyr Met Ile
        305                 310                 315                 320

Thr Leu Ser Ile Leu Asp Ala Thr Thr Glu Ser Val Met Cys Asp Ser
                        325                 330                 335

His Ser Val Asp Tyr Ser Ile Val Ala Asn Val Arg Arg Asp Ser Ala
                        340                 345                 350

Met Pro Ala Gly Thr Val Phe Gln Pro Gly Phe Pro Trp Glu Gln Ile
                        355                 360                 365

Leu Ser Asn Tyr Thr Val Ala Gln Glu Asp Asn Leu Glu Arg Leu Leu
                        370                 375                 380

Leu Val Ala Ser Val Lys Arg Met Val Met
        385                 390
```

<210> SEQ ID NO 71
<211> LENGTH: 1182
<212> TYPE: DNA
<213> ORGANISM: Artificial Sequence
<220> FEATURE:
<223> OTHER INFORMATION: VP6 Isolate 72

<400> SEQUENCE: 71

```
gatgtgctgt tctccattgc gaaaactgtc tcagatctta agaagaaagt tgtagttggt      60
actatttata caaatgtaga agatataatc aacagactga tgaattaat tagaactttg     120
aatggcaaca cattccatac tggtggaatt ggaacacaac ctcagaaaga tggaattttt     180
caactaccac agctaggtac aacacttttg aatttagatg ataactatgt tcaagcaact     240
agaagtatca tcgattattt ggcctcattt atagaagctg tgtgtgatga cgaaattgtt     300
agagaagcgt caagaaatgg aatgcaacct caatctcctg cacttatagc gttatcttca     360
gcaaaattta agactattaa ttttaacaat agttcacaat ccattaagaa ttggagtgct     420
cagtcaagac gtgaaaatcc agtgtatgaa tataaaaatc caatggtgtt tgagtataga     480
aattcatata ttcttcagcg tgccaatgca caatatggga atgtaatggg gctgagatat     540
tacacagcca gtaatgcctg tcagattgca gcttttgatt caactttagc tgaaaatgcc     600
cctaatggta ctcaacggtt tatttataat ggaagactta aagaccaat ttctaatgta     660
ttgatgaaaa ttgaggcggg tgctccaaac attagtaatc caacaatact acctgatcca     720
gcaaatcaga caacatggct atttaatcca gtacagataa tgaatggaac atttactatt     780
gagttttata ataatgggca gttagttgat ttgattagaa atatgggagt agttactgtt     840
agaacatttg atacgtacag aattacaatt gacatgatta ccagcagc catgacgcag     900
tatgttcaaa gactgttccc acagggtggc ccatatcaac atcaagccgc atatatgata    960
actcttagta tattggatgc cacaacagaa tcagtcatgt gtgattcaca ttcagtagat    1020
tattcaatcg tcgcaaatgt cagaagagac tcagcaatgc cagctggaac agtatttcaa    1080
ccaggctttc catgggaaca gatattatcc aactacactg ttgctcagga ggataattta    1140
```
gaaagacttt tgttagttgc gtctgtgaag agaatggtga tg                1182

<210> SEQ ID NO 72
<211> LENGTH: 394
<212> TYPE: PRT
<213> ORGANISM: Artificial Sequence
<220> FEATURE:
<223> OTHER INFORMATION: VP6 Isolate 72

<400> SEQUENCE: 72

Asp Val Leu Phe Ser Ile Ala Lys Thr Val Ser Asp Leu Lys Lys Lys
1               5                   10                  15

Val Val Val Gly Thr Ile Tyr Thr Asn Val Glu Asp Ile Ile Gln Gln
            20                  25                  30

Thr Asn Glu Leu Ile Arg Thr Leu Asn Gly Asn Thr Phe His Thr Gly
        35                  40                  45

Gly Ile Gly Thr Gln Pro Gln Lys Glu Trp Asn Phe Gln Leu Pro Gln
    50                  55                  60

Leu Gly Thr Thr Leu Leu Asn Leu Asp Asp Asn Tyr Val Gln Ala Thr
65                  70                  75                  80

Arg Ser Ile Ile Asp Tyr Leu Ala Ser Phe Ile Glu Ala Val Cys Asp
                85                  90                  95

Asp Glu Ile Val Arg Glu Ala Ser Arg Asn Gly Met Gln Pro Gln Ser
            100                 105                 110

Pro Ala Leu Ile Ala Leu Ser Ser Ala Lys Phe Lys Thr Ile Asn Phe
        115                 120                 125

Asn Asn Ser Ser Gln Ser Ile Lys Asn Trp Ser Ala Gln Ser Arg Arg
    130                 135                 140

Glu Asn Pro Val Tyr Glu Tyr Lys Asn Pro Met Val Phe Glu Tyr Arg
145                 150                 155                 160

Asn Ser Tyr Ile Leu Gln Arg Ala Asn Ala Gln Tyr Gly Asn Val Met
                165                 170                 175

Gly Leu Arg Tyr Tyr Thr Ala Ser Asn Ala Cys Gln Ile Ala Ala Phe
            180                 185                 190

Asp Ser Thr Leu Ala Glu Asn Ala Pro Asn Gly Thr Gln Arg Phe Ile
        195                 200                 205

Tyr Asn Gly Arg Leu Lys Arg Pro Ile Ser Asn Val Leu Met Lys Ile
    210                 215                 220

Glu Ala Gly Ala Pro Asn Ile Ser Asn Pro Thr Ile Leu Pro Asp Pro
225                 230                 235                 240

Ala Asn Gln Thr Thr Trp Leu Phe Asn Pro Val Gln Ile Met Asn Gly
                245                 250                 255

Thr Phe Thr Ile Glu Phe Tyr Asn Asn Gly Gln Leu Val Asp Leu Ile
            260                 265                 270

Arg Asn Met Gly Val Val Thr Val Arg Thr Phe Asp Thr Tyr Arg Ile
        275                 280                 285

Thr Ile Asp Met Ile Arg Pro Ala Ala Met Thr Gln Tyr Val Gln Arg
    290                 295                 300

Leu Phe Pro Gln Gly Gly Pro Tyr Gln His Gln Ala Ala Tyr Met Ile
305                 310                 315                 320

Thr Leu Ser Ile Leu Asp Ala Thr Thr Glu Ser Val Met Cys Asp Ser
                325                 330                 335

His Ser Val Asp Tyr Ser Ile Val Ala Asn Val Arg Arg Asp Ser Ala
            340                 345                 350

Met Pro Ala Gly Thr Val Phe Gln Pro Gly Phe Pro Trp Glu Gln Ile
            355                 360                 365

Leu Ser Asn Tyr Thr Val Ala Gln Glu Asp Asn Leu Glu Arg Leu Leu
        370                 375                 380

Leu Val Ala Ser Val Lys Arg Met Val Met
385                 390

<210> SEQ ID NO 73
<211> LENGTH: 33
<212> TYPE: DNA
<213> ORGANISM: Artificial Sequence
<220> FEATURE:
<223> OTHER INFORMATION: KSN760 Rota C Reverse VP4 primer

<400> SEQUENCE: 73
cyttrmtyay yacttyatyh rmdttdattr dbc                                33

<210> SEQ ID NO 74
<211> LENGTH: 34
<212> TYPE: DNA
<213> ORGANISM: Artificial Sequence
<220> FEATURE:
<223> OTHER INFORMATION: KSN761 Rota C Forward VP4 primer

<400> SEQUENCE: 74
atggcgtcct cactttatca gcarttraty tcac                               34

<210> SEQ ID NO 75
<211> LENGTH: 52
<212> TYPE: DNA
<213> ORGANISM: Artificial Sequence
<220> FEATURE:
<223> OTHER INFORMATION: KSN762 Rota C Reverse VP4 primer

<400> SEQUENCE: 75
gtgcggccgc aagcttttac yttrmtyayy acttyatyhr mdttdattrd bc           52

<210> SEQ ID NO 76
<211> LENGTH: 47
<212> TYPE: DNA
<213> ORGANISM: Artificial Sequence
<220> FEATURE:
<223> OTHER INFORMATION: KSN763 Rota C Forward primer

<400> SEQUENCE: 76
ggttccgcgt ggatccgcgt cctcacttta tcagcarttr atytcac                 47

<210> SEQ ID NO 77
<211> LENGTH: 30
<212> TYPE: DNA
<213> ORGANISM: Artificial Sequence
<220> FEATURE:
<223> OTHER INFORMATION: Primer 1 to insert His Tag in pNPL1

<400> SEQUENCE: 77
atgatgatgc atatgtatat ctccttctta                                    30

<210> SEQ ID NO 78
<211> LENGTH: 28
<212> TYPE: DNA
<213> ORGANISM: Artificial Sequence
<220> FEATURE:
<223> OTHER INFORMATION: Primer 2 to insert His Tag in pNPL1

<400> SEQUENCE: 78
catcatcatg gatccgaatt cgagctcc                                          28

<210> SEQ ID NO 79
<211> LENGTH: 32
<212> TYPE: DNA
<213> ORGANISM: Artificial Sequence
<220> FEATURE:
<223> OTHER INFORMATION: Rota C NSP4 FOR for pNPL3

<400> SEQUENCE: 79
tcatcatcat ggatccatca cctcaaaaac tg                                     32

<210> SEQ ID NO 80
<211> LENGTH: 37
<212> TYPE: DNA
<213> ORGANISM: Artificial Sequence
<220> FEATURE:
<223> OTHER INFORMATION: Rota C NSP4 REV for pNPL3 or pNPL1

<400> SEQUENCE: 80
gtgcggccgc aagctttcat agacaaactt ccgtctc                                37

<210> SEQ ID NO 81
<211> LENGTH: 35
<212> TYPE: DNA
<213> ORGANISM: Artificial Sequence
<220> FEATURE:
<223> OTHER INFORMATION: Rota C VP4 FOR for pNPL3

<400> SEQUENCE: 81
tcatcatcat ggatccaggg cgtcctcact ttatc                                  35

<210> SEQ ID NO 82
<211> LENGTH: 35
<212> TYPE: DNA
<213> ORGANISM: Artificial Sequence
<220> FEATURE:
<223> OTHER INFORMATION: Rota C VP4 REV for pNPL3 or pNPL1

<400> SEQUENCE: 82
gtgcggccgc aagcttttat aacaccatca ttctc                                  35

<210> SEQ ID NO 83
<211> LENGTH: 35
<212> TYPE: DNA
<213> ORGANISM: Artificial Sequence
<220> FEATURE:
<223> OTHER INFORMATION: Rota C VP6 FOR for pNPL3

<400> SEQUENCE: 83
tcatcatcat ggatccgacg tgctgttttc aattg                                  35

<210> SEQ ID NO 84
<211> LENGTH: 35
<212> TYPE: DNA
<213> ORGANISM: Artificial Sequence
<220> FEATURE:
<223> OTHER INFORMATION: Rota C VP6 REV for pNPL3 or pNPL1

<400> SEQUENCE: 84
gtgcggccgc aagcttctac atcaccattc tcttc                                  35

<210> SEQ ID NO 85
<211> LENGTH: 32
<212> TYPE: DNA
<213> ORGANISM: Artificial Sequence

```
<220> FEATURE:
<223> OTHER INFORMATION: Rota C NSP4 FOR for pNPL1

<400> SEQUENCE: 85
aatgggtcgc ggatccatca cctcaaaaac tg                                32

<210> SEQ ID NO 86
<211> LENGTH: 35
<212> TYPE: DNA
<213> ORGANISM: Artificial Sequence
<220> FEATURE:
<223> OTHER INFORMATION: Rota C VP4 FOR for pNPL1

<400> SEQUENCE: 86
aatgggtcgc ggatccaggg cgtcctcact ttatc                             35

<210> SEQ ID NO 87
<211> LENGTH: 35
<212> TYPE: DNA
<213> ORGANISM: Artificial Sequence
<220> FEATURE:
<223> OTHER INFORMATION: Rota C VP6 FOR for pNPL1

<400> SEQUENCE: 87
aatgggtcgc ggatccgacg tgctgttttc aattg                             35

<210> SEQ ID NO 88
<211> LENGTH: 31
<212> TYPE: DNA
<213> ORGANISM: Artificial Sequence
<220> FEATURE:
<223> OTHER INFORMATION: Rota C VP7 FOR for pNPL3

<400> SEQUENCE: 88
tcatcatcat ggatccgttt gtgcaacatt g                                 31

<210> SEQ ID NO 89
<211> LENGTH: 35
<212> TYPE: DNA
<213> ORGANISM: Artificial Sequence
<220> FEATURE:
<223> OTHER INFORMATION: Rota C VP7 REV for pNPL3 or pNPL1

<400> SEQUENCE: 89
gtgcggccgc aagcttttac gcgtatctta gcatc                             35

<210> SEQ ID NO 90
<211> LENGTH: 996
<212> TYPE: DNA
<213> ORGANISM: Artificial Sequence
<220> FEATURE:
<223> OTHER INFORMATION: VP7 Sequence: Complete ORF
<220> FEATURE:
<221> NAME/KEY: misc_feature
<222> LOCATION: (781)..(781)
<223> OTHER INFORMATION: n is a, c, g, or t

<400> SEQUENCE: 90
atggtttgtg caacattgta cactgtttgc gttatactct gcattctttt tatatacact   60
ttactgttta gaaaaatgtt ccacctaatt actgatacat taatcataac tttaataata  120
tctaactgta ttggatggac acatggtcaa atgtttattg atgacatgaa ttataatgga  180
aacgttgaaa tagtcattaa cgctactgat ccattcaatg tagaatctct atgtatatat  240
tttccaaatg ctgttgtagg atcacaagga cctggtcaaa cgaatggcca tttaaatgat  300
```

|  |  |  |  |  |  |  |  | |
|---|---|---|---|---|---|---|---|---|
| ggaaattatg | ctcaaacaat | tgctacctta | tttgagacaa | aaggattccc | aaaaggctca | 360 |
| gtaacactta | aaacatacat | taaagcttca | gattttatta | gttcagtaga | gatgacttgt | 420 |
| tcgtataatg | tagttataat | acctgatgat | ccaaataagt | cagaggagat | tgaacaaata | 480 |
| gcagaatgga | ttctgaatgt | ttggagatgt | gatgatatgg | atttaactat | ttatacttac | 540 |
| gaacaaacag | gaatagataa | tttgtgggct | gcttttggtg | acgattgtga | tatatctgtt | 600 |
| tgtccactag | acactacaat | gcatggaatt | ggatgttcac | ctgcaagtac | agaaacatat | 660 |
| gaagtattat | caaataacac | gcaagtagcg | ttaattaatg | ttgtagataa | tgtaaaacac | 720 |
| agaattcaaa | tgaatactgg | tcattgtaag | ttaaagaatt | gtgtgaaagg | cgaagcaaga | 780 |
| ntaaatactg | caatagtaag | aatttcaaag | tcatcaagct | ttgataattc | attgtcacca | 840 |
| ttaaataatg | gtcaaactac | acgatcattt | aaaataaacg | ctaagaaatg | gtggacaata | 900 |
| ttttatacaa | taattgatta | cattaataca | attgtacaga | caatgactcc | tagacatagg | 960 |
| gccatttacc | cagaaggttg | gatgctaaga | tacgcg |  |  | 996 |

<210> SEQ ID NO 91
<211> LENGTH: 332
<212> TYPE: PRT
<213> ORGANISM: Artificial Sequence
<220> FEATURE:
<223> OTHER INFORMATION: VP7 Sequence: Complete ORF
<220> FEATURE:
<221> NAME/KEY: misc_feature
<222> LOCATION: (261)..(261)
<223> OTHER INFORMATION: Xaa can be any naturally occurring amino acid

<400> SEQUENCE: 91

Met Val Cys Ala Thr Leu Tyr Thr Val Cys Val Ile Leu Cys Ile Leu
1               5                   10                  15

Phe Ile Tyr Thr Leu Leu Phe Arg Lys Met Phe His Leu Ile Thr Asp
            20                  25                  30

Thr Leu Ile Ile Thr Leu Ile Ile Ser Asn Cys Ile Gly Trp Thr His
        35                  40                  45

Gly Gln Met Phe Ile Asp Asp Met Asn Tyr Asn Gly Asn Val Glu Ile
    50                  55                  60

Val Ile Asn Ala Thr Asp Pro Phe Asn Val Glu Ser Leu Cys Ile Tyr
65                  70                  75                  80

Phe Pro Asn Ala Val Val Gly Ser Gln Gly Pro Gly Gln Thr Asn Gly
                85                  90                  95

His Leu Asn Asp Gly Asn Tyr Ala Gln Thr Ile Ala Thr Leu Phe Glu
            100                 105                 110

Thr Lys Gly Phe Pro Lys Gly Ser Val Thr Leu Lys Thr Tyr Ile Lys
        115                 120                 125

Ala Ser Asp Phe Ile Ser Ser Val Glu Met Thr Cys Ser Tyr Asn Val
    130                 135                 140

Val Ile Ile Pro Asp Asp Pro Asn Lys Ser Glu Glu Ile Glu Gln Ile
145                 150                 155                 160

Ala Glu Trp Ile Leu Asn Val Trp Arg Cys Asp Asp Met Asp Leu Thr
                165                 170                 175

Ile Tyr Thr Tyr Glu Gln Thr Gly Ile Asp Asn Leu Trp Ala Ala Phe
            180                 185                 190

Gly Asp Asp Cys Asp Ile Ser Val Cys Pro Leu Asp Thr Thr Met His
        195                 200                 205

Gly Ile Gly Cys Ser Pro Ala Ser Thr Glu Thr Tyr Glu Val Leu Ser
    210                 215                 220

```
Asn Asn Thr Gln Val Ala Leu Ile Asn Val Val Asp Asn Val Lys His
225                 230                 235                 240

Arg Ile Gln Met Asn Thr Gly His Cys Lys Leu Lys Asn Cys Val Lys
                245                 250                 255

Gly Glu Ala Arg Xaa Asn Thr Ala Ile Val Arg Ile Ser Lys Ser Ser
            260                 265                 270

Ser Phe Asp Asn Ser Leu Ser Pro Leu Asn Asn Gly Gln Thr Thr Arg
        275                 280                 285

Ser Phe Lys Ile Asn Ala Lys Lys Trp Trp Thr Ile Phe Tyr Thr Ile
        290                 295                 300

Ile Asp Tyr Ile Asn Thr Ile Val Gln Thr Met Thr Pro Arg His Arg
305                 310                 315                 320

Ala Ile Tyr Pro Glu Gly Trp Met Leu Arg Tyr Ala
                325                 330
```

<210> SEQ ID NO 92
<211> LENGTH: 2208
<212> TYPE: DNA
<213> ORGANISM: Artificial Sequence
<220> FEATURE:
<223> OTHER INFORMATION: VP4 Complete ORF GenBank (M74218)

<400> SEQUENCE: 92

```
atggcgtcct cactttatca gcagttaatt tcacaaaatt attattctat tggaaacgaa      60
atattaacag atcaacagac aacagaaact gtagtagatt atgtagatgc tggtaattat     120
acatacgcgc aattaccacc tactaaatgg ggagcacgtg ggactttttaa gtctgcattt     180
aatgtatcaa atataactgg acctcatacg aatacaataa tagaatggag taatttacta     240
aattctaacg gatgggtcat ttatcaaaaa ccggccaata ctacaaaatt atttaaacat     300
ggaccagaaa cttataacag taacttggca gcatttgaat tatggtatgg taaagctggt     360
acatcagtta tcatcagacta ttattcttca ttacagaata atgaaaaaac tgtgacagct     420
acttcagatt cattgatact attttggaat gaaggatcta cagtgttagc taataaaaag     480
gtaaatttta gctgggacat gggtggtatg ttaataaaac ctacgagagg caatagagtg     540
gacatctgca tggcaaacat gaatgatttc aatagtagca tatttaattg ggaagaatgg     600
aaacatgaat ttccacgcag tgatgttaat ataaatgtta atatgtatac agattattat     660
cttgcgagtg aagatcctta tactgaactt aaagcactac agcaaccaaa cattacaact     720
tttgagatga aatgatgaa ataatccgt aatgggtcaa taacttgaa tgaagtagta     780
agtaaagact cactatggca ggaggtaaga tatgctaggg atataacgtt agagtgtaag     840
atagaatcag aagtagtcaa aggtggtgga tggggttatg actacacgag tgtagctttt     900
aaaactgtta atcatacata cacgtatact cgagctggtg aaatagtaaa tgcacatgtt     960
accattagtt ttaataatat gaagaacga tcatacgggg gttcattacc gactgatttc    1020
aaaataggaa ggtttgatgt aattgatact gatacttata tgtatataga ttattgggac    1080
gattcagaaa ttttcaaaaa tatggtgtat gtgcgtgatt taagtgctaa cattggtggt    1140
ttctttatt atgctgaaat gtcatattat tttcaaattc ctgtaggtgc acatccagga    1200
ttacattcat caggagtaag atttgtatat gaaagatgtc ttttatcaca acaattcact    1260
gaccaagttg cacttaactc tatgaggttc atatttagag tgacagaatc aaatggttgg    1320
tttatgacat caggtaatat taatactaga cggatagcat caggaactgg atttgcatat    1380
gcagacgggc atacttctca aacagttgga aatattactt tcatatcatt gatcccaagt    1440
```

```
aatccaaatt atcagacacc aatagcatca tcaagcacag tcaggatgga tttagaaagg    1500
aagataaatg atttacgtaa tgattttaat cagctagcta attcagtcgc attaggtgac    1560
attctatctt tggcaacttc accactaact tttgctaatt tgcttgaatc agtgcctgct    1620
atcgcttcat cagttaaaga tgttgcagct aatgtaatga aaaaatttag aaacactaaa    1680
atgtttaaaa aagctacaaa agctaaatat agtgagttta ttattggaga tttgttggaa    1740
gatgtaacga atgttgcacg aaattcaaat ggcatgaatt ttgatgacat tacatccgct    1800
gtgatggtat caactactaa taaactacaa cttactgacg tagacacact ctcagagatt    1860
gtcgctagat cagctgataa ttttatccct aacagatctt acagaatgat agaagacggt    1920
attgtgtatg aagcaacacc aaaacgaact ttctcatacg atcttacaac attgcaacag    1980
agggaatttg acatagataa gttcatgcga ttggcatcta aatcaccagt aatatctgca    2040
atagtagatt ttgcaacatt aaaggctatg agagaaacat atggtgtagg aacggacgta    2100
atatacaaat tagtagcctc agatgctcca acgatattat cattcatcga taacaacaat    2160
ccgttgatta aaagtagaat tgaggaacta ttaagacaat gcagatta                2208
```

<210> SEQ ID NO 93
<211> LENGTH: 736
<212> TYPE: PRT
<213> ORGANISM: Artificial Sequence
<220> FEATURE:
<223> OTHER INFORMATION: VP4 Complete ORF GenBank (M74218)

<400> SEQUENCE: 93

```
Met Ala Ser Ser Leu Tyr Gln Gln Leu Ile Ser Gln Asn Tyr Tyr Ser
1               5                   10                  15

Ile Gly Asn Glu Ile Leu Thr Asp Gln Gln Thr Thr Glu Thr Val Val
            20                  25                  30

Asp Tyr Val Asp Ala Gly Asn Tyr Thr Tyr Ala Gln Leu Pro Pro Thr
        35                  40                  45

Lys Trp Gly Ala Arg Gly Thr Phe Lys Ser Ala Phe Asn Val Ser Asn
    50                  55                  60

Ile Thr Gly Pro His Thr Asn Thr Ile Ile Glu Trp Ser Asn Leu Leu
65                  70                  75                  80

Asn Ser Asn Gly Trp Val Ile Tyr Gln Lys Pro Ala Asn Thr Thr Lys
                85                  90                  95

Leu Phe Lys His Gly Pro Glu Thr Tyr Asn Ser Asn Leu Ala Ala Phe
            100                 105                 110

Glu Leu Trp Tyr Gly Lys Ala Gly Thr Ser Val Thr Ser Asp Tyr Tyr
        115                 120                 125

Ser Ser Leu Gln Asn Asn Glu Lys Thr Val Thr Ala Thr Ser Asp Ser
    130                 135                 140

Leu Ile Leu Phe Trp Asn Glu Gly Ser Thr Val Leu Ala Asn Lys Lys
145                 150                 155                 160

Val Asn Phe Ser Trp Asp Met Gly Gly Met Leu Ile Lys Pro Thr Arg
                165                 170                 175

Gly Asn Arg Val Asp Ile Cys Met Ala Asn Met Asn Asp Phe Asn Ser
            180                 185                 190

Ser Ile Phe Asn Trp Glu Glu Trp Lys His Glu Phe Pro Arg Ser Asp
        195                 200                 205

Val Asn Ile Asn Val Asn Met Tyr Thr Asp Tyr Tyr Leu Ala Ser Glu
    210                 215                 220
```

```
Asp Pro Tyr Thr Glu Leu Lys Ala Leu Gln Gln Pro Asn Ile Thr Thr
225                 230                 235                 240

Phe Glu Met Lys Met Met Lys Ile Ile Arg Asn Gly Ser Ile Asn Leu
            245                 250                 255

Asn Glu Val Val Ser Lys Asp Ser Leu Trp Gln Glu Val Arg Tyr Ala
        260                 265                 270

Arg Asp Ile Thr Leu Glu Cys Lys Ile Glu Ser Glu Val Val Lys Gly
    275                 280                 285

Gly Gly Trp Gly Tyr Asp Tyr Thr Ser Val Ala Phe Lys Thr Val Asn
290                 295                 300

His Thr Tyr Thr Tyr Thr Arg Ala Gly Glu Ile Val Asn Ala His Val
305                 310                 315                 320

Thr Ile Ser Phe Asn Asn Met Lys Glu Arg Ser Tyr Gly Gly Ser Leu
                325                 330                 335

Pro Thr Asp Phe Lys Ile Gly Arg Phe Asp Val Ile Asp Thr Asp Thr
            340                 345                 350

Tyr Met Tyr Ile Asp Tyr Trp Asp Ser Glu Ile Phe Lys Asn Met
        355                 360                 365

Val Tyr Val Arg Asp Leu Ser Ala Asn Ile Gly Gly Phe Phe Tyr Tyr
    370                 375                 380

Ala Glu Met Ser Tyr Tyr Phe Gln Ile Pro Val Gly Ala His Pro Gly
385                 390                 395                 400

Leu His Ser Ser Gly Val Arg Phe Val Tyr Glu Arg Cys Leu Leu Ser
                405                 410                 415

Gln Gln Phe Thr Asp Gln Val Ala Leu Asn Ser Met Arg Phe Ile Phe
            420                 425                 430

Arg Val Thr Glu Ser Asn Gly Trp Phe Met Thr Ser Gly Asn Ile Asn
        435                 440                 445

Thr Arg Arg Ile Ala Ser Gly Thr Gly Phe Ala Tyr Ala Asp Gly His
    450                 455                 460

Thr Ser Gln Thr Val Gly Asn Ile Thr Phe Ile Ser Leu Ile Pro Ser
465                 470                 475                 480

Asn Pro Asn Tyr Gln Thr Pro Ile Ala Ser Ser Ser Thr Val Arg Met
                485                 490                 495

Asp Leu Glu Arg Lys Ile Asn Asp Leu Arg Asn Asp Phe Asn Gln Leu
            500                 505                 510

Ala Asn Ser Val Ala Leu Gly Asp Ile Leu Ser Leu Ala Thr Ser Pro
        515                 520                 525

Leu Thr Phe Ala Asn Leu Leu Glu Ser Val Pro Ala Ile Ala Ser Ser
530                 535                 540

Val Lys Asp Val Ala Ala Asn Val Met Lys Lys Phe Arg Asn Thr Lys
545                 550                 555                 560

Met Phe Lys Lys Ala Thr Lys Ala Lys Tyr Ser Glu Phe Ile Ile Gly
                565                 570                 575

Asp Leu Leu Glu Asp Val Thr Asn Val Ala Arg Asn Ser Asn Gly Met
            580                 585                 590

Asn Phe Asp Asp Ile Thr Ser Ala Val Met Val Ser Thr Thr Asn Lys
        595                 600                 605

Leu Gln Leu Thr Asp Val Asp Thr Leu Ser Glu Ile Val Ala Arg Ser
    610                 615                 620

Ala Asp Asn Phe Ile Pro Asn Arg Ser Tyr Arg Met Ile Glu Asp Gly
625                 630                 635                 640

Ile Val Tyr Glu Ala Thr Pro Lys Arg Thr Phe Ser Tyr Asp Leu Thr
```

```
              645              650              655
Thr Leu Gln Gln Arg Glu Phe Asp Ile Asp Lys Phe Met Arg Leu Ala
            660              665              670

Ser Lys Ser Pro Val Ile Ser Ala Ile Val Asp Phe Ala Thr Leu Lys
            675              680              685

Ala Met Arg Glu Thr Tyr Gly Val Gly Thr Asp Val Ile Tyr Lys Leu
            690              695              700

Val Ala Ser Asp Ala Pro Thr Ile Leu Ser Phe Ile Asp Asn Asn Asn
705              710              715              720

Pro Leu Ile Lys Ser Arg Ile Glu Glu Leu Leu Arg Gln Cys Arg Leu
            725              730              735

<210> SEQ ID NO 94
<211> LENGTH: 2229
<212> TYPE: DNA
<213> ORGANISM: Artificial Sequence
<220> FEATURE:
<223> OTHER INFORMATION: Triple fusion of Rota C NSP4-VP4-VP6

<400> SEQUENCE: 94
atcacctcaa aaactgtgat tgaaagattt aaaactgaaa acaatactaa tgatcaaagc      60
ggtaatattc atgaagaata tgaagaggta atgaaacaaa tgcgtgagat gaaaattcat     120
ttgactgcgc tatttaataa tatacacaaa gataatatgg agtggaggat gagtgaatca     180
attcgcagag aaaagaaacg tgaaatgaaa gcgaatacag ccgagaatgt aattaaaaat     240
gatgtaaata tgttaacat atgtgatacg tcaggactgg agacggaagt ttgtctaagg      300
gcgtcctcac tttatcagca attaatctca caaaattatt attcaactgg taatgaaatt     360
ttgttggata gacagactac cagaaccact aaagattacg tagaagctgg aaattataca     420
tatgctcaat taccaccaac ggagtgggga gcagggtcaa cctttgaatc tacattcaaa     480
tcatcaaata taactggtcc acacaataac acagtcattg aatggagtaa tttaatgaat     540
tctgatattt ggttattgta tcaaaaacca ttggatataa ctgcaccaat cagattatta     600
aaacatggac cggaaaatca tgctgatgta gcagcttttg aattatggta tggtaaagct     660
ggtcataccg tgacatcaat atattattca gcaatatcta atcctaataa tactgttacg     720
ttaacgtcgg attcattagt tctatttttgg aacgaaggtc aaacgatact ggatacaaag    780
acagtcaatt taattggaa tatgggtggt atattagtta gaccgtcaag aggtacacgt      840
gtggacattt gtatgtctga tatggacaat acagatggta ctaattttaa ttggattcaa     900
tggaagcatg agttccccccg tagtagtagt aatgctaatg ttagtatgta tgttaatat      960 tatctagcaa gtagtgatcc ataccatgaa ctcaaagagt tgcaaagacc agcagtaaca    1020
actataaata tgagaatgat ggtgttagac gtgctgtttt caattgcaaa gactgtttca    1080
gatctcaaga gaaagttgt agttggtact atttatacaa atgtagaaga tataattcaa     1140
cagactaacg aattgattag aactttaaat ggcaacacat ccatactgg tggaattgga     1200 acacaacctc aaaagaatg aactttcag ctaccacagc taggtacaac actcttgaat      1260
ttggatgata actatgttca agcaactaga agtattattg attacttagc ctcattcata    1320
gaagcagtgt gtgatgacga aattgttaga gaagcgtcaa gaatggaat gcaacctcaa     1380 tcccctgcat ttatagcatt atcttcatca aaatttaaga ctattaattt taacaatagt    1440
tcgcaatcca ttaaaaattg gagtgctcaa tcaagacgtg agaatccagt ttatgaatac    1500
aaaaatccga tggtattttga atatagaaat tcgtacattc ttcagcgtgc taatgcacaa    1560
```

-continued

```
tttgggaacg taatgggact gagatattac acagccagca atgtctgtca gattgcagct    1620
tttgattcaa ctcttgctga aaatgctcct aatggcgctc aacgtttat ctataatgga     1680 agacttaaga gaccaatttc taatgtgttg atgaaaattg aagcaggcgc tccaaatatt    1740
aataatccaa caatactacc tgatccagca aaccaaacta catggttatt taatccagtg    1800
cagataatga atggaacgtt cactattgaa ttttacaaca atggacaatt ggtcgatttg    1860
attagaaata tgggagtggt tactgttaga acgtttgata catacagaat tacaattgat    1920
atgattagac cagcagccat gacacagtat gtacaaagac tgttcccaca aggtggccca    1980
tatcaacatc aagctgcata tatgatgaca cttagtatat tagatgctac aacagaatca    2040
gttatgtgcg attcacattc agtagactat tcaattgttg caaatgtcag aagagattca    2100
gcgatgccag ctggaacagt atttcagcca ggctttccat gggaacagac gttatccaac    2160
tacactgttg ctcaggaaga caatttagaa agactttat tggttgcgtc tgtgaagaga     2220
atggtgatg                                                            2229
```

<210> SEQ ID NO 95
<211> LENGTH: 743
<212> TYPE: PRT
<213> ORGANISM: Artificial Sequence
<220> FEATURE:
<223> OTHER INFORMATION: Triple fusion Rota C NSP4-VP4-VP6

<400> SEQUENCE: 95

```
Ile Thr Ser Lys Thr Val Ile Glu Arg Phe Lys Thr Glu Asn Asn Thr
1               5                   10                  15

Asn Asp Gln Ser Gly Asn Ile His Glu Glu Tyr Glu Val Met Lys
            20                  25                  30

Gln Met Arg Glu Met Lys Ile His Leu Thr Ala Leu Phe Asn Asn Ile
        35                  40                  45

His Lys Asp Asn Met Glu Trp Arg Met Ser Glu Ser Ile Arg Arg Glu
    50                  55                  60

Lys Lys Arg Glu Met Lys Ala Asn Thr Ala Glu Asn Val Ile Lys Asn
65                  70                  75                  80

Asp Val Asn Asn Val Asn Ile Cys Asp Thr Ser Gly Leu Glu Thr Glu
                85                  90                  95

Val Cys Leu Arg Ala Ser Ser Leu Tyr Gln Gln Leu Ile Ser Gln Asn
            100                 105                 110

Tyr Tyr Ser Thr Gly Asn Glu Ile Leu Leu Asp Arg Gln Thr Thr Arg
        115                 120                 125

Thr Thr Lys Asp Tyr Val Glu Ala Gly Asn Tyr Thr Tyr Ala Gln Leu
    130                 135                 140

Pro Pro Thr Glu Trp Gly Ala Gly Ser Thr Phe Glu Ser Thr Phe Lys
145                 150                 155                 160

Ser Ser Asn Ile Thr Gly Pro His Asn Asn Thr Val Ile Glu Trp Ser
                165                 170                 175

Asn Leu Met Asn Ser Asp Ile Trp Leu Leu Tyr Gln Lys Pro Leu Asp
            180                 185                 190

Ile Thr Ala Pro Ile Arg Leu Leu Lys His Gly Pro Glu Asn His Ala
        195                 200                 205

Asp Val Ala Ala Phe Glu Leu Trp Tyr Gly Lys Ala Gly His Thr Val
    210                 215                 220

Thr Ser Ile Tyr Tyr Ser Ala Ile Ser Asn Pro Asn Asn Thr Val Thr
225                 230                 235                 240
```

```
Leu Thr Ser Asp Ser Leu Val Leu Phe Trp Asn Glu Gly Gln Thr Ile
            245                 250                 255

Leu Asp Thr Lys Thr Val Asn Phe Asn Trp Asn Met Gly Gly Ile Leu
            260                 265                 270

Val Arg Pro Ser Arg Gly Thr Arg Val Asp Ile Cys Met Ser Asp Met
            275                 280                 285

Asp Asn Thr Asp Gly Thr Asn Phe Asn Trp Ile Gln Trp Lys His Glu
            290                 295                 300

Phe Pro Arg Ser Ser Ser Asn Ala Asn Val Ser Met Tyr Val Glu Tyr
305                 310                 315                 320

Tyr Leu Ala Ser Ser Asp Pro Tyr His Glu Leu Lys Glu Leu Gln Arg
            325                 330                 335

Pro Ala Val Thr Thr Ile Asn Met Arg Met Met Val Leu Asp Val Leu
            340                 345                 350

Phe Ser Ile Ala Lys Thr Val Ser Asp Leu Lys Lys Lys Val Val Val
            355                 360                 365

Gly Thr Ile Tyr Thr Asn Val Glu Asp Ile Ile Gln Gln Thr Asn Glu
            370                 375                 380

Leu Ile Arg Thr Leu Asn Gly Asn Thr Phe His Thr Gly Ile Gly
385                 390                 395                 400

Thr Gln Pro Gln Lys Glu Trp Asn Phe Gln Leu Pro Gln Leu Gly Thr
            405                 410                 415

Thr Leu Leu Asn Leu Asp Asp Asn Tyr Val Gln Ala Thr Arg Ser Ile
            420                 425                 430

Ile Asp Tyr Leu Ala Ser Phe Ile Glu Ala Val Cys Asp Asp Glu Ile
            435                 440                 445

Val Arg Glu Ala Ser Arg Asn Gly Met Gln Pro Gln Ser Pro Ala Phe
            450                 455                 460

Ile Ala Leu Ser Ser Ser Lys Phe Lys Thr Ile Asn Phe Asn Asn Ser
465                 470                 475                 480

Ser Gln Ser Ile Lys Asn Trp Ser Ala Gln Ser Arg Arg Glu Asn Pro
            485                 490                 495

Val Tyr Glu Tyr Lys Asn Pro Met Val Phe Glu Tyr Arg Asn Ser Tyr
            500                 505                 510

Ile Leu Gln Arg Ala Asn Ala Gln Phe Gly Asn Val Met Gly Leu Arg
            515                 520                 525

Tyr Tyr Thr Ala Ser Asn Val Cys Gln Ile Ala Ala Phe Asp Ser Thr
            530                 535                 540

Leu Ala Glu Asn Ala Pro Asn Gly Ala Gln Arg Phe Ile Tyr Asn Gly
545                 550                 555                 560

Arg Leu Lys Arg Pro Ile Ser Asn Val Leu Met Lys Ile Glu Ala Gly
            565                 570                 575

Ala Pro Asn Ile Asn Asn Pro Thr Ile Leu Pro Asp Pro Ala Asn Gln
            580                 585                 590

Thr Thr Trp Leu Phe Asn Pro Val Gln Ile Met Asn Gly Thr Phe Thr
            595                 600                 605

Ile Glu Phe Tyr Asn Asn Gly Gln Leu Val Asp Leu Ile Arg Asn Met
            610                 615                 620

Gly Val Val Thr Val Arg Thr Phe Asp Thr Tyr Arg Ile Thr Ile Asp
625                 630                 635                 640

Met Ile Arg Pro Ala Ala Met Thr Gln Tyr Val Gln Arg Leu Phe Pro
            645                 650                 655

Gln Gly Gly Pro Tyr Gln His Gln Ala Ala Tyr Met Met Thr Leu Ser
```

```
                        660                 665                 670
Ile Leu Asp Ala Thr Thr Glu Ser Val Met Cys Asp Ser His Ser Val
                675                 680                 685

Asp Tyr Ser Ile Val Ala Asn Val Arg Arg Asp Ser Ala Met Pro Ala
                690                 695                 700

Gly Thr Val Phe Gln Pro Gly Phe Pro Trp Glu Gln Thr Leu Ser Asn
705                 710                 715                 720

Tyr Thr Val Ala Gln Glu Asp Asn Leu Glu Arg Leu Leu Leu Val Ala
                725                 730                 735

Ser Val Lys Arg Met Val Met
                740

<210> SEQ ID NO 96
<211> LENGTH: 34
<212> TYPE: DNA
<213> ORGANISM: Artificial Sequence
<220> FEATURE:
<223> OTHER INFORMATION: NSP4 forward primer

<400> SEQUENCE: 96
aagtgaggac gcccttagac aaacttccgt ctcc                              34

<210> SEQ ID NO 97
<211> LENGTH: 19
<212> TYPE: DNA
<213> ORGANISM: Artificial Sequence
<220> FEATURE:
<223> OTHER INFORMATION: VP4 Forward primer

<400> SEQUENCE: 97
agggcgtcct cactttatc                                               19

<210> SEQ ID NO 98
<211> LENGTH: 31
<212> TYPE: DNA
<213> ORGANISM: Artificial Sequence
<220> FEATURE:
<223> OTHER INFORMATION: VP4 Reverse Primer

<400> SEQUENCE: 98
tgaaaacagc acgtctaaca ccatcattct c                                 31

<210> SEQ ID NO 99
<211> LENGTH: 20
<212> TYPE: DNA
<213> ORGANISM: Artificial Sequence
<220> FEATURE:
<223> OTHER INFORMATION: VP6 Forward Primer

<400> SEQUENCE: 99
gacgtgctgt tttcaattgc                                              20
```